US00RE44042E

(19) United States
(12) Reissued Patent
Yun et al.

(10) Patent Number: US RE44,042 E
(45) Date of Reissued Patent: Mar. 5, 2013

(54) SYSTEM AND METHOD FOR OPTICAL COHERENCE IMAGING

(75) Inventors: Seok-Hyun Yun, Cambridge, MA (US); Brett Eugene Bouma, Quincy, MA (US); Guillermo J. Tearney, Cambridge, MA (US); Johannes F. De Boer, Amstelveen (NL)

(73) Assignee: The General Hospital Corporation, Boston, MA (US)

(21) Appl. No.: 12/277,178

(22) Filed: Nov. 24, 2008

Related U.S. Patent Documents

Reissue of:
(64) Patent No.: 7,365,859
Issued: Apr. 29, 2008
Appl. No.: 11/225,840
Filed: Sep. 12, 2005

U.S. Applications:
(60) Provisional application No. 60/608,800, filed on Sep. 10, 2004.

(51) Int. Cl.
*G01B 11/02* (2006.01)

(52) U.S. Cl. ..... 356/497; 356/479

(58) Field of Classification Search ..... 356/450–521; 600/476–480

See application file for complete search history.

(56) References Cited

U.S. PATENT DOCUMENTS

| | | | |
|---|---|---|---|
| 2,339,754 | A | 1/1944 | Brace |
| 3,090,753 | A | 5/1963 | Matuszak et al. |
| 3,872,407 | A | 3/1975 | Hughes |
| 4,030,831 | A | 6/1977 | Gowrinathan |
| 4,140,364 | A | 2/1979 | Yamashita et al. |
| 4,224,929 | A | 9/1980 | Furihata |
| 4,295,738 | A | 10/1981 | Meltz et al. |
| 4,300,816 | A | 11/1981 | Snitzer et al. |
| 4,585,349 | A | 4/1986 | Gross et al. |
| 4,601,036 | A | 7/1986 | Faxvog et al. |

(Continued)

FOREIGN PATENT DOCUMENTS

| | | |
|---|---|---|
| CN | 1550203 | 12/2004 |
| DE | 4309056 | 9/1994 |

(Continued)

OTHER PUBLICATIONS

International Search Report and Written Opinion mailed Jun. 9, 2006 for PCT/US2005/032422.

(Continued)

*Primary Examiner* — Tarifur Chowdhury
*Assistant Examiner* — Jonathon Cook
(74) *Attorney, Agent, or Firm* — Dorsey & Whitney LLP

(57) ABSTRACT

A system and method for imaging of a sample, e.g., biological sample, are provided. In particular, at least one source electro-magnetic radiation forwarded to the sample and a reference may be generated. A plurality of detectors may be used, at least one of the detectors capable of detecting a signal associated with a combination of at least one first electro-magnetic radiation received from the sample and at least one second electro-magnetic radiation received from the reference. At least one particular detector may have a particular electrical integration time, and can receive at least a portion of the signal for a time duration which has a first portion with a first power level greater than a predetermined threshold and a second portion immediately preceding or following the first portion. The second portion may have a second power level that is less than the predetermined threshold, and extends for a time period which may be, e.g., approximately more than 10% of the particular electrical integration time.

56 Claims, 15 Drawing Sheets

(a)

(b)

(c)

U.S. PATENT DOCUMENTS

| | | | | |
|---|---|---|---|---|
| 4,631,498 | A | | 12/1986 | Cutler |
| 4,639,999 | A | | 2/1987 | Daniele |
| 4,650,327 | A | | 3/1987 | Ogi |
| 4,734,578 | A | | 3/1988 | Horikawa |
| 4,744,656 | A | | 5/1988 | Moran et al. |
| 4,751,706 | A | | 6/1988 | Rohde et al. |
| 4,763,977 | A | | 8/1988 | Kawasaki et al. |
| 4,770,492 | A | | 9/1988 | Levin et al. |
| 4,827,907 | A | | 5/1989 | Tashiro et al. |
| 4,834,111 | A | | 5/1989 | Khanna et al. |
| 4,868,834 | A | | 9/1989 | Fox et al. |
| 4,890,901 | A | | 1/1990 | Cross, Jr. |
| 4,905,169 | A | | 2/1990 | Buican et al. |
| 4,909,631 | A | | 3/1990 | Tan et al. |
| 4,925,302 | A | | 5/1990 | Cutler |
| 4,928,005 | A | | 5/1990 | Lefevre et al. |
| 4,940,328 | A | | 7/1990 | Hartman |
| 4,965,441 | A | | 10/1990 | Picard |
| 4,966,589 | A | | 10/1990 | Kaufman |
| 4,984,888 | A | | 1/1991 | Tobias et al. |
| 4,993,834 | A | | 2/1991 | Carlhoff et al. |
| 4,998,972 | A | | 3/1991 | Chin et al. |
| 5,039,193 | A | | 8/1991 | Snow et al. |
| 5,040,889 | A | | 8/1991 | Keane |
| 5,045,936 | A | | 9/1991 | Lobb et al. |
| 5,046,501 | A | | 9/1991 | Crilly |
| 5,065,331 | A | | 11/1991 | Vachon et al. |
| 5,085,496 | A | | 2/1992 | Yoshida et al. |
| 5,120,953 | A | | 6/1992 | Harris |
| 5,121,983 | A | | 6/1992 | Lee |
| 5,127,730 | A | | 7/1992 | Brelje et al. |
| 5,197,470 | A | | 3/1993 | Helfer et al. |
| 5,202,745 | A | | 4/1993 | Sorin et al. |
| 5,202,931 | A | | 4/1993 | Bacus et al. |
| 5,208,651 | A | | 5/1993 | Buican |
| 5,212,667 | A | | 5/1993 | Tomlinson et al. |
| 5,214,538 | A | | 5/1993 | Lobb |
| 5,217,456 | A | | 6/1993 | Narciso, Jr. |
| 5,241,364 | A | | 8/1993 | Kimura et al. |
| 5,248,876 | A | | 9/1993 | Kerstens et al. |
| 5,250,186 | A | * | 10/1993 | Dollinger et al. ..... 210/656 |
| 5,251,009 | A | | 10/1993 | Bruno |
| 5,262,644 | A | | 11/1993 | Maguire |
| 5,275,594 | A | | 1/1994 | Baker |
| 5,281,811 | A | | 1/1994 | Lewis |
| 5,283,795 | A | | 2/1994 | Fink |
| 5,291,885 | A | | 3/1994 | Taniji et al. |
| 5,293,872 | A | | 3/1994 | Alfano et al. |
| 5,293,873 | A | | 3/1994 | Fang |
| 5,302,025 | A | | 4/1994 | Kleinerman |
| 5,304,173 | A | | 4/1994 | Kittrell et al. |
| 5,304,810 | A | | 4/1994 | Amos |
| 5,305,759 | A | | 4/1994 | Kaneko et al. |
| 5,317,389 | A | | 5/1994 | Hochberg et al. |
| 5,318,024 | A | | 6/1994 | Kittrell et al. |
| 5,321,501 | A | | 6/1994 | Swanson et al. |
| 5,348,003 | A | * | 9/1994 | Caro ..... 600/310 |
| 5,353,790 | A | | 10/1994 | Jacques et al. |
| 5,383,467 | A | | 1/1995 | Auer et al. |
| 5,394,235 | A | * | 2/1995 | Takeuchi et al. ..... 356/73.1 |
| 5,404,415 | A | | 4/1995 | Mori et al. |
| 5,419,323 | A | | 5/1995 | Kittrell et al. |
| 5,424,827 | A | | 6/1995 | Horwitz et al. |
| 5,439,000 | A | | 8/1995 | Gunderson et al. |
| 5,441,053 | A | | 8/1995 | Lodder et al. |
| 5,450,203 | A | | 9/1995 | Penkethman |
| 5,454,807 | A | | 10/1995 | Lennox et al. |
| 5,459,325 | A | | 10/1995 | Hueton et al. |
| 5,459,570 | A | | 10/1995 | Swanson et al. |
| 5,465,147 | A | | 11/1995 | Swanson |
| 5,486,701 | A | | 1/1996 | Norton et al. |
| 5,491,524 | A | | 2/1996 | Hellmuth et al. |
| 5,491,552 | A | | 2/1996 | Knuttel |
| 5,522,004 | A | | 5/1996 | Djupsjobacka et al. |
| 5,526,338 | A | | 6/1996 | Hasman et al. |
| 5,555,087 | A | | 9/1996 | Miyagawa et al. |
| 5,562,100 | A | | 10/1996 | Kittrell et al. |
| 5,565,983 | A | | 10/1996 | Barnard et al. |
| 5,565,986 | A | | 10/1996 | Knuttel |
| 5,566,267 | A | | 10/1996 | Neuberger |
| 5,583,342 | A | | 12/1996 | Ichie |
| 5,590,660 | A | | 1/1997 | MacAulay et al. |
| 5,600,486 | A | | 2/1997 | Gal et al. |
| 5,601,087 | A | | 2/1997 | Gunderson et al. |
| 5,623,336 | A | | 4/1997 | Raab et al. |
| 5,635,830 | A | | 6/1997 | Itoh |
| 5,649,924 | A | | 7/1997 | Everett et al. |
| 5,697,373 | A | | 12/1997 | Richards-Kortum et al. |
| 5,698,397 | A | | 12/1997 | Zarling et al. |
| 5,710,630 | A | | 1/1998 | Essenpreis et al. |
| 5,719,399 | A | | 2/1998 | Alfano et al. |
| 5,730,731 | A | | 3/1998 | Mollenauer et al. |
| 5,735,276 | A | | 4/1998 | Lemelson |
| 5,748,318 | A | | 5/1998 | Maris et al. |
| 5,748,598 | A | | 5/1998 | Swanson et al. |
| 5,752,518 | A | | 5/1998 | McGee et al. |
| 5,784,352 | A | | 7/1998 | Swanson et al. |
| 5,785,651 | A | | 7/1998 | Baker et al. |
| 5,795,295 | A | | 8/1998 | Hellmuth et al. |
| 5,801,826 | A | | 9/1998 | Williams |
| 5,801,831 | A | | 9/1998 | Sargoytchev et al. |
| 5,803,082 | A | | 9/1998 | Stapleton et al. |
| 5,807,261 | A | | 9/1998 | Benaron et al. |
| 5,810,719 | A | | 9/1998 | Toida |
| 5,817,144 | A | | 10/1998 | Gregory et al. |
| 5,836,877 | A | | 11/1998 | Zavislan et al. |
| 5,840,023 | A | | 11/1998 | Oraevsky et al. |
| 5,842,995 | A | | 12/1998 | Mahadevan-Jansen et al. |
| 5,843,000 | A | | 12/1998 | Nishioka et al. |
| 5,843,052 | A | | 12/1998 | Benja-Athon |
| 5,847,827 | A | | 12/1998 | Fercher |
| 5,865,754 | A | | 2/1999 | Sevick-Muraca et al. |
| 5,867,268 | A | | 2/1999 | Gelikonov et al. |
| 5,871,449 | A | | 2/1999 | Brown |
| 5,877,856 | A | | 3/1999 | Fercher |
| 5,887,009 | A | | 3/1999 | Mandella et al. |
| 5,892,583 | A | | 4/1999 | Li |
| 5,910,839 | A | | 6/1999 | Erskine et al. |
| 5,912,764 | A | | 6/1999 | Togino |
| 5,920,373 | A | | 7/1999 | Bille |
| 5,920,390 | A | | 7/1999 | Farahi et al. |
| 5,921,926 | A | | 7/1999 | Rolland et al. |
| 5,926,592 | A | | 7/1999 | Harris et al. |
| 5,949,929 | A | | 9/1999 | Hamm |
| 5,951,482 | A | | 9/1999 | Winston et al. |
| 5,955,737 | A | | 9/1999 | Hallidy et al. |
| 5,956,355 | A | | 9/1999 | Swanson et al. |
| 5,968,064 | A | | 10/1999 | Selmon et al. |
| 5,975,697 | A | | 11/1999 | Podoleanu et al. |
| 5,983,125 | A | | 11/1999 | Alfano et al. |
| 5,987,346 | A | | 11/1999 | Benaron et al. |
| 5,991,697 | A | | 11/1999 | Nelson et al. |
| 5,994,690 | A | | 11/1999 | Kulkarni et al. |
| 5,995,223 | A | | 11/1999 | Power |
| 6,002,480 | A | | 12/1999 | Izatt et al. |
| 6,004,314 | A | | 12/1999 | Wei et al. |
| 6,006,128 | A | | 12/1999 | Izatt et al. |
| 6,007,996 | A | | 12/1999 | McNamara et al. |
| 6,010,449 | A | | 1/2000 | Selmon et al. |
| 6,016,197 | A | | 1/2000 | Krivoshlykov |
| 6,020,963 | A | | 2/2000 | Dimarzio et al. |
| 6,025,956 | A | | 2/2000 | Nagano et al. |
| 6,033,721 | A | | 3/2000 | Nassuphis |
| 6,037,579 | A | | 3/2000 | Chan et al. |
| 6,044,288 | A | | 3/2000 | Wake et al. |
| 6,045,511 | A | | 4/2000 | Ott et al. |
| 6,048,742 | A | | 4/2000 | Weyburne et al. |
| 6,053,613 | A | | 4/2000 | Wei et al. |
| 6,069,698 | A | | 5/2000 | Ozawa et al. |
| 6,078,047 | A | | 6/2000 | Mittleman et al. |
| 6,091,496 | A | | 7/2000 | Hill |
| 6,091,984 | A | | 7/2000 | Perelman et al. |
| 6,094,274 | A | | 7/2000 | Yokoi |
| 6,107,048 | A | | 8/2000 | Goldenring et al. |
| 6,111,645 | A | | 8/2000 | Tearney et al. |
| 6,117,128 | A | | 9/2000 | Gregory |
| 6,120,516 | A | | 9/2000 | Selmon et al. |

6,134,003 A 10/2000 Tearney et al.
6,134,010 A 10/2000 Zavislan
6,134,033 A 10/2000 Bergano et al.
6,141,577 A 10/2000 Rolland et al.
6,151,522 A 11/2000 Alfano et al.
6,159,445 A 12/2000 Klaveness et al.
6,160,826 A 12/2000 Swanson et al.
6,161,031 A 12/2000 Hochmann et al.
6,166,373 A 12/2000 Mao
6,174,291 B1 1/2001 McMahon et al.
6,175,669 B1 1/2001 Colston et al.
6,185,271 B1 2/2001 Kinsinger
6,191,862 B1 2/2001 Swanson et al.
6,193,676 B1 2/2001 Winston et al.
6,198,956 B1 3/2001 Dunne
6,201,989 B1 3/2001 Whitehead et al.
6,208,415 B1 3/2001 De Boer et al.
6,208,887 B1 3/2001 Clarke
6,245,026 B1 6/2001 Campbell et al.
6,249,349 B1 6/2001 Lauer
6,249,381 B1 6/2001 Suganuma
6,249,630 B1 6/2001 Stock et al.
6,263,234 B1 7/2001 Engelhardt et al.
6,272,376 B1 8/2001 Marcu et al.
6,282,011 B1 8/2001 Tearney et al.
6,297,018 B1 10/2001 French et al.
6,301,048 B1 10/2001 Cao et al.
6,308,092 B1 10/2001 Hoyns
6,324,419 B1 11/2001 Guzelsu et al.
6,341,036 B1 1/2002 Tearney et al.
6,353,693 B1 3/2002 Kano et al.
6,374,128 B1 4/2002 Toida et al.
6,377,349 B1 4/2002 Fercher
6,384,915 B1 5/2002 Everett et al.
6,393,312 B1 5/2002 Hoyns
6,394,964 B1 5/2002 Sievert, Jr. et al.
6,396,941 B1 5/2002 Bacus et al.
6,421,164 B2 7/2002 Tearney et al.
6,437,867 B2 8/2002 Zeylikovich et al.
6,441,892 B2 8/2002 Xiao et al.
6,441,959 B1 8/2002 Yang et al.
6,445,485 B1 9/2002 Frigo et al.
6,445,939 B1 9/2002 Swanson et al.
6,445,944 B1 9/2002 Ostrovsky
6,463,313 B1 10/2002 Winston et al.
6,469,846 B2 10/2002 Ebizuka et al.
6,475,159 B1 11/2002 Casscells et al.
6,475,210 B1 11/2002 Phelps et al.
6,477,403 B1 11/2002 Eguchi et al.
6,485,413 B1 11/2002 Boppart et al.
6,485,482 B1 11/2002 Belef
6,501,551 B1 12/2002 Tearney et al.
6,516,014 B1 2/2003 Sellin et al.
6,517,532 B1 2/2003 Altshuler et al.
6,538,817 B1 3/2003 Farmer et al.
6,540,391 B2 4/2003 Lanzetta et al.
6,549,801 B1 4/2003 Chen et al.
6,552,796 B2 4/2003 Magnin et al.
6,556,305 B1 * 4/2003 Aziz et al. ..... 356/512
6,556,853 B1 4/2003 Cabib et al.
6,558,324 B1 5/2003 Von Behren et al.
6,564,087 B1 5/2003 Pitris et al.
6,564,089 B2 5/2003 Izatt et al.
6,567,585 B2 5/2003 Harris
6,593,101 B2 7/2003 Richards-Kortum et al.
6,611,833 B1 8/2003 Johnson et al.
6,615,071 B1 9/2003 Casscells, III et al.
6,622,732 B2 9/2003 Constantz
6,654,127 B2 11/2003 Everett et al.
6,657,730 B2 12/2003 Pfau et al.
6,658,278 B2 12/2003 Gruhl
6,680,780 B1 1/2004 Fee
6,685,885 B2 2/2004 Nolte et al.
6,687,007 B1 2/2004 Meigs
6,687,010 B1 2/2004 Horii et al.
6,692,430 B2 2/2004 Adler
6,701,181 B2 3/2004 Tang et al.
6,721,094 B1 4/2004 Sinclair et al.
6,738,144 B1 5/2004 Dogariu et al.
6,757,467 B1 6/2004 Rogers
6,806,963 B1 10/2004 Wälti et al.
6,816,743 B2 11/2004 Moreno et al.
6,831,781 B2 12/2004 Tearney et al.
6,839,496 B1 1/2005 Mills et al.
6,882,432 B2 4/2005 Deck
6,900,899 B2 5/2005 Nevis
6,909,105 B1 6/2005 Heintzmann et al.
6,949,072 B2 9/2005 Furnish et al.
6,961,123 B1 11/2005 Wang et al.
6,980,299 B1 12/2005 de Boer
6,996,549 B2 2/2006 Zhang et al.
7,006,231 B2 2/2006 Ostrovsky et al.
7,006,232 B2 2/2006 Rollins et al.
7,019,838 B2 3/2006 Izatt et al.
7,027,633 B2 4/2006 Foran et al.
7,061,622 B2 6/2006 Rollins et al.
7,072,047 B2 7/2006 Westphal et al.
7,075,658 B2 7/2006 Izatt et al.
7,099,358 B1 8/2006 Chong et al.
7,113,288 B2 9/2006 Fercher
7,113,625 B2 9/2006 Watson et al.
7,130,320 B2 10/2006 Tobiason et al.
7,139,598 B2 11/2006 Hull et al.
7,142,835 B2 11/2006 Paulus
7,148,970 B2 12/2006 De Boer
7,177,027 B2 2/2007 Hirasawa et al.
7,190,464 B2 3/2007 Alphonse
7,230,708 B2 6/2007 Lapotko et al.
7,236,637 B2 6/2007 Sirohey et al.
7,242,480 B2 7/2007 Alphonse
7,267,494 B2 9/2007 Deng et al.
7,272,252 B2 9/2007 De La Torre-Bueno et al.
7,304,798 B2 12/2007 Izumi et al.
7,330,270 B2 2/2008 O'Hara et al.
7,336,366 B2 2/2008 Choma et al.
7,342,659 B2 3/2008 Horn et al.
7,355,716 B2 4/2008 De Boer et al.
7,355,721 B2 4/2008 Quadling et al.
7,359,062 B2 4/2008 Chen et al.
7,366,376 B2 4/2008 Shishkov et al.
7,382,809 B2 6/2008 Chong et al.
7,391,520 B2 6/2008 Zhou et al.
7,458,683 B2 12/2008 Chernyak et al.
7,530,948 B2 5/2009 Seibel et al.
7,539,530 B2 5/2009 Caplan et al.
7,609,391 B2 10/2009 Betzig
7,630,083 B2 12/2009 de Boer et al.
7,643,152 B2 1/2010 de Boer et al.
7,643,153 B2 1/2010 de Boer et al.
7,646,905 B2 1/2010 Guittet et al.
7,649,160 B2 1/2010 Colomb et al.
7,664,300 B2 2/2010 Lange et al.
7,733,497 B2 6/2010 Yun et al.
7,782,464 B2 8/2010 Mujat et al.
7,805,034 B2 9/2010 Kato et al.
2001/0036002 A1 11/2001 Tearney et al.
2001/0047137 A1 11/2001 Moreno et al.
2002/0016533 A1 2/2002 Marchitto et al.
2002/0024015 A1 2/2002 Hoffmann et al.
2002/0048025 A1 4/2002 Takaoka
2002/0048026 A1 4/2002 Isshiki et al.
2002/0052547 A1 5/2002 Toida
2002/0057431 A1 5/2002 Fateley et al.
2002/0085209 A1 7/2002 Mittleman et al.
2002/0086347 A1 7/2002 Johnson et al.
2002/0091322 A1 7/2002 Chaiken et al.
2002/0109851 A1 8/2002 Deck
2002/0122182 A1 9/2002 Everett et al.
2002/0122246 A1 9/2002 Tearney et al.
2002/0140942 A1 10/2002 Fee et al.
2002/0158211 A1 10/2002 Gillispie
2002/0161357 A1 10/2002 Rox et al.
2002/0163622 A1 11/2002 Magnin et al.
2002/0168158 A1 11/2002 Furusawa et al.
2002/0183623 A1 12/2002 Tang et al.
2002/0196446 A1 12/2002 Roth et al.
2002/0198457 A1 12/2002 Tearney et al.
2003/0001071 A1 1/2003 Mandella et al.

| | | | |
|---|---|---|---|
| 2003/0013973 | A1 | 1/2003 | Georgakoudi et al. |
| 2003/0023153 | A1 | 1/2003 | Izatt et al. |
| 2003/0026735 | A1 | 2/2003 | Nolte et al. |
| 2003/0028114 | A1 | 2/2003 | Casscells, III et al. |
| 2003/0030816 | A1 | 2/2003 | Eom et al. |
| 2003/0043381 | A1 | 3/2003 | Fercher |
| 2003/0053673 | A1 | 3/2003 | Dewaele et al. |
| 2003/0067607 | A1 | 4/2003 | Wolleschensky et al. |
| 2003/0082105 | A1 | 5/2003 | Fischman et al. |
| 2003/0097048 | A1 | 5/2003 | Ryan et al. |
| 2003/0108911 | A1 | 6/2003 | Klimant et al. |
| 2003/0120137 | A1 | 6/2003 | Pawluczyk |
| 2003/0135101 | A1 | 7/2003 | Webler |
| 2003/0137669 | A1 | 7/2003 | Rollins et al. |
| 2003/0165263 | A1 | 9/2003 | Hamer et al. |
| 2003/0171691 | A1 | 9/2003 | Casscells, III et al. |
| 2003/0174339 | A1 | 9/2003 | Feldchtein et al. |
| 2003/0220749 | A1 | 11/2003 | Chen et al. |
| 2003/0236443 | A1 | 12/2003 | Cespedes et al. |
| 2004/0002650 | A1 | 1/2004 | Mandrusov et al. |
| 2004/0039298 | A1 | 2/2004 | Abreu |
| 2004/0054268 | A1 | 3/2004 | Esenaliev et al. |
| 2004/0072200 | A1 | 4/2004 | Rigler et al. |
| 2004/0075841 | A1 | 4/2004 | Van Neste et al. |
| 2004/0076940 | A1 | 4/2004 | Alexander et al. |
| 2004/0077949 | A1 | 4/2004 | Blofgett et al. |
| 2004/0085540 | A1 | 5/2004 | Lapotko et al. |
| 2004/0110206 | A1 | 6/2004 | Wong et al. |
| 2004/0126048 | A1 | 7/2004 | Dave et al. |
| 2004/0126120 | A1 | 7/2004 | Cohen et al. |
| 2004/0150829 | A1 | 8/2004 | Koch et al. |
| 2004/0150830 | A1 | 8/2004 | Chan |
| 2004/0152989 | A1 | 8/2004 | Puttappa et al. |
| 2004/0165184 | A1 | 8/2004 | Mizuno |
| 2004/0166593 | A1 | 8/2004 | Nolte et al. |
| 2004/0189999 | A1 | 9/2004 | De Groot et al. |
| 2004/0239938 | A1 | 12/2004 | Izatt et al. |
| 2004/0246490 | A1 | 12/2004 | Wang |
| 2004/0246583 | A1 | 12/2004 | Mueller et al. |
| 2004/0254474 | A1 | 12/2004 | Seibel et al. |
| 2004/0263843 | A1 | 12/2004 | Knopp et al. |
| 2005/0018133 | A1 | 1/2005 | Huang et al. |
| 2005/0018201 | A1 | 1/2005 | de Boer et al. |
| 2005/0035295 | A1 | 2/2005 | Bouma et al. |
| 2005/0036150 | A1 | 2/2005 | Izatt et al. |
| 2005/0046837 | A1 | 3/2005 | Izumi et al. |
| 2005/0057680 | A1* | 3/2005 | Agan ..... 348/362 |
| 2005/0057756 | A1 | 3/2005 | Fang-Yen et al. |
| 2005/0059894 | A1 | 3/2005 | Zeng et al. |
| 2005/0065421 | A1 | 3/2005 | Burckhardt et al. |
| 2005/0119567 | A1 | 6/2005 | Choi et al. |
| 2005/0128488 | A1 | 6/2005 | Yelin et al. |
| 2005/0165303 | A1 | 7/2005 | Kleen et al. |
| 2005/0171438 | A1 | 8/2005 | Chen et al. |
| 2005/0190372 | A1 | 9/2005 | Dogariu et al. |
| 2005/0254061 | A1 | 11/2005 | Alphonse et al. |
| 2006/0033923 | A1 | 2/2006 | Hirasawa et al. |
| 2006/0093276 | A1 | 5/2006 | Bouma et al. |
| 2006/0103850 | A1 | 5/2006 | Alphonse et al. |
| 2006/0146339 | A1 | 7/2006 | Fujita |
| 2006/0164639 | A1 | 7/2006 | Horn et al. |
| 2006/0171503 | A1 | 8/2006 | O'Hara et al. |
| 2006/0184048 | A1 | 8/2006 | Saadat et al. |
| 2006/0193352 | A1 | 8/2006 | Chong et al. |
| 2006/0244973 | A1 | 11/2006 | Yun et al. |
| 2007/0019208 | A1 | 1/2007 | Toida et al. |
| 2007/0038040 | A1 | 2/2007 | Cense et al. |
| 2007/0070496 | A1 | 3/2007 | Gweon et al. |
| 2007/0076217 | A1 | 4/2007 | Baker et al. |
| 2007/0086013 | A1 | 4/2007 | De Lega et al. |
| 2007/0086017 | A1 | 4/2007 | Buckland et al. |
| 2007/0091317 | A1 | 4/2007 | Freischlad et al. |
| 2007/0133002 | A1 | 6/2007 | Wax et al. |
| 2007/0188855 | A1 | 8/2007 | Shishkov et al. |
| 2007/0223006 | A1 | 9/2007 | Tearney et al. |
| 2007/0236700 | A1 | 10/2007 | Yun et al. |
| 2007/0258094 | A1 | 11/2007 | Izatt et al. |
| 2007/0291277 | A1 | 12/2007 | Everett et al. |
| 2008/0002197 | A1 | 1/2008 | Sun et al. |
| 2008/0007734 | A1 | 1/2008 | Park et al. |
| 2008/0049220 | A1 | 2/2008 | Izzia et al. |
| 2008/0094613 | A1 | 4/2008 | de Boer et al. |
| 2008/0094637 | A1 | 4/2008 | de Boer et al. |
| 2008/0097225 | A1 | 4/2008 | Tearney et al. |
| 2008/0097709 | A1 | 4/2008 | de Boer et al. |
| 2008/0100837 | A1 | 5/2008 | de Boer et al. |
| 2008/0152353 | A1 | 6/2008 | de Boer et al. |
| 2008/0154090 | A1 | 6/2008 | Hashimshony |
| 2008/0204762 | A1 | 8/2008 | Izatt et al. |
| 2008/0265130 | A1 | 10/2008 | Colomb et al. |
| 2008/0308730 | A1 | 12/2008 | Vizi et al. |
| 2009/0011948 | A1 | 1/2009 | Uniu et al. |
| 2009/0196477 | A1 | 8/2009 | Cense et al. |
| 2009/0273777 | A1 | 11/2009 | Yun et al. |
| 2009/0290156 | A1 | 11/2009 | Popescu et al. |
| 2010/0086251 | A1 | 4/2010 | Xu et al. |
| 2010/0094576 | A1 | 4/2010 | de Boer et al. |
| 2010/0150467 | A1 | 6/2010 | Zhao et al. |

FOREIGN PATENT DOCUMENTS

| | | |
|---|---|---|
| DE | 19542955 | 5/1997 |
| DE | 10351319 | 6/2005 |
| EP | 0110201 | 6/1984 |
| EP | 0617286 | 2/1994 |
| EP | 0728440 | 8/1996 |
| EP | 0251062 | 1/1998 |
| EP | 1324051 | 7/2003 |
| EP | 1426799 | 6/2004 |
| FR | 2738343 | 8/1995 |
| GB | 2209221 | 5/1989 |
| GB | 2298054 | 8/1996 |
| JP | 6073405 | 4/1985 |
| JP | 20040056907 | 2/1992 |
| JP | 4135550 | 5/1992 |
| JP | 4135551 | 5/1992 |
| JP | 5509417 | 11/1993 |
| JP | 02214127 | 7/2002 |
| JP | 20030035659 | 2/2003 |
| JP | 2004037165 | 2/2004 |
| JP | 2007271761 | 10/2007 |
| WO | 7900841 | 10/1979 |
| WO | 9201966 | 2/1992 |
| WO | 9216865 | 10/1992 |
| WO | WO 9219930 | 11/1992 |
| WO | WO 9303672 | 3/1993 |
| WO | 9216865 | 10/1993 |
| WO | WO 9533971 | 12/1995 |
| WO | 2298054 | 8/1996 |
| WO | WO 9732182 | 9/1997 |
| WO | 9800057 | 1/1998 |
| WO | WO 9814132 | 4/1998 |
| WO | WO 9835203 | 8/1998 |
| WO | 9848846 | 11/1998 |
| WO | WO 9848838 | 11/1998 |
| WO | 9944089 | 2/1999 |
| WO | WO 9944089 | 9/1999 |
| WO | WO 9957507 | 11/1999 |
| WO | WO 0058766 | 10/2000 |
| WO | 0101111 | 1/2001 |
| WO | 0127679 | 4/2001 |
| WO | WO 0138820 | 5/2001 |
| WO | WO 0142735 | 6/2001 |
| WO | 0237075 | 5/2002 |
| WO | WO 0236015 | 5/2002 |
| WO | WO 0238040 | 5/2002 |
| WO | 02053050 | 7/2002 |
| WO | WO 02054027 | 7/2002 |
| WO | 02084263 | 10/2002 |
| WO | WO 03020119 | 3/2003 |
| WO | 03046495 | 6/2003 |
| WO | 03046636 | 6/2003 |
| WO | 03062802 | 7/2003 |
| WO | WO 03062802 | 7/2003 |
| WO | 03105678 | 12/2003 |
| WO | 2004057266 | 7/2004 |
| WO | WO 2004105598 | 12/2004 |
| WO | 2005047813 | 5/2005 |
| WO | 2005082225 | 9/2005 |

| | | |
|---|---|---|
| WO | 2006004743 | 1/2006 |
| WO | 2006039091 | 3/2006 |
| WO | 2006038876 | 4/2006 |
| WO | 2006059109 | 6/2006 |
| WO | 2006124860 | 11/2006 |
| WO | 2007028531 | 3/2007 |
| WO | 2007083138 | 7/2007 |
| WO | 2007084995 | 7/2007 |

OTHER PUBLICATIONS

Notification of Transmittal of the International Preliminary Report of Patentability mailed Dec. 21, 2006 for PCT/US2005/032422.
Amendment under Article 34 and reply to PCT Written Opinion mailed Sep. 7, 2006 for PCT/US2005/032422.
Liptak David C. et al., (2007) "On the Development of a Confocal Rayleigh-Brillouin Microscope" *American Institute of Physics* vol. 78, 016106.
Office Action mailed Oct. 1, 2008 for U.S. Appl. No. 11/955,986.
Invitation of Pay Additional Fees mailed Aug. 7, 2008 for International Application No. PCT/US2008/062354.
Invitation of Pay Additional Fees mailed Jul. 20, 2008 for International Application No. PCT/US2007/081982.
International Search Report and Written Opinion mailed Mar. 7, 2006 for PCT/US2005/035711.
International Search Report and Written Opinion mailed Jul. 18, 2008 for PCT/US2008/057533.
Aizu, Y et al. (1991) "Bio-Speckle Phenomena and Their Application to the Evaluation of Blood Flow" Optics and Laser Technology, vol. 23, No. 4, Aug. 1, 1991.
Richards G.J. et al. (1997) "Laser Speckle Contrast Analysis (LASCA): A Technique for Measuring Capillary Blood Flow Using the First Order Statistics of Laser Speckle Patterns" Apr. 2, 1997.
Gonick, Maria M., et al (2002) "Visualization of Blood Microcirculation Parameters in Human Tissues by Time Integrated Dynamic Speckles Analysis" vol. 972, No. 1, Oct. 1, 2002.
International Search Report and Written Opinion mailed Jul. 4, 2008 for PCT/US2008/051432.
Jonathan, Enock (2005) "Dual Reference Arm Low-Coherence Interferometer-Based Reflectometer For Optical Coherence Tomography (OCT) Application" *Optics Communications* vol. 252.
Motaghian Nezam, S.M.R. (2007) "increased Ranging Depth in optical Frequency Domain Imaging by Frequency Encoding" *Optics Letters*, vol. 32, No. 19, Oct. 1, 2007.
Office Action dated Jun. 30, 2008 for U.S. Appl. No. 11/670,058.
Office Action dated Jul. 7, 2008 for U.S. Appl. No. 10/551,735.
Australian Examiner's Report mailed May 27, 2008 for Australian patent application No. 2003210669.
Notice of Allowance mailed Jun. 4, 2008 for U.S. Appl. No. 11/174,425.
European communication dated May 15, 2008 for European patent application No. 05819917.5.
International Search Report and Written Opinion mailed Jun. 10, 2008 for PCT/US2008/051335.
Oh. W.Y. et al (2006) "Ultrahigh-Speed Optical Frequency Domain Imaging and Application to laser Ablation Monitoring" *Applied Physics Letters*, vol. 88.
Office Action dated Aug. 21, 2008 for U.S. Appl. No. 11/505,700.
Sticker, Markus (2002) En Face Imaging of Single Cell layers by Differential Phase-Contrast Optical Coherence Microscopy) *Optics Letters*, col. 27, No. 13, Jul. 1, 2002.
International Search Report and Written Opinion dated Jul. 17, 2008 for International Application No. PCT/US2008/057450.
International Search Report and Written Opinion dated Aug. 11, 2008 for International Application No. PCT/US2008/058703.
US National Library of Medicine (NLM), Bethesda, MD, US; Oct. 2007 (Oct. 2007), "Abstracts of the 19th Annual Symposium of Transcatheter Cardiovascular Therapeutics, Oct. 20-25, 2007, Washington, DC, USA."
International Search Report and Written Opinion dated May 26, 2008 for International Application No. PCT/US2008/051404.
Office Action dated Aug. 25, 2008 for U.S. Appl. No. 11/264,655.
Office Action dated Sep. 11, 2008 for U.S. Appl. No. 11/624,334.
Office Action dated Aug. 21, 2008 for U.S. Appl. No. 11/956,079.
Gelikono, V. M. et al. Oct. 1, 2004 "Two-Wavelength Optical Coherence Tomography" Radio physics and Quantum Electronics, Kluwer Academic Publishers-Consultants. vol. 47, No. 10-1.
International Search Report and Written Opinion for PCT/US2007/081982 dated Oct. 19, 2007.
Database Compendex Engineering Information, Inc., New York, NY, US; Mar. 5, 2007, Yelin, Dvir et al: "Spectral-Domain Spectrally-Encoded Endoscopy".
Database Biosis Biosciences Information Service, Philadelphia, PA, US; Oct. 2006, Yelin D. et al: "Three-Dimensional Miniature Endoscopy".
International Search Report and Written Opinion mailed Mar. 14, 2005 for PCT/US2004/018045.
Notification of the international Preliminary Report on Patentability mailed Oct. 21, 2005.
Shim M.G. et al., "Study of Fiber-Optic Probes For In vivo Medical Raman Spectroscopy" Applied Spectroscopy. vol. 53, No. 6, Jun. 1999.
Bingid U. et al., "Fibre-Optic Laser-Assisted Infrared Tumour Diagnostics (FLAIR); Infrared Tomour Diagnostics" Journal of Physics D. Applied Physics, vol. 38, No. 15, Aug. 7, 2005.
Jun Zhang et al. "Full Range Polarization-Sensitive Fourier Domain Optical Coherence Tomography" Optics Express, vol. 12, No. 24. Nov. 29, 2004.
Yonghua et al., "Real-Time Phase-Resolved Functional Optical Hilbert Transformation" Optics Letters, vol. 27, No. 2, Jan. 15, 2002.
Siavash et al., "Self-Referenced Doppler Optical Coherence Tomography" Optics Letters, vol. 27, No. 23, Dec. 1, 2002.
International Search Report and Written Opinion dated Dec. 20, 2004 for PCT/US04/10152.
Notification Concerning Transmittal of International Preliminary Report on Patentability dated Oct. 13, 2005 for PCT/US04/10152.
International Search Report and Written Opinion dated Mar. 23, 2006 for PCT/US2005/042408.
International Preliminary Report on Patentability dated Jun. 7, 2007 for PCT/US2005/042408.
International Search Report and Written Opinion dated Feb. 28, 2007 for International Application No. PCT/US2006/038277.
International Search Report and Written Opinion dated Jan. 30, 2009 for International Application No. PCT/US2008/081834.
Fox, J.A. et al; "A New Galvanometric Scanner for Rapid tuning of C02 Lasers" New York, IEEE, US vol. Apr. 7, 1991.
Motaghian Nezam, S.M. et al: "High-speed Wavelength-Swept Semiconductor laser using a Diffrection Grating and a Polygon Scanner in Littro Configuration" *Optical Fiber Communication and the National Fiber Optic Engineers Conference* Mar. 29, 2007.
International Search Report and Written Opinion dated Feb. 2, 2009 for International Application No. PCT/US2008/071786.
Bilenca A et al: "The Role of Amplitude and phase in Fluorescence Coherence Imaging: From Wide Filed to Nanometer Depth Profiling", *Optics IEEE*, May 5, 2007.
Inoue, Yusuke et al: "Varible Phase-Contrast Fluorescence Spectrometry for Fluorescently Strained Cells", *Applied Physics Letters*, Sep. 18, 2006.
Bernet, S et al: "Quantitative Imaging of Complex Samples by Spiral Phase Contrast Microscopy", *Optics Express*, May 9, 2006.
International Search Report and Written Opinion dated Jan. 15, 2009 for International Application No. PCT/US2008/074863.
Office Action dated Feb. 17, 2009 for U.S. Appl. No. 11/211,483.
Notice of Reasons for Rejection mailed Dec. 2, 2008 for Japanese patent application No. 2000-533782.
International Search Report and Written Opinion dated Feb. 24, 2009 for PCT/US2008/076447.
European Official Action dated Dec. 2, 2008 for EP 07718117.0.
Barfuss et al (1989) "Modified Optical Frequency Domain Reflectometry with High spatial Resolution for Components of integrated optic Systems", Journal of Lightwave Technology, IEEE vol. 7., No. 1.
Yun et al., (2004) "Removing the Depth-Degeneracy in Optical Frequency Domain Imaging with Frequency Shifting", Optics Express, vol. 12, No. 20.
International Search Report and Written Opinion dated Jun. 10, 2009 for PCT/US08/075456.

European Search Report issued May 5, 2009 for European Application No. 01991471.2.
Motz, J.T. et al: "Spectral-and Frequency-Encoded Fluorescence Imaging" Optics Letters, OSA, Optical Society of America, Washington, DC, US, vol. 30, No. 20, Oct. 15, 2005, pp. 2760-2762.
Japanese Notice of Reasons for Rejection dated Jul. 14, 2009 for Japanese Patent application No. 2006-503161.
Office Action dated Aug. 18, 2009 for U.S. Appl. No. 12/277,178.
Office Action dated Aug. 13, 2009 for U.S. Appl. No. 10/136,813.
Office Action dated Aug. 6, 2009 for U.S. Appl. No. 11/624,455.
Office Action dated May 15, 2009 for U.S. Appl. No. 11/537,123.
Office Action dated Apr. 17, 2009 for U.S. Appl. No. 11/537,343.
Office Action dated Apr. 15, 2009 for U.S. Appl. No. 12/205,775.
Office Action dated Dec. 9, 2008 for U.S. Appl. No. 09/709,162.
Office Action dated Dec. 23, 2008 for U.S. Appl. No. 11/780,261.
Office Action dated Jan. 9, 2010 for U.S. Appl. No. 11/624,455.
Office Action dated Feb. 18, 2009 for U.S. Appl. No. 11/285,301.
Beddow et al, (May 2002) "Improved Performance Interferomater Designs for Optical Coherence Tomography", IEEE Optical Fiber Sensors Conference, pp. 527-530.
Yaqoob et al., (Jun. 2002) "High-Speed Wavelength-Multiplexed Fiber-Optic Sensors for Biomedicine," Sensors Proceedings of the IEEE, pp. 325-330.
Office Action dated Feb. 18, 2009 for U.S. Appl. No. 11/697,012.
Zhang et al, (Sep. 2004), "Fourier Domain Functional Optical Coherence Tomography", Saratov Fall Meeting 2004, pp. 8-14.
Office Action dated Feb. 23, 2009 for U.S. Appl. No. 11/956,129.
Office Action dated Mar. 16, 2009 for U.S. Appl. No. 11/621,694.
Office Action dated Oct. 1, 2009 for U.S. Appl. No. 11/677,278.
Office Action dated Oct. 6, 2009 for U.S. Appl. No. 12/015,642.
Lin, Stollen et al.,(1977) " A AW Tunable Near-infrared (1.085-1. 175-um) Raman Oscillator," Optics Letters, vol. 1, 96.
Summons to attend Oral Proceedings dated Oct. 9, 2009 for European patent application No. 06813365.1.
Office Action dated Dec. 15, 2009 for U.S. Appl. No. 11/549,397.
R. Haggitt et al., "Barrett's Esophagus Correlation Between Mucin Histochemistry, Flow Cytometry, and Histological Diagnosis for Predicting Increased Cancer Risk," Apr. 1988, American Journal of Pathology, vol. 131, No. 1, pp. 53-61.
R.H. Hardwick et al., (1995) "c-erbB-2 Overexpression in the Dysplasia/Carcinoma Sequence of Barrett's Oesophagus," Journal of Clinical Pathology, vol. 48, No. 2, pp. 129-132.
W. Polkowski et al, (1998) "Clinical Decision making in Barrett's Oesophagus can be supported by Computerized Immunoquantitation and Morphometry of Features Associated with Proliferation and Differentiation," Journal of pathology, vol. 184, pp. 161-168.
J.R. Turner et al., MN Antigen Expression in Normal Preneoplastic, and Neoplastic Esophagus: A Clinicopathological Study of a New Cancer-Associated Biomarker,: Jun. 1997, Human Pathology, vol. 28, No. 6, pp. 740-744.
D.J. Bowery et al., (1999) "Patterns of Gastritis in Patients with Gastro-Oesophageal Reflux Disease,", Gut, vol, 45, pp. 798-803.
O'Reich et al., (2000) "Expression of Oestrogen and Progesterone Receptors in Low-Grade Endometrial Stromal Sarcomas,", British Journal of Cancer, vol. 82, No. 5, pp. 1030-1034.
M.I. Canto et al., (1999) "Vital Staining and Barrett's Esophagus," Gastrointestinal Endoscopy, vol. 49, No. 3, Part 2, pp. S12-S16.
S. Jackle et al., (2000) "In Vivo Endoscopic Optical Coherence Tomography of the Human Gastrointestinal Tract—Toward Optical Biopsy," Encoscopy, vol. 32, No. 10, pp. 743-749.
E. Montgomery, et al., "Reproducibility of the Diagnosis of Dysplasia in Barrett Esophagus: A Reaffirmation," Apr. 2001, Human Pathology, vol. 32, No. 4, pp. 368-378.
H. Geddert et al., "Expression of Cyclin B1 in the Metaplasia-Dysphasia-Carcinoma Sequence of Barrett Esophagus," Jan. 2002, Cancer, vol. 94, No. 1, pp. 212-2180.
P. Pfau et al., (2003) "Criteria for the Diagnosis of Dysphasia by Endoscopic Optical Coherence Tomography," Gastrointestinal Endoscopy, vol. 58, No. 2, pp. 196-2002.
R. Kiesslich et al., (2004) "Confocal Laser Endoscopy for Diagnosing Intraepithelial Neoplasias and Colorectal Cancer in Vivo," Gastroenterology, vol. 127, No. 3, pp. 706-713.
X. Qi et al., (2004) "Computer Aided Diagnosis of Dysphasia in Barrett's Esophagus Using Endoscopic Optical Coherence Tomography," SPIE, Coherence Domain Optical Methods and Optical Coherence Tomography in Biomedicine VIII. Proc. of Conference on., vol. 5316, pp. 33-40.
Seltzer et al., (1991) "160 nm Continuous Tuning of a MQW Laser in an External Cavity Across the Entire 1.3 μm Communications Window," Electronics Letters, vol. 27, pp. 95-96.
Office Action dated Jan. 25, 2010 for U.S. Appl. No. 11/537,048.
International Search Report dated Jan. 27, 2010 for PCT/US2009/050553.
International Search Report dated Jan. 27, 2010 for PCT/US2009/047988.
International Search Report dated Feb. 23, 2010 for U.S. Appl. No. 11/445,131.
Office Action dated Mar. 18, 2010 of U.S. Appl. No. 11/844,454.
Office Action dated Apr. 8, 2010 of U.S. Appl. No. 11/414,564.
Japanese Office Action dated Apr. 13, 2010 for Japanese Patent application No. 2007-515029.
International Search Report dated May 27, 2010 for PCT/US2009/063420.
Office Action dated May 28, 2010 for U.S. Appl. No. 12/015,642.
Office Action dated Jun. 2, 2010 for U.S. Appl. No. 12/112,205.
Office Action dated Jul. 7, 2010 for U.S. Appl. No. 11/624,277.
Montag Ethan D., "Parts of the Eye" online textbook for JIMG 774: Vision & Psycophysics, download on Jun. 23, 2010 from http://www.cis.rit.edu/people/faculty/montag/vandplite/pp./chap.8/ch8p3.html.
Office Action dated Jul. 16, 2010 for U.S. Appl. No. 11/445,990.
Office Action dated Jul. 20, 2010 for U.S. Appl. No. 11/625,135.
Office Action dated Aug. 5, 2010 for U.S. Appl. No. 11/623,852.
Chinese office action dated Aug. 4, 2010 for CN 200780005949.9.
Chinese office action dated Aug. 4, 2010 for CN 200780016266.3.
Zhang et al., "Full Range Polarization-Sensitive Fourier Domain Optical Coherence Tomography" Optics Express, Nov. 29, 2004, vol. 12, No. 24.
Office Action dated Aug. 27, 2010 for U.S. Appl. No. 11/569,790.
Office Action dated Aug. 31, 2010 for U.S. Appl. No. 11/677,278.
Office Action dated Sep. 3, 2010 for U.S. Appl. No. 12/139,314.
Yong Zhao et al: "Virtual Data Grid Middleware Services for Data-Intensive Science", Concurrency and Computation: Practice and Experience, Wiley, London, GB, Jan. 1, 2000, pp. 1-7, pp. 1532-0626.
Swan et al., "Toward Nanometer-Scale Resolution in Fluorescence Microscopy using Spectral Self-Inteference" IEEE Journal. Selected Topics in Quantum Electronics 9 (2) 2003, pp. 294-300.
Moiseev et al., "Spectral Self-Interfence Fluorescence Microscopy", J. Appl. Phys. 96 (9) 2004, pp. 5311-5315.
Hendrik Verschueren, "Interference Reflection Microscopy in Cell Biology", J. Cell Sci. 75, 1985, pp. 289-301.
Park et al., "Diffraction Phase and Fluorescence Microscopy", Opt. Expr. 14 (18) 2006, pp. 8263-8268.
Swan et al. "High Resolution Spectral Self-Interference Fluorescence Microscopy", Proc. SPIE 4621, 2002, pp. 77-85.
Sanchez et al., "Near-Field Fluorscence Microscopy Based on Two-Photon Excvitation with Metal Tips", Phys. Rev. Lett. 82 (20) 1999, pp. 4014-4017.
Wojtkowski, Maciej, Ph.D. "Three-Dimensional Retinal Imaging with High-Speed Ultrahigh-Resolution Optical Coherence Tomography" Ophthalmology, Oct. 2005 112(10): 1734-1746.
Vaughan, J.M. et al., "Brillouin Scattering, Density and Elastic Properties of the Lens and Cornea of the Eye", Nature, vol. 284, Apr. 3, 1980, pp. 489-491.
Hess, S.T. et al. "Ultra-high Resolution Imaging by Fluorescence Photoactivation Localization Microscopy" Biophysical Journal vol. 91, Dec. 2006, 4258-4272.
Fernandez-Suarez, M. et al., "Fluorescent Probes for Super-Resolution Imaging in Living Cells" Nature Reviews Molecular Cell Biology vol. 9, Dec. 2008.
"In vivo imaging of blood flow in human retinal vessels using color Doppler optical coherence tomography" Yazdanfar et al, Part of the SPIE Conference on Coherence Domain Methods in Biomedical Science and Clinical Applications III * San Jose, California * Jan. 1999 177 SPIE vol. 3598 * 0277-786X199/$ 10.00.*

Fujimoto et al., "High Resolution in Vivo Intra-Arterial Imaging with Optical Coherence Tomography", *Official Journal of the British Cardiac Society*, vol. 82, pp. 128-133 Heart, 1999.
D. Huang et al., "Optical Coherence Tomography", *Science*, vol. 254, pp. 1178-1181, Nov. 1991.
Tearney et al., "High-Speed Phase -and Group Delay Scanning with a Grating Based Phase Control Line", *Optics Letters*, vol. 22, pp. 1811-1813, Dec. 1997.
Rollins, et al., "In Vivo Video Rate Optical Coherence Tomography", *Optics Express*, vol. 3, pp. 219-229, Sep. 1998.
Saxer, et al., High Speed Fiber-Based Polarization-Sensitive Optical Coherence Tomography of in Vivo Human Skin, *Optical Society of America*, vol. 25, pp. 1355-1357, Sep. 2000.
Oscar Eduardo Martinez, "3000 Times Grating Compress or Positive Group Velocity Dispersion", *IEEE*, vol. QE-23, pp. 59-64, Jan. 1987.
Kulkarni, et al., "Image Enhancement in Optical Coherence Tomography Using Deconvolution", *Electronics Letters*, vol. 33, pp. 1365-1367, Jul. 1997.
Bashkansky, et al., "Signal Processing for Improving Field Cross-Correlation Function in Optical Coherence Tomography", *Optics & Photonics News*, vol. 9, pp. 8137-8138, May 1998.
Yung et al., "Phase-Domain Processing of Optical Coherence Tomography Images", *Journal of Biomedical Optics*, vol. 4, pp. 125-136, Jan. 1999.
Tearney, et al., "In Vivo Endoscopic Optical Biopsy with Optical Coherence Tomography", *Science*, vol. 276, Jun. 1997.
W. Drexler et al. "In Vivo Ultrahigh-Resolution Optical Coherence Tomography", Opt. Lett. vol. 24, pp. 1221-1223, Sep. 1999.
Nicusor V. Iftimia et al., "A Portable, Low Coherence Interferometry Based Instrument for Fine Needle Aspiration Biopsy Guidance" Accepted to Review to Scientific Instruments, 2005.
Abbas, G.L., V.W.S. Chan et al., "Local-Oscillator Excess-Noise Suppression for Homodyne and Heterodyne-Detection", *Optics Letters*, vol. 8, pp. 419-421, Aug. 1982 issue.
Agrawall, G.P., "Population Pulsation and Nondegenerate 4-Wave Mixing in Semiconductor-Lasers and Amplifiers", *Journal Of The Optical Society Of America B-Optical Physics*, vol. 5, pp. 147-159, Jan. 1998.
Andretzky, P. et al., "Optical Coherence Tomography by Spectral Radar: Improvement of Signal-to-Noise Ration", *The International Society for Optical Enguneering*, USA, vol. 3915, 2000.
Ballif, J. et al., "Rapid and Scalable Scans at 21 m/s in optical Low-Coherence Reflectometry", *Optics Letters*, vol. 22, pp. 757-759, Jun. 1997.
Barfuss H. et al., "Modified Optical Frequency-Domain Reflectometry with High Spatial-Resolution for Components of Integrated Optics Systems", *Journal Of Lightwave technology*vol. 7, pp. 3-10, Jan. 1989.
Beaud, P. et al., "Optical Reflectometry with Micrometer Resolution for the Investigation of Integrated Optical-Devices", *Leee Journal of Quantum Electronics*, vol. 25, pp. 755-759, Apr. 1989.
Bauma, Brett et al., "Power-Efficient Nonreciprocal Interferometer and Linear-Scanning Fiber-Optic Catheter for Optical Coherence Tomography", *Optics Letters*, vol. 24, pp. 531-533, Apr. 1999.
Brinkmeyer, E., et al., "Efficient Algorithm for Non-Equidistant Interopolation of Sampled Data", *Electronics Letters*, vol. 28, p. 693, Mar. 1992.
Brinkmeyer, E. et al., "High-Resolution OCDR in Dispersive Wave-Guides", *Electronics Letters*, vol. 26, pp. 413-414, Mar. 1990.
Chinn, S.R. et al., "Optical Coherence Tomography Using a Frequency-Tunable Optical Source", *Optical Letters*, vol. 22, pp. 340-342, Mar. 1997.
Danielson, B.L. et al., "Absolute Optical Ranging Using Low Coherence Interferometry", *Applied Optics*, vol. 30, p. 2975, Jul. 1991.
Dorrer, C. et al., "Spectral Resolution and Sampling Issues in Fourier-Transform Spectral Interferometry", *Journal of the Optical Society of America B-Optical Physics*, vol. 17, pp. 1795-1802, Oct. 2000.
Dudley, J. M. et al., "Cross-Correlation Frequency Resolved Optical Gating Analysis of Broadband Continuum Generation in Photonic Crystal Fiber: Simulations and Experiments", *Optics Express*, vol. 10, p. 125, Oct. 2002.
Fercher, Adolf "Optical Coherence Tomography", *Journal of Biomedical Optics*, vol. 1, pp. 157-173, Apr. 1996.
Ferreira, L.A. et al., "Polarization-Intensive Fiberoptic White-Light Interferometry", *Optics Communications*, vol. 114, pp. 386-392, Feb. 1995.
Fujii, Yohji, "High-Isolation Polarization-Independent Optical Circulator", *Journal of Lightware Technology*, vol. 9, pp. 1239-1243, Oct. 1991.
Glance, B., "polarization Independent Coherent Optical Receiver", *Journal of Light wave Technology*, vol. LT-5, p. 274, Feb. 1987.
Glombitza, U., "Coherent Frequency-Domain Reflectometry for Characterization of Single-Mode Integrated-Optical Wave Guides", *Journal of Lightwave Technology*, vol. 11, 1377-1384, Aug. 1993.
Golubovic, B. et al., "Optical Frequency-Domain Reflectometry Using Rapid Wavelength Tuning of a Cr4+:Forsterite Laser", *Optics Letters*, vol. pp. 1704-1706, Nov. 1997.
Haberland, U. H. P. et al., "Chirp Optical Coherence Tomography of Layered Scattering Media", *Journal of Biomedical Optics*, vol. 3, pp. 259-266, Jul. 1998.
Hammer, Daniel X. et al., "Spectrally Resolved White-Light Interferometry for Measurement of Ocular Dispersion", *Journal of the Optical Society of America A-Optics Image Science and Vision*, vol. 16, pp. 2092-2102, Sep. 1999.
Harvey, K.C. et al., "External-Cavity Diode-Laser Using a Grazing-Incidence Diffraction Grating", *Optics Letters*, vol. 16, pp. 910-912, Jun. 1991.
Hausler, Gerd et al., "'Coherence Radar' and 'Spectral Radar' New Tools for Dermatological Diagnosis", *Journal of Biomedical Optics*, vol. 3, pp. 21-31, Jan. 1998.
Hee , Michael R. et al., "Polarization-Sensitive Low-Coherence Reflectometer for Birefringence Characterization and Ranging", *Journal of the Optical Society of America B* (*Optical Physics*), vol. 9, p. 903-908, Jun. 1992.
Hotate Kazuo et al., "Optical Coherence Domain Reflectometry by Synthesis of Coherence Function", *Journal of Lightwave Technology*, vol. 11, pp. 1701-1710, Oct. 1993.
Inoue, Kyo et al., "Nearly Degenerate 4-Wave-Mixing in a Traveling-Wave Semiconductor-Laser Amplifier", *Applied Physics Letters*, vol. 51, pp. 1051-1053, 1987.
Ivanov, A. P. et al., "New Method for High-Range Resolution Measurements of Light Scattering in Optically Dense Inhomogeneous Media", *Optics Letters*, vol. 1, pp. 226-228, Dec. 1977.
Ivanov, A. P. et al., "Interferometric Study of the Spatial Structure of Light-Scattering Medium", *Journal of Applied Spectroscopy*, vol. 28, pp. 518-525, 1978.
Kazovsky, L. G. et al., "Heterodyne Detection Through Rain, Snow, and Turbid Media: Effective Receiver Size at Optical Through Millimeter Wavelengths", *Applied Optics*, vol. 22, pp. 706-710, Mar. 1983.
Kersey, A. D. et al., "Adaptive Polarization Diversity Receiver Configuration for Coherent Optical Fiber Communications", *Electronics Letters*, vol. 25, pp. 275-277, Feb. 1989.
Kohlhaas, Andreas et al., "High-Resolution OCDR for Testing Integrated-Optical Waveguides: Dispersion-Corrupted Experimental Data Corrected by a Numerical Algorithm", *Journal of Lightwave Technology*, vol. 9, pp. 1493-1502, Nov. 1991.
Larkin, Kieran G., "Efficient Nonlinear Algorithm for Envelope Detection in White Light Interofeometry", *Journal of Optical Society of America A-Optics Image Science and Vision*, vol. 13, pp. 832-843, Apr. 1996.
Leitgeb, R. et al., "Spectral measurement of Absorption by Spectroscopic Frequency-Domain Optical Coherence Tomography", *Optics Letters*, vol. 25, pp. 820-822, Jun. 2000.
Lexer, F. et al., "Wavelength-Turning Interferometry of Introacular Distances", *Applied Optics*, vol. 36, pp. 6548-6553, Sep. 1997.
Mitsui, Takahisa, "Dynamic Range of Optical Reflectometry with Spectral Interferometry", *Japanese Journal of Applied Physics Part I—Regular Papers Short Notes & Review Papers*, vol. 38, pp. 6133-6137, 1999.
Naganuma, Kazunori et al., "Group-Delay Measurement Using the Fourier-Transform of an Interferometric Cross-Correlation Generated by White Light", *Optics Letters*, vol. 15, pp. 393-395, Apr. 1990.

Okoshi,Takanori, "Polarization-State Control Schemes for Heterodyne or Homodyne Optical Fiber Communications", *Journal of Lightwave Technology*, vol. LT-3, pp. 1232-1237, Dec. 1995.
Passy, R. et al., "Experimental and Theoretical Investigations of Coherent OFDR with Semiconductor-Laser Sources", *Journal of Lightwave Technology*, vol. 12, pp. 1622-1630, Sep. 1994.
Pololeanu, Adrian G., "Unbalanced Versus Balanced Operation in an Optical Coherence Tomography System", *Applied Optics*, vol. 39, pp. 173-182, Jan. 2000.
Price, J. H. V. et al., "Tunable, Femtosecond Pulse Source Operating in the Range 1.06-1.33 mu m Based on an Yb3+-doped Holey Fiber Amplifier", *Journal of the Optical Society of America B-Optical Physics*, vol. 19, pp. 1286-1294, Jun. 2002.
Schmitt, J. M. et al., "Measurement of Optical-Properties O Biological Tissues By Low-Coherence Reflectometry" *Applied Optics*, vol. 32, pp. 6032-6042, Oct. 1993.
Silverberg, Y. et al., "Passive-Mode Locking of a Semiconductor Diode-Laser", *Optics Letters*, vol. 9, pp. 507-509, Nov. 1984.
Smith, L. Montgomery et al., "Absolute Displacement Measurements Using Modulation of the Spectrum of White-Light in a Michelson Interferometer", *Applied Optics*, vol. 28, pp. 3339-3342, Aug. 1989.
Sonnenschein, C. M. et al. , "Signal-To-Noise Relationships for Coaxial Systems that Heterodyne Backscatter from Atmosphere", *Applied Optics*, vol. 10, pp. 1600-1604, Jul. 1971.
Sorin, W. V. et al., "Measurement of Rayleigh Backscattering at 1.55 mu m with 32 mu m Spatial Resolution", *IEEE Photonics Technology Letters*, vol. 4, pp. 374-376, Apr. 1992.
Sorin, W. V. et al., "A Simple Intensity Noise-Reduction Technique for Optical Low-Coherence Reflectometry", *IEEE Photonics Technology Letters*, vol. 4, pp. 1404-1406, Dec. 1992.
Swanson, E. A. et al., "High-Speed Optical Coherence Domair Reflectometry", *Optics Letters*, vol. 17, pp. 151-153, Jan. 1992.
Takada, K. et al., "High-Resolution OFDR with Incorporated Fiberoptic Frequency Encoder", *IEEE Photonics Technology Letters*, vol. 4, pp. 1069-1072, Sep. 1992.
Takada, Kazumasa et al., "Narrow-Band light Source with Acoustic Tunable Filter for Optical Low-Coherence Reflectometry", *IEEE Photonics Technology Letters*, vol. 8, pp. 658-660, May 1996.
Takada, Kazumasa et al., "New Measurement System for Fault Location in Optical Wave-Guide Devices Based on an Interometric-Technique", *Applied Optics*, vol. 26, pp. 1603-1606, May 1987.
Tateda, Mitsuhiro et al., "Interferometric Method for Chromatic Dispersion Measurement in a Single-Mode Optical Fiber", *IEEE Journal of Quantum Electronics*, vol. 17, pp. 404-407, Mar. 1981.
Toide, M. et al., "Two-Dimensional Coherent Detection Imaging in Multiple Scattering Media Based the Directional Resolution Capability of the Optical Heterodyne Method", *Applied Physics B (Photophysics and laser Chemistry)*, vol. B52, pp. 391-394, 1991.
Trutna, W. R. et al., "Continuously Tuned External-Cavity Semiconductor-Laser", *Journal of Lightwave Technology*, vol. 11, pp. 1279-1286, Aug. 1993.
Uttam, Deepak et al., "Precision Time Domain Reflectometry in Optical Fiber Systems Using a Frequency Modulated Continuous Wave Ranging Technique", Journal of *Lightwave Technology*, vol. 3, pp. 971-977, Oct. 1985.
Von Der Weid, J. P. et al., "On the Characterization of Optical Fiber Network Components with Optical Frequency Domain Reflectometry", Journal of *Lightwave Technology*, vol. 15, pp. 1131-1141, Jul. 1997.
Wysocki, P.F. et al., "Broad-Spectrum, Wavelength-Swept, Erbium-Doped Fiber Laser at 1.55-Mu-M", *Optics Letters*, vol. 15, pp. 879-881, Aug. 1990.
Youngquist, Robert C. et al., "Optical Coherence-Domain Reflectometry—A New Optical Evaluation Technique", *Optics Letters*, vol. 12, pp. 158-160, Mar. 1987.
Yun, S. H. et al., "Wavelength-Swept Fiber Laser with Frequency Shifted Feedback and Resonantly Swept Intra-Cavity Acoustioopic Tunable Filter", *IEEE Journal of Selected Topics in Quantium Electronics*, vol. 3, pp. 1087-1096, Aug. 1997.
Yun, S. H. et al., "Interrogation of Fiber Grating Sensor Arrays with a Wavelength-Swept Fiber Laser", *Optics Letters,* vol. 23, pp. 843-845, Jun. 1998.
Yung, K. M., "Phase-Domain Processing of Optical Coherence Tomography Images", *Journal of Biomedical Optics*, vol. 4, pp. 125-136, Jan. 1999.
Zhou, Xiao-Qun et al., "Extended-Range FMCW Reflectometry Using an optical Loop with a Frequency Shifter", *IEEE Photonics Technology Letters*, vol. 8, pp. 248-250, Feb. 1996.
Zorabedian, Paul et al., "Tuning Fidelity of Acoustooptically Controlled External Cavity Semiconductor-Lasers", *Journal of Lightwave Technology*, vol. 13, pp. 62-66, Jan. 1995.
Victor S. Y. Lin. et al., "A Porous Silicon-Based Optical Interferometric Biosensor", *Science Magazine*, vol. 278, pp. 840-843, Oct. 31, 1997.
De Boer, Johannes F. et al., "Review of Polarization Sensitive Optical Coherence Tomography and Stokes Vector Determination," *Journal of Biomedical Optics*, vol. 7, No. 3, Jul. 2002, pp. 359-371.
Jiao, Shuliang et al., "Depth-Resolved Two-Dimensional Stokes Vectors of Backscattered Light and Mueller Matrices of Biological Tissue Measured with Optical Coherence Tomography," *Applied Optics*, vol. 39, No. 34, Dec. 1, 2000, pp. 6318-6324.
Park, B. Hyde et al., "In Vivo Burn Depth Determination by High-Speed Fiber-Based Polarization Sensitive Optical Coherence Tomography," *Journal of Biomedical Optics*, vol. 6 No. 4, Oct. 2001, pp. 474-479.
Roth, Jonathan E. et al., "Simplified Methods for Polarization-Sensitive Optical Coherence Tomography," *Optics Letters*, vol. 26, No. 14, Jul. 25, 2001, pp. 1069-1071.
Hitzenberger, Christopher K. et al., "Measurement and Imaging of Birefringence and Optic Axis Orientation by Phase Resolved Polarization Sensitive Optical Coherence Tomography," *Optics Express*, vol. 9, No. 13, Dec. 17, 2001, pp. 780-790.
Wong, Brian J.F. et al., "Optical Coherence Tomography of the Rat Cochlea," Journal of *Biomedical Optics*, vol. 5, No. 4, Oct. 2000, pp. 367-370.
Yao, Gang et al., "Propagation of Polarized Light in Turbid Media: Simulated Animation Sequences," *Optics Express*, vol. 7, No. 5, Aug. 28, 2000, pp. 198-203.
Wang, Xiao-Jun et al., "Characterization of Dentin and Enamel by Use of Optical Coherence Tomography," *Applied Optics*, vol. 38, No. 10, Apr. 1, 1999, pp. 2092-2096.
De Boer, Johannes F. et al., "Determination of the Depth-Resolved Stokes Parameterss of Light Backscattered from Turbid Media by use of Polarization-Sensitive Optical Coherence Tomography," *Optics Letters*, vol. 24, No. 5, Mar. 1, 1999, pp. 300-302.
Ducros, Mathieu G. et al., "Polarization Sensitive Optical Coherence Tomography of the Rabbit Eye," *Journal of Selected Topics in Quantum Electronics*, vol. 5, No. 4, Jul./Aug. 1999, pp. 1159-1167.
Groner, Warren et al., "Orthogonal Polarization Spectral Imaging: A New Method of Study of the Microcirculation," *Nature Medicine Inc.*, vol. 5, No. 10, Oct. 1999, pp. 1209-1213.
De Boer, Johannes F. et al., "Polarization Effects in Optical Coherence Tomography of Various Biological Tissues," *IEEE Journal of Selected Topics in Quantum Electronics*, vol. 5, No. 4, Jul./Aug. 1999, pp. 1200-1204.
Yao, Gang et al., "Two-Dimensional Depth-Resolved Mueller Matrix Characterization of Biological Tissue by Optical Coherence Tomography," *Optics Letter*, Apr. 15, 1999, vol. 24, No. 8, pp. 537-539.
Lu, Shih-Yau et al., "Homogeneous and Inhomogeneous Jones Matrices," *J. Opt. Soc. Am. A.,* vol. 11, No. 2, Feb. 1994, pp. 766-773.
Brickel, S. William et al., "Stokes Vectors, Mueller Matrices, and Polarized Scattered Light," *Am. J. Phys.,* vol. 53, No. 5, May 1985 pp. 468-478.
Bréhonnet, F. Le Roy et al., "Optical Media and Target Characterization by Mueller Matrix Decomposition," *J. Phys. D: Appl. Phys.* 29, 1996, pp. 34-38.
Cameron, Brent D. et al., "Measurement and Calculation of the Two-Dimensional Backscattering Mueller Matrix of a Turbid Medium," *Optics Letters*, vol. 23, No. 7, Apr. 1, 1998, pp. 485-487.
De Boer, Johannes F. et al., "Two-Dimensional Birefringence Imaging in Biological Tissue by Polarization-Sensitive Optical Coherence Tomography," *Optics Letters*, vol. 22, No. 12, Jun. 15, 1997, pp. 934-936.

De Boer, Johannes F. et al., "Imaging Thermally Damage Tissue by Polarization Sensitive Optical Coherence Tomography," *Optics Express*, vol. 3, No. 6, Sep. 14, 1998, pp. 212-218.
Everett, M.J. et al., "Birefringence Characterization of Biological Tissue by Use of Optical Coherence Tomography," *Optics Letters*, vol. 23, No. 3, Feb. 1, 1998, pp. 228-230.
Hee, Michael R. et al., "Polarization-Sensitive Low-Coherence Reflectometer for Birefringence Characterization and Ranging," *J. Opt. Soc. Am. B.,* vol. 4, No. 6, Jun. 1992, pp. 903-908.
Barakat, Richard, "Statistics of the Stokes Parameters," *J. Opt. Soc. Am. B.,* vol. 4, No. 7, Jul. 1987, pp. 1256-1263.
Schmitt, J. M. et al., "Cross-Polarization Backscatter in Optical Coherence Tomography of Biological Tissue," *Optics Letters*, vol. 23, No. 13, Jul. 1, 1998, pp. 1060-1062.
Schoenberger, Klaus et al., "Mapping of Birefringence and Thermal Damage in Tissue by use of Polarization-Sensitive Optical Coherence Tomography," *Applied Optics*, vol. 37, No. 25, Sep. 1, 1998, pp. 6026-6036.
Piecer, Mark C., et al., "Simultaneous Intensity, Birefringence, and Flow Measurements with High-Speed Fiber-Based Optical Coherence Tomography," *Optics Letters*, vol. 27, No. 17, Sep. 1, 2002, pp. 1534-1536.
De Boer, Johannes F. et al., "Review of Polarization Sensitive Optical Coherence Tomography and Stokes Vector Determination," *Journal of Biomedical Optics*, Jul. 2002, vol. 7, No. 3, pp. 359-371.
Fried, Daniel et al., "Imaging Caries Lesions and Lesion Progression with Polarization Sensitive Optical Coherence Tomography," *Journal of Biomedical Optics*, vol. 7, No. 4, Oct. 2002, pp. 618-627.
Jiao, Shuliang et al., "Two-Dimensional Depth-Resolved Mueller Matrix of Biological Tissue Measured with Double-Beam Polarization-Sensitive Optical Coherence Tomography," *Optics Letters*, vol. 27, No. 2, Jan. 15, 2002, pp. 101-103.
Jiao, Shuliang et al., "Jones-Matrix Imaging of Biological Tissues with Quadruple-Channel Optical Coherence Tomography," *Journal of Biomedical Optics*, vol. 7, No. 3, Jul. 2002, pp. 350-358.
Kuranov, R.V. et al., "Complementary Use of Cross Polarization and Standard OCT for Differential Diagnosis of Pathological Tissues," *Optics Express*, vol. 10, No. 15, Jul. 29, 2002, pp. 707-713.
Cense, Barry et al., "In Vivo Depth-Resolved Birefringence Measurements of the Human Retinal Nerve Fiber Layer by Polarization-Sensitive Optical Coherence Tomography," *Optics Letters*, vol. 27, No. 18, Sep. 15, 2002, pp. 1610-1612.
Ren, Hongwu et al., "Phase-Resolved Functional Optical Coherence Tomography: Simultaneous Imaging of In Situ Tissue Structure, Blood Flow Velocity, Standard Deviation, Birefringence, and Stokes Vectors in Human Skin," *Optics Letters*, vol. 27, No. 19, Oct. 1, 2002, pp. 1702-1704.
Tripathi, Renu et al., "Spectral Shaping for Non-Gaussian Source Spectra in Optical Coherence Tomography," *Optics Letters*, vol. 27, No. 6, Mar. 15, 2002, pp. 406-408.
Yasuno, Y. et al., "Birefringence Imaging of Human Skin by Polarization-Sensitive Spectral Interferometric Optical Coherence Tomography," *Optics Letters*, vol. 27, No. 20, Oct. 15, 2002, pp. 1803-1805.
White, Brian R. et al., "In Vivo Dynamic Human Retinal Blood Flow Imaging Using Ultra-High-Speed Spectral Domain Optical Doppler Tomography," *Optics Express*, vol. 11, No. 25, Dec. 15, 2003, pp. 3490-3497.
De Boer, Johannes F. et al., "Improved Signal-to-Noise Ratio in Spectral-Domain Compared with Time-Domain Optical Coherence Tomography," *Optics Letters*, vol. 28, No. 21, Nov. 1, 2003, pp. 2067-2069.
Jiao, Shuling, et al., "Optical-Fiber-Based Mueller Optical Coherence Tomography," *Optics Letters*, vol. 28, No. 14, Jul. 15, 2003, pp. 1206-1208.
Jiao, Shuliang et al., "Contrast Mechanisms in Polarization-Sensitive Muller-Matrix Optical Coherence Tomography and Application in Burn Imaging," *Applied Optics*, vol. 42, No. 25, Sep. 1, 2003, pp. 5191-5197.
Moreau, Julien et al., "Fuel-Field Birefringence Imaging by Thermal-Light Polarization-Sensitive Optical Coherence Tomography. I. Theory," *Applied Optics*, vol. 42, No. 19, Jul. 1, 2003, pp. 3800-3810.
Moreau, Julien et al., "Fuel-Field Birefringence Imaging by Thermal-Light Polarization-Sensitive Optical Coherence Tomography. II. Instrument and Results," *Applied Optics*, vol. 42, No. 19, Jul. 1, 2003, pp. 3811-3818.
Morgan, Stephen P. et al., "Surface-Reflection Elimination in Polarization Imaging of Superficial Tissue," *Optics Letters*, vol. 28, No. 2, Jan. 15, 2003, pp. 114-116.
Oh, Jung-Taek et al., "Polarization-Sensitive Optical Coherence Tomography for Photoelasticity Testing of Glass/Epoxy Composites," *Optics Express*, vol. 11, No. 14, Jul. 14, 2003, pp. 1669-1676.
Park, B. Hyle et al., "Real-Time Multi-Functional Optical Coherence Tomography," *Optics Express*, vol. 11, No. 7, Apr. 7, 2003, pp. 782-793.
Shribak, Michael et al., "Techniques for Fast and Sensitive Measurements of Two-Dimensional Birefingence Distributions," *Applied Optics*, vol. 42, No. 16, Jun. 1, 2003, pp. 3009-3017.
Somervell, A.R.D. et al., "Direct Measurement of Fringe Amplitude and Phase Using a Heterodyne Interferometer Operating in Broadband Light," *Elsevier, Optics Communications*, Oct. 2003.
Stifter, D. et al., "Polarisation-Sensitive Optical Coherence Tomography for Medical Characterisation and Strain-Field Mapping," Applied Physics A 76, Materials Science & Processing, Jan. 2003, pp. 947-951.
Davé, Digant P. et al., "Polarization-Maintaining Fiber-Based Optical Low-Coherence Reflectometer for Characterization and Ranging of Birefingence," *Optics Letters*, vol. 28, No. 19, Oct. 1, 2003, pp. 1775-1777.
Yang, Ying et al., "Observations of Birefringence in Tissues from Optic-Fibre-Based Optical Coherence Tomography," *Measurement Science and Technology*, Nov. 2002, pp. 41-46.
Yun. S.H. et al., "High-Speed Optical Frequency-Domain Imaging," *Optics Express*, vol. 11, No. 22, Nov. 3, 2003, pp. 2953-5963.
Yun, S.H. et al., "High-Speed Spectral-Domain Optical Coherence Tomography at 1.3 μm Wavelength," *Optics Express*, vol. 11, No. 26, Dec. 29, 2003, pp. 3598-3604.
Zhang, Jun et al., "Determination of Birefringence and Absolute Optic Axis Orientation Using Polarization-Sensitive Optical Coherence Tomography with PM Fibers," *Optics Express*, vol. 11, No. 24, Dec. 1, 2003, pp. 3262-3270.
Pircher, Michael et al., "Three Dimensional Polarization Sensitive OCT of Human Skin In Vivo," 2004, *Optical Society of America*.
Götzinger, Erich et al., "Measurement and Imaging of Birefringencement Properties of the Human Cornea with Phase-Resolved, Polarization-Sensitive Optical Coherence Tomography," *Journal of Biomedical Optics*, vol. 9, No. 1, Jan./Feb. 2004, pp. 94-102.
Guo, Shuguang et al., "Depth-Resolved Birefringence and Differential Optical Axis Orientation Measurements with Fiber-based Polarization-Sensitive Optical Coherence Tomography," *Optics Letters*, vol. 29, No. 17, Sep. 1, 2004, pp. 2025-2027.
Huang, Xiang-Run et al., "Variation of Peripapillary Retinal Nerve Fiber Layer Birefringence in Normal Human Subjects," *Investigative Opthalmology & Visual Science*, vol. 45, No. 9, Sep. 2004, pp. 3073-3080.
Matcher, Stephen J. et al., "The Collagen Structure of Bovine Intervertebral Disc Studied Using Polarization-Sensitive Optical Coherence Tomography," *Physics in Medicine and Biology*, 2004, pp. 1295-1306.
Nassif, Nader et al., "In Vivo Human Retinal Imaging by Ultrahigh-Speed Spectral Domain Optical Coherence Tomography," *Optics Letters*, vol. 29, No. 5, Mar. 1, 2004, pp. 480-482.
Nassif, N.A. et al., "In Vivo High-Resolution Video-Rate Spectral-Domain Optical Coherence Tomography of the Human Retina and Optic Nerve," *Optics Express*, vol. 12, No. 3, Feb. 9, 2004, pp. 367-376.
Park, B. Hyle et al., Comment on "Optical Fiber-Based Mueller Optical Coherence Tomography," *Optics Letters*, vol. 29, No. 24, Dec. 15, 2004, pp. 2873-2874.
Park, B. Hyle et al., "Jone Matrix Analysis for a Polarization-Sensitive Optical Coherence Tomography System Using Fiber-Optic Components," *Optics Letters*, vol. 29, No. 21, Nov. 1, 2004, pp. 2512-2514.

Pierce, Mark C. et al., "Collagen Denaturation can be Quantified in Burned Human Skin Using Polarization-Sensitive Optical Coherence Tomography," *Elsevier, Burns*, 2004, pp. 511-517.
Pierce, Mark C. et al., "Advances in Optical Coherence Tomography Imaging for Dermatology," *The Society for Investigative Dermatology, Inc.* 2004, pp. 458-463.
Pierce, Mark C. et al., "Birefringence Measurements in Human Skin Using Polarization-Sensitive Optical Coherence Tomography," *Journal of Biomedical Optics*, vol. 9, No. 2, Mar./Apr. 2004, pp. 287-291.
Cense, Barry et al., "In Vivo Birefringence and Thickness Measurements of the Human Retinal Nerve Fiber Layer Using Polarization-Sensitive Optical Coherence Tomography," *Journal of Biomedical Optics*, vol. 9, No. 1, Jan./Feb. 2004, pp. 121-125.
Pircher, Michael et al., "Imaging Of Polarization Properties of Human Retina in Vivo with Phase Resolved Transversal PS-OCT," *Optics Express*, vol. 12, No. 24, Nov. 29, 2004 pp. 5940-5951.
Pitcher, Michael et al., "Transversal Phase Resolved Polarization Sensitive Optical Coherence Tomography," *Physics in Medicine & Biology*, 2004, pp. 1257-1263.
Srinivas, Shyam M. et al., "Determination of Burn Depth by Polarization-Sensitive Optical Coherence Tomography," *Journal of Biomedical Optics*, vol. 9, No. 1, Jan./Feb. 2004, pp. 207-212.
Strasswimmer, John et al., "Polarization-Sensitive Optical Coherence Tomography of Invasive Basal Cell Circonoma," *Journal of Biomedical Optics*, vol. 9, No. 2, Mar./Apr. 2004, pp. 292-298.
Todorovič, Miloš et al., "Determination of Local Polarization Properties of Biological Samples in the Presence of Diattenuation by use of Mueller Optical Coherence Tomography," *Optical Letters*, vol. 29, No. 20, Oct. 15, 2004, pp. 2402-2404.
Yasuno, Yoshiaki et al., "Polarization-Sensitive Complex Fourier Domain Optical Coherence Tomography for Jones Matrix Imaging of Biological Samples," Applied Physics Letters, vol. 85, No. 15, Oct. 11, 2004, pp. 3023-3025.
Acioli, L. H., M. Ulman, et al. (1991). "Femtosecond Temporal Encoding in Barium-Titante." *Optics Letters* 16(24): 1984-1986.
Aigouy, L., A. Lahrech, et al., (1999). "Polarization effects in apertectureless scanning near-filed optical microscopy: an experimental study." *Optics Letters* 24(4): 187-189.
Akiba, M., K. P. Chan, et al. (2003). "Full-filed optical coherence tomography by two-dimensional heterodyne detection with a pair of CCD cameras." *Optics Letters* 28(10): 816-818.
Akkin, T., D. P. Dave, et al., (2004). "Detection of neural activity using phase-sensitive optical low-coherence reflectometry." *Optics Express* 12(11): 2377-2386.
Akkin, T., D. P. Dave, et al. (2003). "Surface analysis using phase sensitive optical low coherence reflectometry." *Lasers in Surgery and Medicine*: 4-4.
Akkin, T., D. P. Dave, et al. (2003). "Imaging tissue response to electrical and photothermal stimulation with nanometer sensivity." *Lasers in Surgery and Medicine* 33(4): 219-225.
Akkin, T., T. E. Milner, et al. (2002). "Phase-sensitive measurement of birefringence change as an indication of neural functionality and diseases." *Lasers in Surgery and Medicine*: 6-6.
Andretzky, P., Lindner, M.W., Herrmann, J.M., Schultz, A., Konzog, M., Kiesewetter, F., Haeusler, G. (1999). "Optical coherence tomography by 'spectral radar': Dynamic range estimation and in vivo measurements of skin." *Proceedings of SPIE—The International Society for Optical Engineering* 3567: pp. 78-87.
Antcliff, R. J., T. J. ffytche, et al., (2000). "Optical coherence tomography of melanocytoma." *American Journal of Ophthalmology* 130(6): 845-7.
Antcliff, R. J., M. R. Standford, et al. (2000). "Comparison between optical coherence tomography and fundus fluorescein angiography for the detection of cystoid mascular edema in patients with uveitis." *Ophthalmology* 107(3): 593-9.
Anvari, B., T. E. Milner, et al. (1995). "Selective Cooling of Biological Tissues—Application for Thermally Mediated Therapeutic Procedures." *Physics in Medicine and Biology* 40(2): 241-252.
Anvari, B., B. S. Tanenbaum, et al. (1995). "A Theoretical-Study of the Thermal Response of Skin of Cryogen Spray Cooling and Pulsed-Laser Irradiation—Implications for Treatment of Port-Wine Stain Birthmarks." *Physics in Medicine and Biology* 40(9): 1451-1465.
Arend, O., M. Ruffer, et al. (2000). "Macular circulation in patients with diabetes mellitus with and without arterial hypertension." *British Journal of Ophthalmology* 84(12): 1392-1396.
Arimoto, H. and Y. Ohtsuka (1997). "Measurements of the complex degree of spectral coherence by use of a wave-front-folded interferometer." *Optics Letters* 22(13):958-960.
Azzolini, C., F. Patelli, et al. (2001). "Correlation between optical coherence tomography data and biomicroscopic interpretation of idiopathic macular hole." *American Journal of Ophthalmology* 132(3): 348-55.
Baba, T., K. Ohno-Matsui, et al. (2002). "Optical coherence tomography of choroidal neovascularization in high myopia." *Acta Ophthalmoloqica Scandinavica* 80(1):82-7.
Bail, M. A. H., Gerd; Herrmann, Jurgen M.; Lindner, Michael W.; Ringer, R. (1996). "Optical coherence tomography with the "spectral radar": fast optical analysis in volume scatters by short-coherence interferometry." *Proc. SPIE*, 2925: p. 298-303.
Baney, D. M. and W. V. Sorin (1993). "Extended-Range Optical Low-Coherence Reflectometry Using a Recirculating Delay Technique." *Ieee Photonics Technology Letters* 5(9): 1109-1112.
Baney, D. M., B. Szafraniec, et al. (2002). "Coherent optical spectrum analyzer." *Ieee Photonics Technology Letters* 14(3): 355-357.
Barakat, R. (1981). "Bilinear Constraints between Elements of the 4by4 Mueller-Jones Transfer-Matrix of Polarization Theory." *Optics Communications* 38(3): 159-161.
Barakat, R. (1993). "Analytic Proofs of the Arago-Fresnel Laws for the Interference of Polarized-Light." *Journal of the Optical Society of America a-Optics Image Science and Vision* 10(1): 180-185.
Barbastathis, G. and D. J. Brady (1999). "Multidimensional tomographic imaging using volume halography." *Proceedings of the Ieee* 87(12) 2098-2120.
Bardal, S., A. Kamal, et al. (1992). "Photoinduced Birefringence in Optical Fibers—a Comparative-Study of Low-Birefringence and High-Birefringence Fibers." *Optics Letters* 17(6): 411-413.
Barsky, S. H., S. Rosen, et al. (1980). "Nature and Evolution of Port Wine Stains—Computer-Assisted Study." *Journal of Investigative Dermatology* 74(3): 154-157.
Barton, J. K., J. A. Izatt, et al. (1999). "Three-dimensional reconstruction of blood vessels from in vivo color Doppler optical coherence tomography images." *Dermatology* 198(4): 355-361.
Barton, J. K., A. Rollins, et al. (2001). "Photothermal coagulation of blood vessels: a comparison of high-sped optical coherence tomography and numerical modelling." *Physics in Medicine and Biology* 46.
Barton, J. K., A. J. Welch, et al. (1988. "Investigating pulsed dye laser-blood vessel interaction with color Doppler optical coherence tomography," *Optics Express* 3.
Bashkansky, M., M. D. Duncan, et al. (1997). "Subsurface defect detection in ceramics by high-speed resolution optical coherent tomography." *Optics Letters* 22 (1): 61-63.
Bashkansky, M. and J. Reintjes (2000). "Statistics and reduction of speckle in optical coherence tomography." *Optics Letters* 25(8): 545-547.
Baumgartner, A., S. Dichtl, et al. (2000). "Polarization-sensitive optical coherence tomography of dental structures." *Caries Research* 34(1): 59-69.
Baumgartner, A., C. K. Hitzenberger, et al. (2000). "Resolution-improved dual-beam and standard optical coherence tomography: a comparison." *Graefes Archive for Clinical and Experimental Ophthalmology* 238(5): 385-392.
Baumgartner, A., C. K. Hitzenberger, et al. (1998). "Signal and resolution enhancements in dual beam optical coherence tomography of the human eye." *Journal of Biomedical Optics* 3(1): 45-54.
Beaurepaire, E., P. Gleyzes, et al. (1998) *Optical coherence microscopy for the in-depth study of biological structures: System based on a parallel detection scheme*, Proceedings os SPIE—The International Study for Optical Engineering.
Beaurepaire, E., L. Moreaux, et al. (1999). "Combined scanning optical coherence and two-photon-excited fluorescence microscopy." *Optical Letters* 24(14): 969-971.
Bechara, F. G., T. Gambichler, et al. (2004). "Histomorphologic correlation with routine histology and optical coherence tomography." *Skin Research and Technology* 10 (3): 169-173.

Bechmann, M., M. J. Thiel, et al. (2000). "Central corneal thickness determined with optical coherence tomography in various types of glaucoma. [see comments]." *British Journal of Ophthalmology* 84(11): 1233-7.
Bek, T. and M. Kandi (2000). "Quantitative anomaloscopy and optical coherence tomography scanning in central serous chorioretinopathy." *Acta Ophthalmologica Scandinavica* 78(6): 632-7.
Benoit, A. M., K. Naoun, et al. (2001)."Linear dichroism of the retinal nerve fiber layer expressed with Mueller matrices." *Applied Optics* 40(4): 565-569.
Bicout, D., C. Brosseau, et al. (1994). "Depolarization of Multiply Scattered Waves by Spherical Diffusers—Influence of the Size Parameter." *Physical Review* E 49(2): 1767-1770.
Blanchot, L., M. Lebec, et al. (1997). *Low-coherence in depth microscopy for biological tissues imaging. Design of a real time control system*. Proceedings of SPIE—The International Society for Optical Engineering.
Blumenthal, E. Z. and R. N. Weinreb (2001). "Assessment of the retinal nerve fiber layer in clinical trials of glaucoma neuroprotection. [Review] [36 refs]." *Survey of Ophthalmology* 45(Suppl 3): S305-12; discussion S332-4.
Blumenthal, E. Z., J. M. Williams, et al. (2000). "Reproducibility of nerve fiber layer thickness measurement by use of optical coherence tomography." *Ophthalmology* 107(120: 2278-82.
Boppart, S. A., B. E. Bauma, et al. (1996). "Imaging developing neural morphology using optical coherence tomography." *Journal of Neuroscience Methods* 70.
Boppart, S. A., B. E. Bauma, et al. (1997). "Forward-imaging instruments for optical coherence tomography." *Optics Letters* 22.
Boppart, S. A., B. E. Bauma, et al. (1998). "Intraoperative assessment of microsurgery with three-dimensional optical coherence tomography." *Radiology* 208: 81-86.
Boppart, S. A., J. Herrmann, et al. (1999). "High-resolution optical coherence tomography-guided laser ablation of surgical tissue." *Journal of Surgical Research* 82(2): 275-84.
Bouma, B. E. and J. G. Fujimoto (1996). "Compact Kerr-lens mode-locked resonators." *Optics Letters* 21.
Bouma, B. E., L. E. Nelson, et al. (1998). "Optical coherence tomographic imaging of human tissue at 1.55 mu m and 1.81 mu m using Er and Tm-doped fiber sources." *Journal of Biomedical Optics* 3.
Bouma, B. E., M. Ramaswamy-Paye, et al. (1997). "Compact resonator designs for mode-locked solid-state lasers." *Applied Physics B* (*Lasers and Optics*) B65.
Bouma, B. E. and G. J. Tearney (2002). "Clinical imaging with optical coherence tomography." *Academic Radiology* 9(8): 942-953.
Bouma, B. E., G. J. Tearney, et al. (1996). "Self-phase-modulated Kerr-lens mode-locked Cr:forsterite laser source for optical coherence tomography." *Optics Letters* 21(22): 1839.
Bouma, B. E. G. J. Tearney, et al. (2000). "High-Resolution imaging of the human esophagus and stomach in vivo using optical coherence tomography." *Gastrointestinal Endoscopy* 51(4): 467-474.
Bouma, B. E., G. J. Tearney, et al. (2003). "Evaluation of intracoronary stenting by intravascular optical coherence tomography." *Heart* 89(3): 317-320.
Bourquin, S., V. Monterosso, et al. (2000). "Video-rate optical low-coherence reflectometry based on a linear smart detector array." *Optics Letters* 25(2): 102-104.
Bourquin, S., P. Seitz, et al. (2001). "Optical coherence topography based on a two-dimensional smart detector array." *Optics Letters* 26(8): 512-514.
Bouzid, A., M. A. G. Abushagur, et al. (1995). "Fiber-optic four-detector polarimeter." *Optics Communications* 118(3-4): 329-334.
Bowd, C., R. N. Weinreb, et al. (2000). "The retinal nerve fiber layer thickness in ocular hypertensive, normal, and glaucomatous eyes with optical coherence tomography." *Archives of Ophthalmology* 118(1): 22-6.
Bowd, C., L. M. Zangwill, et al. (2001). "Detecting early glaucoma by assessment of retinal nerve fiber layer thickness and visual function." *Investigative ophthalmology & Visual Science*42(9): 1993-2003.
Bowd, C., L. M. Zangwill, et al. (2002). "Imaging of the optic disc and the retinal nerve fiber layer: the effects of age, optic disc area, refractive error, and gender." *Journal of the Optical Society of America, A, Optics, Image Science & Vision* 19(1): 197-207.
Brand, S., J. M. Poneros, et al. (2000). "Optical coherence tomography in the gastrointestinal tract." *Endoscopy* 32(10): 796-803.
Brezinski, M. E. and J. G. Fujimoto (1999). "Optical coherence tomography: high-resolution imaging in nontransparent tissue." *IEEE Journal of Selected Topics in Quantum Electronics* 5(4): 1185-1192.
Brezinski, M. E., G. J. Terney, et al. (1996). "Imaging of coronary artery microstructure (in vitro) with optical coherence tomography." *American Journal of Cardiology* 77(1): 92-93.
Brezinski, M. E., G. J. Tearney, et al. (1996). "Optical coherence tomography for optical biopsy—Properties and demonstration of vascular pathology." *Circulation* 96(6): 1206-1213.
Brezinski, M. E., G. J. Tearney, et al. (1997). "Assessing atherosclerotic plaque morphology: Comparison of optical coherence tomography and high frequency intravascular ultrasound." *Heart* 77(5): 397-403.
Brink, H. B. K. and G. J. Vanblokland (1988). "Birefringence of the Human Foveal Area Assessed Invivo with Mueller-Matrix Ellipsometry." *Journal of the Optical Society of America a-Optics Image Science and Vision* 5(1): 49-57.
Brosseau, C. and D. Biscout (1994). "Entropy Production in Multiple-Scattering of Light by a Spatially Random Medium." *Physical Review* E 50(6): 4997-5005.
Burgoyne, C. F., D. E. Mercante, et al. (2002). "Change detection in regional and volumetric disc parameters using longitudinal confocal scanning laser tomography." *Ophthalmology* 109(3): 455-66.
Candido, R. and T. J. Allen (2002). "Haemodynamics in microvascular complications in type 1 diabetes." *Diabetes-Metabolism Research and Reviews* 18(4): 286-304.
Cense, B., T. C. Chen, et al. (2004). "Thickness and birefringence of healthy retinal nerve fiber layer tissue measured with polarization-sensitive optical coherence tomography." *Investigative Ophthalmology & Visual Science* 45(8): 2606-2612.
Cense, B., N. Nassif, et al. (2004). "Ultrahigh-Resolution High-Speed retinal Imaging Using Spectral-Domain Optical Coherence Tomography." *Optics Express* 12(11): 2435-24473.
Chance, B., J. S. Leigh, et al. (1988). "Comparison of Time-Resolved and Time-Unresolved Measurements of Deoxyhemoglobin in Brain." *Proceedings of the National Academy of Sciences of the United States of America* 85(14): 4971-4975.
Chang, E. P., D. A. Keedy, et al. (1974). "Ultrastructures of Rabbit Corneal Stroma—Mapping of Optical and Morphological Anisotropies." *Biochemica Et Biophysica Acta* 343(3): 615-626.
Chartier, T., A. Hideur, et al. (2001). "Measurement of the elliptical birefringence of single-mode optical fibers." *Applied Optics* 40(30): 5343-5353.
Chauhan, B. C., J. w. Blanchard, et al. (2000). "Technique for Detecting Serial Topographic Changes in the Optic Disc and Peripapillary Retina Using Scanning Laser Tomograph." *Invest Ophthalmol Vis Sci* 41:775-782.
Chen, Z. P., T. E. Milner, et al. (1997). "Optical Doppler tomographic imaging of fluid flow velocity in highly scattering media." *Optics Letters* 22(1): 64-66.
Chen, Z. P., T. E. Milner, et al., (1997). "Noninvasive imaging of in vivo blood flow velocity using optical Doppler tomography." *Optics Letters* 22(14): 1119-1121.
Chen, Z. P., Y. H. Zhao, et al. (1999). "Optical Doppler tomography." *Ieee Journal of Selected Topics in Quantum Electronics* 5(4): 1134-1142.
Cheong, W. F., S. A. Prahl, et al. (1990). "A Review of the Optical-Properties of biological Tissues." *Ieee Journal of Quantum Electronics* 26(12): 2166-2185.
Chernikov, S. V., Y. Zhu, et al. (1997). "Supercontinuum self-Q-switched ytterbium fiber laser." *Optics Letters* 22(5): 298-300.
Cho. S. H., B. E. Bouma, et al. (1999). "Low-repetition-rate high-peak-power Kerr-lens mode-locked Ti:AI/sub 2/0/sub 3/ laser with a multiple-pass cavity." *Optics Letters* 24(6): 417-419.

Choma, M. A., M. V. Sarunic, et al. (2003). "Sensitivity advantage of swept source and Fourier domain optical coherence tomography ." *Optics Express* 11(18): 2183-2189.
Choma, M. A., C. H. Yang et al. (2003). "Instantaneous quadrature low-coherence interferometry with 3×3 fiber-optic couplers." *Optics Letters* 28(22): 2162-2164.
Choplin, N. T. and D. C. Lundy (2001). "The sensitivity and specificity of scanning laser polarimetry in the detection of glaucoma in a clinical setting." *Ophthalmology* 107 (5): 899-904.
Christens Barry, W. A., W. J. Green, et al. (1996). "Spatial mapping of polarized light transmission in the central rabbit cornea." *Experimental Eye Research* 62(6): 651-662.
Chvapil, M., D. P. Speer, et al. (1984). "Identification of the depth of burn injury by collagen stainability." *Plastic & Reconstructive Surgery* 73(3): 438-41.
Cioffi, G. A. (2001). "Three common assumptions about ocular blood flow and glaucoma." *Surgery of Ophthalmology* 45: S325-S331.
Coleman, A. L. (1999). "Glaucoma." *Lancet* 354(9192): 1803-10.
Collaborative Normal-Tension Glaucoma Study Group (1998). "Comparision of Glaucomatous Progression Between Untreated Patients With Normal Tension Glaucoma and Patients with Therapeutically Reduced Intraocular Pressures." *Am J Ophthalmol* 126: 487-97.
Collaborative Normal-Tension Glaucoma Study Group (1998). "The effectiveness of intraocular pressure reduction in the treatment of normal-tension glaucoma." *Am J Ophthalmol* 126: 498-505.
Collaborative Normal-Tension Glaucoma Study Group (2001). "Natural History of Normal-Tension Glaucoma." *Opthalmology* 108: 247-253.
Colston, B. W., M. J. Everett, et al. (1998). "Imaging of hard- and soft tissue structure in the oral cavity by optical coherence tomography." *Applied Optics* 37(16): 3582-3585.
Colston, B. W., U. S. Sathyam, et al. (1998). "Dental OCT." *Optics Express* 3(6): 230-238.
Congdon, N. G., D. S. Friedman, et al. (2003). "Important causes of visual impairment in the world today." *Jama—Journal of the American Medical Association* 290(15): 2057-2060.
Cregan, R. F., B. J. Mangan, et al. (1999). "Single-mode photonic band gap guidance of light in air." *Science* 285(5433): 1537-1539.
DalMolin, M., A. Galtrarossa, et al. (1997). "Experimental investigation of linear polarization in high-birefringence single-mode fibers." *Applied Optics* 36(12); 2526-2528.
Danielson, B. L. and C. D. Whittenbrg (1987). "Guided-Wave Reflectometry with Micrometer Resolution." *Applied Optics* 26(14): 2836-2842.
Dave, D. P. and T. E. Milner (2000). "Doppler-angle measurement in highly scattering media." *Optics Letters* 25(20): 1523-1525.
de Boer, J. F., T. E. Milner, et al. (1998). *Two dimensional birefringence imaging in biological tissue using phase and polarization sensitive optical coherence tomography.* Trends in Optics and Photonics (TOPS): Advances in Optical Imaging and Photon Migration, Orlando, USA, Optical Society of America, Washington, DC 1998.
de Boer, J. F., C. E. Saxer, et al. (2001). "Stable carrier generation and phase-resolved digital data processing in optical coherence tomography." *Applied Optics* 40(31): 5787-5790.
Degroot, P. and L. Deck (1993). "3-Dimensional Imaging by Sub-Nyquist Sampling of White-Light Interferograms." *Optics Letters* 18(17): 1462-1464.
Denk, W., J. H. Strickler, et al. (1990). "2-Photon Laser Scanning Fluorescence Microscopy." *Science* 248(4951): 73-76.
Descour, M. R., A. G. H. O. Karkkainen, et al. (2002). "Toward the development of miniaturized Imaging systems for detection of pre-cancer." *Ieee Journal of Quantum Electronics* 38(2): 122-130.
Dettwiller, L. (1997). "Polarization state interference: A general investigation." *Pure and Applied Optics* 6(1): 41-53.
DiCarlo, C. D., W. P. Roach, et al. (1999). "Comparison of optical coherence tomography imaging of cataracts with histopathology." *Journal of Biomedical Optics* 4.
Ding, Z., Y. Zhao, et al. (2002). "Real-time phase-resolved optical coherence tomography and optical Doppler tomography." *Optics Express* 10(5): 236-245.
Dobrin, P. B. (1996). "Effect of histologic preparation of the cross-sectional area of arterial rings." *Journal of Surgical Research* 61(2): 413-5.
Donohue, D. J., B. J. Stoyanov, et al. (1995). "Numerical Modeling of the Corneas Lamellar Structure and Birefringence Properties." *Journal of the Optical Society of America a-Optics Image Science and Vision* 12(7): 1425-1438.
Doornbos, R. M. P., R. Lang, et al. (1999). "The determination of in vivo human tissue optical properties and absolute chromophore concentrations using spatially resolved steady-state diffuse reflectance spectroscopy." *Physics in Medicine and Biology* 44(4): 967-981.
Drexler, W., A. Baumgartner, et al. (1997). "Biometric investigation of changes in the anterior eye segment during accomodation." *Vision Research* 37(19): 2789-2800.
Drexler, W., A. Baumgartner, et al. (1997). "Submicrometer precision biometry of the anterior segment of the human eye." *Investigative Ophthalmology & Visual Science* 38(7): 1304-1313.
Drexler, W., A. Baumgartner, et al. (1998). "Dual beam optical coherence tomography: signal identification for ophthalmologic diagnosis." *Journal of Biomedical Optics* 3 (1): 55-65.
Drexler, W., O. Findl, et al. (1998). "Partial coherence interferometry: A novel approach to biometry in cataract surgery." *American Journal of Ophthalmology* 126(4): 524-534.
Drexler, W., O. Findl, et al. (1997). "Clinical feasibility of dual beam optical coherence topography and tomography for ophthalmologic diagnosis." *Investigative Ophthalmology & Visual Science* 38(4): 1038-1038.
Drexler, W., C. K. Hitzenberger, et al. (1998). "Investigation of dispersion effects in ocular media by multiple wavelength partial coherence interferometry." *Experimental Eye Research* 66(1): 25-33.
Drexler, W., C. K. Hitzenberger, et al. (1996). "(Sub)micrometer precision biometry of the human eye by optical coherence tomography and topography." *Investigative Ophthalmology & Visual Science* 37(3): 4374-4374.
Drexler, W., C. K. Hitzenberger, et al. (1995). "Measurement of the Thickness of Fundus Layers by Partial Coherence Tomography." *Optical Engineering* 34(3): 701-710.
Drexler, W., U. Morgner, et al. (2001). "Ultrahigh-resolution ophthalmic optical coherence tomography." *Nature Medicine* 7 (4): 502-507.
Drexler, W., U. Morgner, et al. (2001). "Ultra-high resolution ophthalmic optical coherence tomography. [erratum appears in Nat Med 2001 May;7(5):636.]." *Nature Medicine* 7 (4): 502-7.
Drexler, W., H. Sattmann, et al. (2003). "Enhanced visualization of macular pathology with the use of ultrahigh-resolution optical coherence tomography." *Archives of Ophthalmology* 121(5): 695-706.
Drexler, W., D. Stamper, et al. (2001). "Correlation of collagen organization with polarization sensitive imaging of in vitro cartilage: implications for osteoarthritis." *Journal of Rheumatology* 28(6): 1311-8.
Droog, E. J., W. Steenbergen, et al. (2001). "Measurement of depth of burns by laser Doppler perfusion imaging." *Burns* 27(6): 561-8.
Dubois, A., K. Grieve, et al. (2004). "Ultrahigh-resolution full-field optical coherence tomography." *Applied Optics* 43(14): 2874-2883.
Dubois, A., L. Vabre, et al. (2002). "High-resolution full-field optical coherence tomography with a Linnik microscope." *Applied Optics* 41(4): 805-812.
Ducros, M., M. Laubscher, et al. (2002). "Parallel optical coherence tomography in scattering samples using a two-dimensional smart-pixel detector array." *Optics Communications* 202(1-3): 29-35.
Ducros, M. G., J. D. Marsack, et al. (2001). "Primate retina imaging with polarization-sensitive optical coherence tomography." *Journal of the Optical Society of America a-Optics Image Science and Vision* 18(12): 2945-2956.
Duncan, A., J. H. Meek, et al. (1995). "Optical Pathlength Measurements on Adult Head, Calf and Forearm and the Head of the Newborn-Infant Using Phase-Resolved Optical Spectroscopy." *Physics in Medicine and Biology* 40(2): 295-304.
Eigensee, A., G. Haeusler, et al. (1996). "New method of short-coherence interferometry in human skin (in vivo) and in solid volume scaterers." *Proceedings of the SPIE—The International Society for Optical Engineering* 2925: 169-178.

Eisnebeiss, W., J. Marotz, et al. (1999). "Reflection-optical multispectral imaging method for objective determination of burn depth." *Burns* 25(8): 697-704.
Elbaum, M., M. King, et al. (1972). "Wavelength-Diversity Technique for Reduction of Speckle Size." *Journal of the Optical Society of America* 62(5): 732-&.
Ervin, J. C., H. G. Lemij, et al. (2002). "Clinician change detection viewing longitudinal stereophotographs compared to confocal scanning laser tomography in the LSU Experimental Glaucoma (LEG) Study." *Ophthalmology* 109(3): 467-81.
Essenprises, M., C. E. Elwell, et al. (1993). "Special Dependence of Temporal Point Spread Functions in Human Tissues." *Applied Optics* 32(4): 418-425.
Eun, H. C. (1995). "Evaluation of skin blood flow by laser Doppler flowmetry. [Review] [151 refs]." *Clinics in Dermatology* 13(4): 337-47.
Evans, J. A., J. M. Poneros, et al. (2004). "Application of a histopathologic scoring system to optical coherence tomography (OCT) images to identify high-grade dysplasia in Barrett's esophagus." *Gastroenterology* 126(4): A51-A51.
Feldchtein, F. I., G. V. Gelikonov, et al. (1998). "In vivo OCT imaging of hard and soft tissue of the oral cavity." *Optics Express* 3(6): 239-250.
Feldchtein, F. I., G. V. Gelikonov, et al. (1998). "Endoscopic applications of optical coherence tomography." *Optics Express* 3(6): 257-270.
Fercher, A. F., W. Drexler, et al. (1997). "Optical ocular tomography." *Neuro- Ophthalmology* 18(2): 39-49.
Fercher, A. F., W. Drexler, et al. (1994). *Measurement of optical distances by optical spectrum modulation*. Proceedings of the SPIE—The International Society for Optical Engineering.
Fercher, A. F., W. Drexler, et al. (2003). "Optical coherence tomography—principles and applications." *Reports on Progress in Physics* 66(2): 239-303.
Fercher, A. F., C. Hitzenberger, et al. (1991). "Measurement of Intraocular Optical Distances Using Partially Coherent Laser-Light." *Journal of Modern Optics* 38(7): 1327-1333.
Fercher, A. F., K. Hitzenberger, et al. (1996). *Ocular partial coherence interferometry*. Proceedings of the SPIE—The International Society for Optical Engineering.
Fercher, A. F., C. K. Hitzenberger, et al. (1993). "In-Vivo Optical Coherence Tomography." *American Journal of Ophthalmology* 116(1): 113-115.
Fercher, A. F., C. K. Hitzenberger, et al. (1994). *In-vivo dual-beam optical coherence tomography*. Proceedings of SPIE—The International Society for Optical Engineering.
Fercher, A. F., C. K. Hitzenberger, et al. (1995). "Measurement of Intraocular Distances by Backscattering Spectral Interferometry." *Optics Communications* 117(1-2): 43-48.
Fercher, A. F., C. K. Hitzenberger, et al. (2000). "A thermal light source technique for optical coherence tomography." *Optics Communications* 185(1-3): 57-64.
Fercher, A. F., C. K. Hitzenberger, et al. (2001). "Numerical dispersion compensation for Partial Coherence Interferometry and Optical Coherence Tomography." *Optics Express* 9(12): 610-615.
Fercher, A. F., C. K. Hitzenberger, et al. (2002). "Dispersion compensation for optical coherence tomography depth- scan signals by a numerical technique." *Optics Communications* 204(1-6): 67-67.
Fercher, A. F., H. C. Li, et al. (1993). "Slit Lamp Laser-Doppler Interferometer." *Lasers in Surgery and Medicine* 13(4): 447-452.
Fercher, A. F., K. Mengedoht, et al. (1988). "Eye-Length Measurement by Interferometry with Partially Coherent-Light." *Optics Letters* 13(3): 186-188.
Ferro, P., M. Haelterman, et al. (1991). "All-Optical Polarization Switch with Long Low-Birefringence Fiber." *Electronics Letters* 27(16): 1407-1408.
Fetterman, M. R., D. Goswami, et al. (1998). "Ultrafast pulse shaping: amplification and characterization." *Optics Express* 3(10): 366-375.
Findl, O., W. Drexler, et al. (2001). "Improved prediction of intraocular lens power using partial coherence interferometry." *Journal of Cataract and Refractive Surgery* 27 (6): 861-867.
Fork, R. L., C. H. B. Cruz, et al. (1987). "Compression of Optical Pulse to 6 Femtoseconds by Using Cubic Phase Compensation." *Optics Letters* 12(7): 483-485.
Foshini, G. J. and C. D. Poole (1991). "Statistical-Theory of Polarization Dispersion in Single Mode Fibers." *Journal of Lightwave Technology* 9(11): 1439-1456.
Francia, C., F. Bruyere, et al. (1998). "PMP second-order effects on pulse propagation in single-mode optical fibers." *Ieee Photonics Technology Letters* 10(12): 1739-1741.
Fried, D., R. E. Glena, et al. (1995). "Nature of Light-Scattering in Dental Enamel and Dentin at Visible and near-Infrared Wavelengths." *Applied Optics* 34(7): 1278-1285.
Fujimoto. J. G., M. E. Brezinski, et al. et al. (1995). "Optical Biopsy and Imaging Using Optical Coherence Tomography." *Nature Medicine* 1(9): 970-972.
Fukasawa, A. and H. Iijima (2002). "Optical coherence tomography of choroidal osteoma." *American Journal of Ophthalmology* 133(3): 419-21.
Fymat, A. L. (1981). "High-Resolution Interferometric Spectrophotopolarimetry." *Optical Engineering* 20(1): 25-30.
Galtarossa, A., L. Palmieri, et al. (2000). "Statistical characterization of fiber random birefringence." *Optics Letters* 25(18): 1322-1324.
Galtarossa, A., L. Palmieri, et al. (2000). "Measurements of beat length and perturbation length in long single-mode fibers." *Optics Letters* 25(6): 384-386.
Gandjbakhche, A. H., P. Mills, et al. (1994). "Light-Scattering Technique for the Study of Orientation and Deformation of Red-Blood-Cells in a Concentrated Suspension." *Applied Optics* 33(6): 1070-1078.
Garcia, N. and M. Nieto-Vesperinas (2002). "Left-handed materials do not make a perfect lens." *Physical Review Letters* 88(20).
Gelikpnov, V. M., G. V. Gelikonov, et al. (1995). "Coherent Optical Tomography of Microscopic Inhomogheneities in Biological Tissue." *Jept Letters* 61(2): 158-162.
George, N. and A. Jain (1973). "Speckle Reduction Using Multiple Tones of Illumination." *Applied Optics* 12(6): 1202-1212.
Gibson, G. N., R. Klank, et al. (1996). "Electro-optically cavity-dumped ultrashort-pulse Ti:sapphire oscillatro." *Optics Letters* 21(4): 1055.
Gil, J. J. (2000). "Characteristic properties of Mueller matrices." *Journal of the Optical Society of America a-Optics Image Science and Vision* 17(2): 328-334.
Gil, J. J. and E. Bernabeu (1987). "Obtainment of the Polarizing and Retardation Parameters of Nondepolarizing Optical-System from the Polar Decomposition of Its Mueller Matrix." *Optik* 76(2): 67-71.
Gladkova, N. D., G. A. Petrova, et al. (2000). "In vivo optical coherence tomography imaging of human skin: norm and pathology." *Skin Research and Technology* 6 (1): 6-16.
Glaessl, A., A. G. Schreyer, et al. (2001). "Laser surgical planning with magnetic resonance imaging-based 3-dimensional reconstructions for intralesional Nd: YAG laser therapy of a venous malformation of the neck." *Archives of Dermatology* 137(10): 1331-1335.
Gloesmann, M., B. Hermann, et al. (2003). "Histologic correlation of pig retina radial stratisification with ultrahigh-resolution optical coherence tomography." *Investigative Ophthalmology & Visual Science* 44(4): 1696-1703.
Goldberg, L. and D. Mehuys (1994). "High-Power Superluminenscent Diode Source." *Electronics Letter* 30(20): 1682-1684.
Goldsmith, J. A., Y. Li, et al. (2005). "Anterior chamber width measurement by high speed optical coherence tomography." *Ophthalmology* 112(2): 238-244.
Goldstein, L. E., J. A. Muffat, et al. (2003). "Cytosolic beta-amyloid deposition and supranuclear cataracts in lenses from people with Alzheimer's disease." *Lancet* 361(9365): 1258-1265.
Golubovic, B., B. E. Bouma, et al. (1996). "Thin crystal, room-temperature Cr/sup 4 +/:forstefite laser near-infrared pumping."0 *Optics Letters* 21(24): 1993-1995.
Gonzalez, S. and Z. Tannous (2002). "Real-time, in vivo confocal reflectance microscopy of basal cell carcinoma." *Journal of the American Academy of Dermatology* 47(6): 869-874.

Gordon, M. O. and M. A. Kass (1999). "The Ocular Hypertension Treatment Study: design and baseline description of the participants." *Archives of Ophthalmology* 117(5): 573-83.
Grayson, T. P., J. R. Torgerson, et al. (1994). "Observation of the Nonlocal Pancharatnam Phase-Shift in the Process of Induced Coherence without Induced Emission." *Physical Review* A 49(1): 626-628.
Greaney, M. J., D. C. Hoffman, et al. (2002). "Comparison of optic nerve imaging methods to distinguish normal eyes from those with glaucoma." *Investigative Ophthalmology & Visual Science* 43(1): 140-5.
Greenfield, D. S., H. Bagga, et al. (2002). "Macular thickness changes in glaucomatous optic neuropathy detected using optical coherence tomography." *Archives of Ophthalmology* 121(1): 41-46.
Greenfield, D. S., R. W. Knighton, et al. (2000). "Effect of corneal polarization axis on assessment of retinal nerve fiber layer thickness by scanning laser polarimetry." *America Journal of Ophthalmology* 129(6): 715-722.
Griffin, R. A., D. D. Sampson, et al. (1995). "Coherence Coding for Photonic Code-Division Multiple Networks." *Journal of Lightwave Technology* 13(9): 1826-1837.
Guedes, V., J. S. Schuman, et al. (2003). "Optical coherence tomography measurement of macular and nerve fiber layer thickness in normal and glaucomatous human eyes." *Ophthalmology* 110(1): 177-189.
Gueugniaud, P. Y., H. Carsin, et al. (2000). "Current advances in the initial management of major thermal burns. [Reviews] [76 refs]." *Intensive Care Medicine* 26(7): 848-56.
Guido, S. and R. T. Tranquillo (1993). "A Methology for the Systematic and Quantitiative Study of Cell Contact Guidance in Oriented Collagen Gels—Correlation of Fibroblast Orientation and Gel Birefringence." *Journal of Cell Science* 106: 317-331.
Gurses-Ozden, R., H. Ishikawa, et al. (1999). "Increasing sampling improves reprodicbility of optical coherence tomography measurements." *Journal of Glaucoma* 8(4): 238-41.
Guzzi, R. (1998). "Scattering Theory from Homogeneous and Coated Spheres." 1-11.
Haberland, U. B., Vladimir; Schmitt, Hans J. (1996). "Optical coherent tomography of scattering media using electrically tunable near-infrared semiconductor laser." *Applied Optics* Draft Copy.
Haberland, U. R., Walter; Blazek, Vladimir Schmitt, Hans J. (1995). "Investigation of highly scattering media using near-infrared continuous wave tunable semiconductor laser." *Proc. SPIE* , 2389: 503-512.
Hale, G. M. and M. R. Querry (1973). "Optical-Constants of Water in 200-Nm to 200-Mum Wavelength Region." *Applied Optics* 12(3): 555-563.
Hammer, D. X., R. D. Ferguson, et al. (2002). "Image stabilization for scanning laser ophthalmoscopy." *Optics Express* 10(26): 1542.
Hara, T., Y. Ooi, et al. (1989). "Transfer Characteristics of the Microchannel Spatial Light-Modulator." *Applied Optics* 28(22): 4781-4786.
Harland, C. C., S. G. Kale, et al. (2000). "Differentiation of common benign pigmented skin lesions from melanoma by high-resolution ultrasound." *British Journal of Dermatology* 143(2): 281-289.
Hartl, I. X. D. Li, et al. (2001). "Ultrahigh-resolution optical coherence tomography using continuum generation in air-silica microstructure optical fiber." *Optical Letters* 26(9): 608-610.
Hassenstein, A., A. A. Bialasiewicz, et al. (2000). "Optical coherence tomography in uveitis patients." *America Journal of Ophthalmology* 130(5): 669-70.
Hattenhauer, M. G., D. H. Johnson, et al. (1998). "The probability of blindness from open-angle glaucoma. [see comments]." *Ophthalmology* 105(1-1): 2099-104.
Hausler, G., J. M. Herrmann, et al. (1996). "Observation of light propagation in volume scatters with 10(11)-fold slow motion." *Optics Letters* 21(14): 1087-1089.
Hazebroek, H. F. and A. A. Holscher (1973). "Interferometric Ellipsometry." *Journal of Physics E-Scientific Instruments* 6(9): 822-826.
Hazebroek, H. F. and W. M. Visser (1983). "Automated Laser Interfeometric Ellipsometry and Precision Reflectometry." *Journal of Physics E-Scientific Instruments* 16(7): 654-661.
He, Z. Y., N. Mukohzaka, et al. (1997). "Selective image extraction by synthesis of the coherence function using two-dimensional optical lock-in amplifier with microchannel spatial light modulator." *Ieee Photonics Technology Letters* 9(4): 514-516.
Hee, M. R., J. A. Izatt, et al. (1993). "Femtosecond Transillumination Optical Coherence Tomography." *Optics Letters* 18(12): 950-952.
Hee, M. R., J. A. Izatt, et al. (1995). "Optical coherence tomography of the human retina." *Archives of Ophthalmology* 113(3): 325-32.
Hee, M. R., C. A. Puliafito, et al. (1998). "Tomography of diabetic macular edema with optical coherence tomogrpahy." *Ophthalmology* 105(2): 360-70.
Hee, M. R., C. A. Puliafito, et al. (1995). "Quantitative assessment of macular edema with optical coherence tomography." *Archives of Ophthalmology* 113(8): 1019-29.
Hellmuth, T. and M. Well (1998). "Simultaneous measurement of dispersion, spectrum, and distance with a fourier transform spectrometer." *Journal of Biomedical Optics* 3(1): 7-11.
Hemenger, R. P. (1989). "Birefringence of a medium of tenuous parallel cylinders." *Applied Optics* 28(18): 4030-4034.
Henry, M. (1981). "Fresnel-Arago Laws for Interference in Polarized-Light—Demonstration Experiment." *American Journal of Physics* 49(7): 690-691.
Herz, P. R., Y. Chen, et al. (2004). "Micromotor endoscope catheter for in vico, ultrahigh-resolution optical coherence tomography." *Optics Letters* 29(19): 2261-2263.
Hirakawa, H., H. Iijima, et al. (1999). "Optical coherence tomography of cystoid masular edema associated with retinitis pigmentosa." *American Journal of Ophthalmology* 128(2): 185-91.
Hitzenberger, C. K., A. Baumgartner, et al. (1994). "Interferometric Measurement of Corneal Thickness with Micrometer Precision." *American Journal of Ophthalmology* 118(4): 468-476.
Hitzenberger, C. K., A. Baumgartner, et al. (1990). "Dispersion effects in partial coherence inferometry: Implications for intraocular ranging." *Journal of Biomedical Optics* 4(1): 144-151.
Hitzenberger, C. K., A. Baumgartner, et al. (1998). "Dispersion induced multiple signal peak splitting in partial coherence interferometry." *Optics Communications* 154 (4): 179-185.
Hitzenberger, C. K., M. Danner, et al. (1999). "Measurement of the spatial coherence of superluminescent diodes." *Journal of Modern Optics* 46(12): 1763-1774.
Hitzenberger, C. K. and A. F. Fercher (1999). "Differential phase contrast in optical coherence tomography." *Optics Letters* 24(9): 622-624.
Hitzenberger, C. K., M. Sticker, et al. (2001). "Differential phase measurements in low-coherence interferometry without 2 pi ambiguity." *Optics Letters* 26(23): 1864-1866.
Hoeling, B. M., A. D. Fernandez, et al. (2000). "An optical coherence microscope for 3-dimensional imaging in developmental biology." *Optics Express* 6(7): 136-146.
Hoerauf, H., C. Scholz, et al. (2002). "Transscleral optical coherence tomography: a new imaging method for the anterior segment of the eye." *Archives of Ophthalmology* 120(6): 816-9.
Hoffmann, K., M. Happe, et al. (1998). "Optical coherence tomography (OCT) in dermatology." *Journal of Investigative Dermatology* 110(4): 583-583.
Hoh, S. T., D. S. Greenfield, et al. (2000). "Optical coherence tomography and scanning laser polarimetry in normal, ocular hypertensive, and glaucomatous eyes." *American Journal of Ophthalmology* 129(2): 129-35.
Hohenleutner, U., M. Hilbet, et al. (1995). "Epidermal Damage and Limited Coagulation Depth with the Flashlamp-Pumped Pulsed Dye-Laser—a Histochemical-Study." *Journal of Investigative Dermatology* 104(5): 798-802.
Holland, A. J. A., H. C. O. Martin, et al. (2002). "Laser Doppler imaging prediction of burn wound outcome in children." *Burns* 28(1): 11-17.
Hotake, K, and T. Okugawa (1994). "Optical Information-Processing by Synthesis of the Coherence Function." *Journal of Lightwave Technology* 12(7): 1247-1255.
Hourdakis, C. J. and A. Perris (1995). "Monte-Carlo Estimation of Tissue Optical-Properties for Use in Laser Dosimetry." *Physics in Medicine and Biology* 40(3): 351-364.

Hu, Z., F. Li, et al. (2000). "Wavelength-tunable narrow-linewidth semiconductor fiber-ring laser." *IEEE Photonics Technology Letters* 12(8): 977-979.
Huang, F., W. Yang, et al. (2001). "Quadrature spectral interferometric detection and pulse shaping." *Optics Letters* 26(6): 382-384.
Huang, X. R. and R. W. Knighton (2002). "Linear birefringence of the retinal fiber layer measured in vitro with a multispectral imaging micropolarimeter." *Journal of Biomedical Optics* 7(2): 199-204.
Huber, R., M. Wojtkowski, et al. (2005). "Amplified, frequency swept lasers for frequency domain reflectometry and OCT imaging: design and scaling principles." *Optics Express* 13(9): 3513-3528.
Hunter, D. G., J. C. Sandruck, et al. (1999). "Mathematical modeling of retinal birefringence scanning." *Journal of the Optical Society of America a-Optics Image Science and Vision* 16(9): 2103-2111.
Hurwitz, H. H. and R. C. Jones (1941). "A new calculus for the treatment of optical systems II. Proof of the general equivalence theorems." *Journal of the Optical Society of America* 31(7): 493-499.
Huttner, B., C. De Barros, et al. (1999). "Polarization-induced pulse spreading in birefringent optical fibers with zero differential group delay." *Optics Letters* 24(6): 370-372.
Huttner, B., B. Gisin, et al. (1999). "Distributed PMD measurement with a polarization-OTDR in optical fibers." *Journal of Lightwave Technology* 17(10): 1843-1848.
Huttner, B., J. Reecht, et al. (1998). "Local birefringence measurements in single-mode fibers with coherent optical frequency-domain reflectometry." *Ieee Photonics Technology Letters* 10(10): 1458-1460.
Hyde, S. C. W., N. P. Barry, et al. (1995). "Sub-100-Mu-M Depth-Resolved Holographic Imaging through Scattering Media in the near-Infrared." *Optics Letters* 20(22): 2330-2332.
Hyde, S. C. W., N. P. Barry, et al. (1995). "Depth-Resolved Holographic Imaging through Scattering Media by Photorefraction." *Optics Letters* 20(11): 1331-1333.
Iftimia, N. V., B. E. Bouma, et al. (2004). "Adaptive ranging for optical coherence tomography." *Optics Express* 12(17): 4025-4034.
Iida, T., N. Hagimura, et al. (2000). "Evaluation of central serous chorioretinopathy with optical coherence tomography." *American Journal of Ophthalmology* 129(1): 16-20.
Imai, M., H. Iijima, et al. (2001). "Optical coherence tomography of tractional macular elevations in eyes with proliferative diabetic retinopathy, [republished in Am J Opthalmol. Sep. 2001; 132(3):458-61 ; 11530091.]." *American Journal of Ophthalmology* 132(1): 81-4.
Indebetouw, G. and P. Klysubun (2000). "Imaging through scattering media with depth resolution by use of low-coherence gating in spatiotemporal digital halography." *Optics Letters* 25(4): 212-214.
Ip, M. S., B. J. Baker, et al. (2002). "Anatomical outcomes of surgery for idiopathic macular hole as determined by optical coherence tomography." *Archives of Ophthalmology* 120(1): 29-35.
Ismail, R., V. Tanner, et al. (2002). "Optical coherence tomography imaging of severe commotio retinae and associated macular hole." *British Journal of Ophthalmology* 86(4): 473-4.
Izatt, J. A., M. R. Hee, et al. (1994). "Optical Coherence Microscopy in Scattering Media." *Optics Letters* 19(8): 590-592.
Izatt, J. A., M. R. Hee, et al. (1994). "Micrometer-scale resolution imaging of the anterior eye in vivo with optical coherence tomography." *Archives of Ophthalmology* 112 (12): 1584-9.
Izatt, J. A., M. D. Kulkami, et al. (1997). "In vivo bidirectional color Doppler flow imaging of picoliter blood volumes using optical coherence tomography." *Optics Letters* 22(18): 1439-1441.
Izatt, J. A., M. D. Kulkarni, et al. (1996). "Optical coherence tomography and microscopy in gastrointestinal tissues." *IEEE Journal of Selected Topics in Quantum Electronics* 2(4): 1017.
Jacques, S. L., J. S. Nelson, et al. (1993). "Pulsed Photothermal Radiometry of Port-Wine-Stain Lesions." *Applied Optics* 32(13): 2439-2446.
Jacques, S. L., J. R. Roman, et al. (2000). "Imaging superficial tissues with polarizedlight." *Lasers in Surgery and Medicine* 26(2): 119-129.
Jang, I. K., B. E. Bouma, et al. (2002). "Visualization of coronary atherosclerotic plaques in patients using optical coherence tomography: Comparison with intravascular ultrasound." *Journal of the American College of Cardiology* 39(4): 604-609.
Jang, I. K., B. D. MacNeill, et al. (2002). "In-vivo characterization of coronary plaques in patients with ST elevation acute myocardial infarction using optical coherence tomography (OCT)." *Circulation* 106(19): 698-698 3440 Suppl. S,.
Jang, I. K., G. J. Tearney, et al. (2000). "Comparison of optical coherence tomography and intravascular ultrasound for detection of coronary plaques with large lipid-core in living patients." *Circulation* 102(18): 509-509.
Jeng, J. C., A. Bridgeman, et al. (2003). "Laser Doppler imaging determines need for excision and grafting in advance of clinical judgment: a prospective blinded trail." *Burns* 29(7): 665-670.
Jesser, C. A., S. A. Boppart, et al. (1999). "High resolution imaging of transitional cell carcinoma with optical coherence tomography: feasibility for the evaluation of bladder pathology." *British Journal of Radiology* 72: 1170-1176.
Johnson, C. A., J. L. Keltner, et al. (2002). "Baseline visual field characteristics in the ocular hypertension treatment study." *Ophthalmology* 109(3): 432-7.
Jones, R. C. (1941). "A new calculus for the treatment of the optical systems III. The Sohncke theory of optical activity." *Journal of the Optical Society of America* 31 (7): 500-503.
Jones, R. C. (1941). "A new calculus for the treatment of optical systems I. Description and discussion of the calculus." *Journal of the Optical Society of America* 31(7): 488-493.
Jones, R. C. (1942). "A new calculus for the treatment of optical systems. IV." *Journal of the Optical Society of America* 32(8): 486-493.
Jones, R. C. (1947). "A New Calculus for the Treatment of Optical Systems .6. Experimental Determination of the Matrix." *Journal of the Optical Society of America* 37(2): 110-112.
Jones, R. C. (1947). "A New Calculus for the Treatment of Optical Systems .5. A More General Formulation, and Description of Another Calculus." *Journal of the Optical Society of America* 37(2): 107-110.
Jones, R. C. (1948). "A New Calculus for the Treatment of Optical Systems .7. Properties of the N-Matrices." *Journal of the Optical Society of America* 38(8): 671-685.
Jones, R. C. (1956). "New Calculus for the Treatment of Optical Systems .8. Electromagnetic Theory." *Journal of the Optical Society of America* 46(2): 126-131.
Jopson, R. M., L. E. Nelson, et al. (1999). "Measurement of second-order polarization-mode dispersion vectors in optical fibers." *Ieee Photonics Technology Letters* 11 (9): 1153-1155.
Jost, B. M., A. V. Sergienko, et al. (1998). "Spatial correlations of spontaneous down-converted photon pairs detected with a single-photon-sensitive CCD camera." *Optics Express* 3(2): 81-88.
Kaplan, B., E. Compain, et al. (2000). "Phase-modulated Mueller ellipsometry characterization of scattering of latex sphere suspensions." *Applied Optics* 39 (4): 629-636.
Kass, M. A., D. K. Heuer, et al. (2002). "The Ocular Hypertension Treatment Study: a randomized trial determines that topical ocular hypotensive medication delays or prevents the onset of primary open-angle glaucoma." *Archives of Ophthalmology* 120(6): 701-13; discussion 829-30.
Kasuga, Y. Y. Arai, et al. (2000). "Optical coherence tomography to confirm early closure of macular holes." *American Journal of Ophthalmology* 130(5): 675-6.
Kaufman, T., S. N. Lusthaus, et al. (1990). "Deep Partial Skin Thickness Burns—a Reproducible Animal-Model to Study Burn Wound-Healing." *Burns* 16(1): 13-16.
Kemp, N. J., J. Park, et al. (2005). "High-sensitivity determination of birefringence in turbid media with enhanced polarization-sensitive optical coherence tomography." *Journal of the Optical Society of America a-Optics Image Science and Vision* 22(3): 552-560.
Kerrigan-Baumrind, L. A. H. A. Quigley, et al. (2000). "Number of ganglion cells in glaucoma eyes compared with threshold visual field tests in the same persons." *Investigative Ophthalmology & Visual Science* 41(3): 741-8.
Kesen, M. R., G. L. Spaeth, et al. (2002). "The Heidelberg Retina Tomograph vs clinical impression in the diagnosis of glaucoma." *American Journal of Ophthalmology* 133(5): 613-6.

Kienle, A., and R. Hibst (1995). "A New Optimal Wavelength for Treatment of Port-Wine Stains." *Physics in Medicine and Biology* 40(10): 1559-1576.
Kienle, A., L. Lilge, et al. (1996). "Spatially resolved absolute diffuse reflectance measurements for noninvasive determination of the optical scattering and absorption coefficients of biological tissue." *Applied Optics* 35(13): 2304-2314.
Kim, B. Y. and S. S. Choi (1981). "Analysis and Measurement of Birefringence in Single-Mode Fibers Using the Backscattering Method." *Optics Letters* 6(11): 578-580.
Kimel, S., L. O. Svaasand et al. (1994). "Differential Vascular-Response to Laser Photothermolysis." *Journal of Investigative Dermatology* 103(5): 693-700.
Kloppemberg, F. W. H., G. Beerthuizen, et al. (2001). "Perfusion of burn wounds assessed by Laser Doppler Imaging is related to burn depth an healing time." *Burns* 27(4): 359-363.
Knighton, R. W. and X. R. Huang (2002). "Analytical methods for scanning laser polarimetry." *Optics Express* 10(21): 1179-1189.
Knighton, R. W., X. R. Huang, et al. (2002). "Analytical mode of scanning laser polarimetry for retinal nerve fiber layer assessment." *Investigative Ophthalmology & Visual Science* 43(2): 383-392.
Knuettel, A. R. S., Joseph M.: Shay, M.; Knutson, Jay R. (1994). "Stationary low-coherence light imaging and spectroscopy using a CCD camera." *Proc. SPIE*, vol. 2135: p. 239-250.
Knuttel, A. and M. Boehlau-Godau (2000). "Spatially confined and temporally resolved refractive index and scattering evaluation in human skin performed with optical coherence tomography." *Journal of Biomedical Optics* 5(1): 83-92.
Knuttel, A. and J. M. Schmitt (1993). "Stationary Depth-Profiling Reflectometer Based on Low-Coherence Interferometry." *Optics Communications* 102(3-4): 193-198.
Knuttel, A., J. M. Schmitt, et al. (1994). "Low-Coherence Reflectometry for Stationary Lateral and Depth Profiling with Acoustoopic Deflectors and a Ccd Camera." *Optics Letters* 19(4): 302-304.
Kobayashi, M., H. Hanafusa, et al. (1991). "Polarization-Independent Interferometric Optical-Time-Domain Reflectometer." *Journal of Lightwave Technology* 9(5): 623-628.
Kolios, M. C., M. D. Sherar, et al. (1995). "Large Blood-Vessel Cooling in Heated Tissues—a Numerical Study." *Physics in Medicine and Biology* 40(4): 477-494.
Koozekanani, D., K. Boyer, et al. (2001). "Retinal thickness measurements from optical coherence tomography using a Markov boundary model." *Ieee Transactions on Medical Imaging* 20(9): 900-916.
Kop, R. H. J. and R. Sprik (1995). "Phase-sensitive Interferometry with ultrashort optical pulses." *Review of Scientific Instruments* 66(12): 5459-5463.
Kramer, R. Z., J. Bella, et al. (1999). "Sequence dependent conformational variations of collagen triple-helical structure." *Nature Structural Biology* 6(5): 454-7.
Kulkarni, M. D., T. G. van Leeuwen, et al. (1998). "Velocity-estimation accuracy and frame-rate limitations in color Doppler optical coherence tomography." *Optics Letters* 23(13): 1057-1059.
Kwon, Y. H., C. S. Kim, et al. (2001). "Rate of visual field loss and long-term visual outcome in primary open-angle glaucoma." *American Journal of Ophthalmology* 132(1): 47-56.
Kwong, K. F., D. Yankelevich, et al. (1993). "400-Hz Mechanical Scanning Optical Delay-Line." *Optics Letters* 18(7): 558-560.
Landers, J., I. Goldberg, et al. (2002). "Analysis of risk factors that may be associated with progression from ocular hypertension to primary open angle glaucoma." *Clin Experiment Ophthalmology* 30(4): 242-7.
Laszlo, A. and A. Venetianer (1998). Heat resistance in mammalian cells: Lessons and challenges. *Stress of Life*. 851: 169-178.
Laszlo, A. and Venetianer (1998). "Heat resistance in mammalian cells: lesson and challenges. [Review] [52 refs]." *Annals of the New York Academy of Sciences* 851: 169-78.
Laufer, J., R. Simpson, et al. (1998). "Effect of temperature on the optical properties of ex vivo human dermis and subdermis." *Physics in Medicine and Biology* 43(9): 2479-2489.
Lederer, D. E., J. S. Shuman, et al. (2003). "Analysis of macular volume in normal and glaucomatous eyes using optical coherence tomography." *American Journal of Ophthalmology* 135(6): 838-843.
Lee, P. P., Z. W. Feldman, et al. (2003). "Longitudinal prevalence of major eye diseases." *Archives of Ophthalmology* 121(9): 1303-1310.
Lehrer, M. S., T. T. Sun, et al. (1998)."Strategies of opithelial repair: modulation of stem cell and transit amplifying cell proliferation." *Journal of Cell Science* 111(Pt 19): 2867-75.
Leibowitz, H. M., D. E. Krueger, et al. (1980). "The Framingham Eye Study monograph: An ophthalmological and epidemiological study of cataract, glaucoma, diabetic retinopathy, macular degeneration, and visual acuity in a general population of 2631 adults, 1973-1975." *Survey of Ophthalmology* 24(Suppl): 335-610.
Leitgeb, R., C. K. Hitzenberger, et al. (2003). "Performance of fourier domain vs. time domain optical coherence tomography." *Optics Express* 11(8): 889-894.
Leitgeb, R., L. F. Schmetterer, et al. (2002). "Flow velocity measurements by frequency domain short coherence interferometry." *Proc. SPIE* 4619: 16-21.
Leitgeb, R. A., W. Drexler, et al. (2004). "Ultrahigh resolution Fourier domain optical coherence tomography." *Optics Express* 12(10): 2156-2165.
Leitgeb, R. A., C. K. Hitzenberger, et al. (2003). "Phase-shifting algorithm to achieve high-speed long-depth-range probing by frequency-domain optical coherence tomography." *Optics Letters* 28(22): 2201-2203.
Leitgeb, R. A., L. Schmetterer, et al. (2003). "Real-time assessment of retinal blood flow with ultrafast acquisition by color Doppler Fourier domain optical coherence tomography." *Optics Express* 11(23): 3116-3121.
Leitgeb, R. A., L. Schmetterer, et al. (2004). "Real-time measurement of in vitro flow by Fourier-domain color Doppler optical coherence tomography." *Optics Letters* 29 (2): 171-173.
LeRoyBrehonnet, F. and B. LeJeune (1997). "Utilization of Mueller matrix formalism to obtain optical targets depolarization and polarization properties." *Progress in Quantum Electronics* 21(2): 109-151.
Leske, M. C., A. M. Connell, et al. (1995). "Risk factors for open-angle glaucoma. The Barbados Eye Study. [see comments]." *Archives of Ophthalmology* 113(7): 918-24.
Leske, M. C., A. M. Connell, et al. (2001). "Incidence of open-angle glaucoma: the Barbados Eye Studies. The Barbados Eye Studies Group. [see comments]." *Archives Ophthalmology* 119(1): 89-95.
Leske, M. C., A. Heijl, et al. (1999). "Early Manifest Glaucoma Trial. Design and Baseline Data." *Ophthalmology* 106(11): 2144-2153.
Lewis, S. E., J. R. DeBoer, et al. (2005). "Sensitive, selective, and analytical improvements to a porous silicon gas sensor." *Sensors and Actuators B: Chemical* 110(1): 54-65.
Lexer, F., C. K. Hitzenberger, et al. (1999). "Dynamic coherent focus OCT with depth-independent transversal resolution." *Journal of Modern Optics* 46(3): 541-553.
Li, X., C. Chudoba, et al. (2000). "Imaging needle for optical coherence tomography." *Optics Letters* 25: 1520-1522.
Li, X., T. H. Ko, et al. (2001). "Intraluminal fiber-optic Doppler imaging catheter for structural and functional optical coherence tomography." *Optics Letters* 26: 1906-1908.
Liddington, M. I. and P. G. Shakespeare (1996). "Timing of the thermographic assessment of burns." *Burns* 22(1): 26-8.
Lindmo, T., D. J. Smithies, et al. (1998). "Accuracy and noise in optical Doppler tomography studied by Monte Carlo simulation." *Physics in Medicine and Biology* 43(10): 3045-3064.
Liu, J., X. Chen, et al. (1999). "New thermal wave aspects on burn evaluation of skin subjected to instantaneous heating." *IEEE Transactions on Biomedical Engineering* 46(4): 420-8.
Luke, D. G., R. McBride, et al. (1995). "Polarization mode dispersion minimization in fiber-wound piezoeletric cylinders." *Optics Letters* 20(24): 2550-2552.
MacNiell, B. D., I. K. Jang, et al. (2004). "Focal and multi-focal plaque distributions in patients with macrophage acute and stable presentations of coronary artery disease." *Journal of the American College of Cardiology* 44(5): 972-979.

Mahgerefteh, D. and C. R. Menyuk (1999). "Effect of first-order PMD compensation on the statistics of pulse broadening in a fiber with randomly varying birefringence." *Ieee Photonics Technology Letters* 11(3): 340-342.
Maitland, D. J. and J. T. Walsh, Jr. (1997). "Quantitative measurements of linear birefringence during heating of native collagen." *Lasers in Surgery & Medicine* 20 (3): 310-8.
Majaron, B., S. M. Srinivas, et al. (2000). "Deep coagulation of dermal collagen with repetitive Er: YAG laser irradation." *Lasers in Surgery and Medicine* 26(2): 215-222.
Mansuripur, M. (1991). "Effects of High-Numerical-Aperture Focusing on the State of Polarization in Optical and Magnetoopic Data Storage Systems." *Applied Optics* 30(22): 3154-3162.
Marshall, G. W., S. J. Marshall, et al. (1997). "The dentin substrate: structure and properties related to bonding." *Journal of Dentistry* 25(6): 441-458.
Martin, P. (1997). "Wound healing—Aiming for perfect skin regeneration." *Science* 276 (5309): 75-81.
Martinez, O. E. (1987). "3000 Times Grating Compressor with Positive Group-Velocity Dispersion—Application to Fiber Compensation in 1.3-1.6 Mu-M region." *Ieee Journal of Quantum Electronics* 23(1): 59-64.
Martinez, O. E., J. P. Gordon, et al. (1984). "Negative Group-Velocity Dispersion Using Refraction." *Journal of the Optical Society of America a-Optics Image Science and Vision* 1(10): 1003-1006.
McKinney, J. D., M. A. Webster, et al. (2000). "Characterization and imaging in optically scattering media by use of laser speckle and a variable-coherence source." *Optics Letters* 25(1): 4-6.
Miglior, A., M. Casula, et al. (2001). "Clinical ability of Heidelberg retinal tomograph examination to detect glaucomatous visual field changes." *Ophthalmology* 108 (9): 1621-7.
Milner, T. E., D. M. Goodman, et al. (1996). "Imaging laser heated subsurface chromophores in biological materials: Determination of lateral physical dimensions." *Physics in Medicine in Biology* 41(1): 31-44.
Milner, T. E., D. M. Goodman, et al. (1995). "Depth Profiling of Laser-Heated Chromophores in Biological Tissues by Pulsed Photothermal Radiometry." *Journal of the Optical Society of America a-Optics Image Science and Vision* 12 (7): 1479-1488.
Milner, T. E., D. J. Smithies, et al. (1996). "Depth determination of chromophores in human skin by pulsed photothermal radiometry." *Applied Optics* 35(19): 3379-3385.
Mishchenko. M. I. and J. W. Hovenier (1995). "Depolarization of Light Backscattered by Randomly Oriented Nonspherical Particles." *Optics Letters* 20(12): 1356-&.
Mistlberger, A., J. M. Liebermann, et al. (1999). "Heidelberg retinal tomography and optical coherence tomography in normal, ocular-hypertensive, and glaucomatous eyes." *Ophthalmology* 106(10): 2027-32.
Mitsui, T. (1999). "High-speed detection of ballistic photons propatating through suspensions using spectral interferometry." *Japanese Journal of Applied Physics* Part 1—Regular Papers Short Notes & review Papers 38(5A): 2978-2982.
Molteno, A. C., N. J. Bosma, et al. (1999). "Otago glaucoma surgery outcome study: long-term results of trabeculectomy—1976 to 1995." *Ophthalmology* 106(9): 1742-50.
Morgener, U., W. Drexler, et al. (2000). "Spectroscopic optical coherence tomography." *Optics Letters* 25(2): 111-113.
Morgener, U., F. X. Kartner, et al. (1999) . "Sub-two-cycle pulses from a Kerr-lens mode-locked Ti : sapphire laser (vol. 24, p. 411, 1999)." *Optics Letters* 24(13): 920-920.
Mourant, J. R., A. H. Hielscher, et al. (1998). "Evidence of intrinsic differences in the light scattering properties of tumorigenic and nontumorigenic cells." *Cancer Cytopathology* 84(6): 366-374.
Muller, M., J. Squier, et al. (1998). "Dispersion pre-compensation of 15 femtosecond optical pulses for high-numerical-aperture objectives." *Journal of Microscopy-Oxford* 191: 141-150.
Muscat, S., N. McKay, et al. (2002). "Repeatability and reproducibility of corneal thickness measurements by optical coherence tomography." *Investigative Ophthalmology & Visual Science* 43(6): 1971-5.
Musch, D. C., P. R. Lichter, et al. (1999). "The Collaborative Initial Glaucoma Treatment Study. Study Design, Methods, and Baseline Characteristics of Enrolled Patients." *Ophthalmology* 106: 653-662.
Neerken, S., Lucassen, G. W., Bisschop, M.A., Lenderink, E., Nuijs, T.A.M. (2004). "Characterization of age-related effects in human skin: A comparative study that applies confocal laser scanning microscopy and optical coherence tomography." *Journal of Biomedical Optics* 9(2): 274-281.
Nelson, J. S., K. M. Kelly, et al. (2001). "Imaging blood flow in human port-wine stain in situ and in real time using optical Doppler tomography." *Archives in Dermatology* 137(6): 741-744.
Newson T. P., F. Farashi, et al. (1988). "Combined Interferometric and Polarimetric Fiber Optic Temperature Sensor with a Short Coherence Length Source." *Optics Communications* 68(3): 161-165.
November, L. J. (1993). "Recovery of the Matrix Operators in the Similarity and Congruency Transformations—Applications in Polarimetry." *Journal of the Optical Society of America a-Optics Image Science and Vision* 10(4): 719-739.
Oh, W. Y., S. H. Yun, et al. (2005). "Wide tuning range wavelength-swept laser with two semiconductor optical amplifiers." *Ieee Photonics Technology Letters* 17(3): 678-680.
Oka, K. and T. Kato (1999). "Spectroscopic polarimetry with a channeled spectrum." *Optics Letters* 24(21): 1475-1477.
Okugawa, T. and K. Rotate (1996). "Real-time optical image processing by synthesis of the coherence function using real-time holography." *Ieee Photonics Technology Letters* 8(2): 257-259.
Oshima, M., R. Torii, et al. (2001). "Finite element simulation of blood flow in the cerebral artery." *Computer Methods in Applied Mechanics and Engineering* 191 (6-7): 661-671.
Pan, Y. T., H. K. Xie, et al. (2001). "Endoscopic optical coherence tomography based on a microelectromechanical mirror." *Optics Letters* 26(24): 1966-1968.
Parisi, V., G. Manni, et al. (2001). "Correlation between optical coherence tomography, pattern electroretinogram, and visual evoked potentials in open-angle glaucoma patients." *Ophthalmology* 108(5): 905-12.
Park, B. H., M. C. Pierce, et al. (2005). "Real-time fiber-based multi-functional spectral-domain optical coherence tomography at 1.3 mu m." *Optics Express* 13(11): 3931-3944.
Park, D. H., J. W. Hwang, et al. (1998). "Use of laser Doppler flowmetry for estimation of the depth of burn." *Plastic and Reconstructive Surgery* 101(6): 1516-1523.
Pendry, J. B., A. J. Holden, et al. (1999). "Magnetism from conductors and enhanced nonlinear phenomena." *Ieee Transactions on Microwave Theory and Techniques* 47(11): 2075-2084.
Penninckx, D. and V. Morenas (1999). "Jones matrix of polarization mode dispersion." *Optics Letters* 24(13): 875-877.
Pierce, M. C., M. Shishkov, et al. (2005). "Effects of sample arm motion in endoscopic polarization-sensitive optical coherence tomography." *Optics Express* 13(15): 5739-5749.
Pircher, M., E. Gotzinger, et al. (2003). "Measurement and imaging of water concentration in human cornea with differential absorption optical coherence tomography." *Optics Express* 11(18): 2190-2197.
Pircher, M., E. Gotzinger, et al. (2003). "Speckle reduction in optical coherence tomography by frequency compounding." *Journal of Biomedical Optics* 8(3): 565-569.
Podoleanu, A. G., G. M. Dobre, et al. (1998). "En-face coherence imaging using galvanometer scanner modulation." *Optics Letters* 23(3): 147-149.
Podoleanu, A. G. and D. A. Jackson (1999). "Noise analysis of a combined optical coherence tomograph and confocal scanning ophthalmoscope." *Applied Optics* 38(10): 2116-2127.
Podoleanu, A. G., J. A. Rogers, et al. (2000). "Three dimensional OCT images from retina and skin." *Optics Express* 7(9): 292-298.
Podoleanu, A. G., M. Seeger, et al. (1998). "Transversal and longitudinal images from the retina of the living eye using low coherence reflectomtry."*Journal of Biomedical Optics* 3(1): 12-20.
Poole, C. D. (1988). "Statistical Treatment of Polarization Dispersion in Single-Mode Fiber." *Optics Letters* 13(8): 687-689.
Povazay, B., K. Bizheva, et al. (2002). "Submicrometer axial resolution optical coherence tomography." *Optics Letters* 27(20): 1800-1802.

Qi, B., A. P. Himmer, et al. (2004). "Dynamic focus control in high-speed optical coherence tomography based on a microelectromechanical mirror." *Optics Communications* 232(1-6): 123-128.
Radhakrishnan, S., A. M. Rollins, et al. (2001). "Real-time optical coherence tomography of the anterior segment at 1310 nm." *Archives of Ophthalmology* 119(8): 1179-1185.
Rogers, A. J. (1981). "Polarization-Optical Time Domain Reflectometry—a Technique for the Measurement of Field Distributions." Applied Optics 20(6): 1060-1074.
Rollins, A. M. and J. A. Izatt (1999). "Optimal interferometer designs for optical coherence tomography." *Optics Letters* 24(21): 1484-1486.
Rollins, A. M., R. Ung-arunyawee, et al. (1999). "Real-time in vivo imaging in human gastrointestinal ultrastructure by use of endoscopic optical coherence tomography with a novel efficient interferometer design." *Optics Letters* 24(19): 1358-1360.
Rollins, A. M., S. Yazdanfar, et al. (2002). "Real-time in vivo colors Doppler optical coherence tomography." *Journal of Biomedical Optics* 7(1): 123-129.
Rolllins, A. M., S. Yazdanfar, et al. (2000). "Imaging of human retinal hemodynamics using color Doppler optical coherence tomography." *Investigative Ophthalmology & Visual Science* 41(4): S548-S548.
Sandoz, P. (1997). "Wavelet transform as a processing tool in white-light interferometry." *Optics Letters* 22(14): 1065-1067.
Sankaran, V., M. J. Everett, et al. (1999). "Comparison of polarized-light propagation in biological tissue and phantoms." *Optics Letters* 24(15): 1044-1046.
Sankaran, V., J. T. Walsh, et al. (2000). "Polarized light propagation through tissue phantom, ehms containing densely packed scatterers." *Optics Letters* 25(4): 239-241.
Sarunic, M. V., M. A. Choma, et al. (2005). "Instantaneous complex conjugate resolved spectral domain and swept-source OCT using 3×3 couplers." *Optics Express* 13(3): 957-967.
Sathyam, U. S., B. W. Colston, et al. (1999). "Evaluation of optical coherence tomography quantitation of analytes in turbid media by use of two wavelengths." *Applied Optics* 38(10): 2097-2104.
Schmitt, J. M. (1997). "Array detection for speckle reduction in optical coherence microscopy." *Physics in Medicine and Biology* 42(7): 1427-1439.
Schmitt, J. M. (1999). "Optical coherence tomography (OCT): A review." *Ieee Journal of Selected Topics in Quantum Electronics* 5(4): 1205-1215.
Schmitt, J. M. and A. Knuttel (1997). "Model of optical coherence tomography of heterogeneous tissue." *Journal of the Optical Society of America a-Optics Image Science and Vision* 14(6): 1231-1242.
Schmitt, J. M., S. L. Lee, et al. (1997). "An optical coherence microscope with enhanced resolving power in thick tissue." *Optics Communications* 142(4-6): 203-207.
Schmitt, J. M., S. H. Xiang, et al. (1998). "Differential absorption with optical coherence tomography." *Journal of the Optical Society of America a-Optics Image Science and Vision* 15(9): 2288-2296.
Schmitt, J. M., S. H. Xiang, et al. (1999). "Speckle in optical coherence tomography." *Journal of Biomedical Optics* 4(1): 95-105.
Schmitt, J. M., M. J. Yadlowsky, et al. (1995). "Subsurface Imaging of Living Skin with Optical Coherence Microscopy." *Dermatology* 191(2): 93-98.
Shi, H., J. Finlay, et al. (1997). "Multiwavelength 10-GHz picosecond pulse generation from a single-stripe semiconductor diode laser." *Ieee Photonics Technology Letters* 9(11): 1439-1441.
Shi. H., I. Nitta, et al. (1999). "Demonstration of phase correlation in multiwavelength mode-locked semiconductor diode lasers." *Optics Letters* 24(4): 238-240.
Simon, R. (1982). "The Connection between Mueller and Jones Matrices of Polarization Optics." *Optics Communications* 42(5): 293-297.
Smithies, D. J., T. Lindmo, et al. (1998). "Signal attenuation and localization in optical coherence tomography studied by Monte Carlo simulation." *Physics in Medicine and Biology* 43(10): 3025-3044.
Sorin, W. V., and D. F. Gray (1992). "Simultaneous Thickness and Group Index Measurement Using Optical Low-Coherence Reflectometry." *Ieee Photonics Technology Letters* 4(1): 105-107.
Sticker, M., C. K. Hitzenberger, et al. (2001). "Quantitative differential phase measurement and imaging in transparent and turbid media by optical coherence tomography." *Optics Letters* 26(8): 518-520.
Sticker, M., M. Pircher, et al. (2002). "En face imaging of single cell layers by differential phase-contrast optical coherence microscopy." *Optics Letters* 27(13): 1126-1128.
Stoller, P., B. B. M. Kim, et al. (2002). "Polarization-dependent optical second-harmonic imaging of a rat-tail tendon." *Journal of Biomedical Optics* 7(2): 205-214.
Sun, C. S. (2003). "Multiplexing of fiber-optic acoustic sensors in Michelson interferometer configuration." *Optics Letters* 28(12): 1001-1003.
Swanson, E. A., J. A. Izatt, et al. (1993). "In-Vivo Retinal Imaging by Optical Coherence Tomography." *Optics Letters* 18(21): 1864-1866.
Takada, K., A. Himeno, et al. (1991). "Phase-Noise and Shot-Noise Limited Operations of Low Coherence Optical-Time Domain Reflectometry." *Applied Physics Letters* 59(20): 2483-2485.
Takenaka, H. (1973). "Unified Formalism for Polarization Optics by Using Group-Theory I (Theory)," *Japanese Journal of Applied Physics* 12(2): 266-231.
Tanno, N., T. Ichimura, et al. (1994). "Optical Multimode Frequency-Domain Reflectometer." *Optics Letters* 19(8): 587-589.
Tan-no, T. Ichumura, et al. (1994). "Optical Multitude Frequency-Domain Reflectometer." *Optics Letters* 19(8): 587-589.
Targowski, P., M. Wojtkowski, et al. (2004). "Complex spectral OCT in human eye imaging in vivo." *Optics Communications* 229(1-6): 79-84.
Tearney, G. J., S. A. Boppart, et al. (1996). "Scanning single-mode fiber optic catheter- endoscope for optical coherence tomography (vol. 21, p. 543, 1996)." *Optics Letters* 21(12): 912-912.
Tearney, G. J., B. E. Bouma, et al. (1996). "Rapid acquisition of in vivo biological images by use of optical coherence tomography." *Optics Letters* 21(17): 1408-1410.
Tearney, G. J., B. E. Bouma, et al. (1997). "In vivo endoscopic optical biopsy with optical coherence tomography." *Science* 276(5321): 2037-2039.
Tearney, G. J., M. E. Brezinski, et al. (1996). "Catheter-based optical imaging of a human coronary artery." *Circulation* 94(11): 3013-3013.
Tearney, G. J., M. E. Brezinski, et al. (1997). "In vivo endoscopic optical biopsy with optical coherence tomography." *Science* 276(5321): 2037-9.
Tearney, G. J., M. E. Brezinski, et al. (1997). "Optical biopsy in human gastrointestinal tissue using optical coherence tomography." *American Journal of Gastroenterology* 92(10): 1800-1804.
Tearney, G. J., M. E. Brezinski, et al. (1995). "Determination of the refractive index of highly scattering human tissue by optical coherence tomography." *Optics Letters* 20(21): 2258-2260.
Tearney, G. J., I. K. Jang, et al. (2000). "Porcine coronary imaging in vivo by optical coherence tomography." *Acta Cardiologica* 55(4): 233-237.
Tearney, G. J., R. H. Webb, et al. (1998). "Spectrally encoded confocal microscopy." *Optics Letters* 23(15): 1152-1154.
Tearney, G. J., H. Yabushita, et al. (2003). "Quantification of macrophage content in atherosclerotic plaques by optical coherence tomography." *Circulation* 107(1): 113-119.
Tower, T. T. and R. T. Tranquillo (2001). "Alignment maps of tissues: I. Microscopic elliptical polarimetry." *Biophysical Journal* 81(5): 2954-2963.
Tower, T. T. and R. T. Tranquillo (2001). "Alignment maps of tissues: II. Fast harmonic analysis for imaging." *Biophysical Journal* 81(5): 2964-2971.
Troy, T. L. and S. N. Thennadil (2001). "Optical properties of human skin in the near infrared wavelength range of 1000 to 2200 nm." *Journal of Biomedical Optics* 6 (2): 167-176.
Vabre, L., A. Dubois, et al. (2002). "Thermal-light full-field optical coherence tomography." *Optics Letters* 27(7): 530-532.
Vakhtin, A. B., D. J. Kane, et al. (2003). "Common-path interferometer for frequency-domain optical coherence tomography." *Applied Optics* 42(34): 6953-6958.
Vakhtin, A. B., K. A. Peterson, et al. (2003. "Differential spectral interferometry: an imaging technique for biomedical applications," *Optics Letters* 28(15): 1332-1334.

Vakoc, B. J., S. H. Yun, et al. (2005). "Phase-resolved optical frequency domain imaging." *Optics Express* 13(14): 5483-5493.
van Leeuwen, T. G., M. D. Kulkami, et al. (1999). "High-flow-velocity and shear-rate imaging by use of color Doppler optical coherence tomography." *Optics Letters* 24(22): 1584-1586.
Vansteenkiste, N., P. Vignolo, et al. (1993). "Optical Reversibility Theorems for Polarization—Application to Remote-Control of Polarization," *Journal of the Optical Society of America a-Optics Image Science and Vision* 10(10): 2240-2245.
Vargas, O., E. K. Chan, et al. (1999). "Use of an agent scattering in skin." *Lasers in Surgery and Medicine* 24(2): 133-141.
Wang, R. K. (1999). "Resolution improved optical coherence-gated tomography for imaging through biological tissues." *Journal of Modern Optics* 46(13): 1905-1912.
Wang, X. J., T. E. Milner, et al. (1997). "Measurement of fluid-flow-velocity profile in turbid media by use of optical Doppler tomography." *Applied Optics* 36(1): 144-149.
Wang, X. J., T. E. Milner, et al. (1995). "Characterization of Fluid-flow Velocity by Optical Doppler Tomography." *Optics Letters* 20(11): 1337-1339.
Wang, Y. M., J. S. Nelson, et al. (2003). "Optimal wavelength for ultrahigh-resolution optical coherence tomography." *Optics Express* 11(12): 1411-1417.
Wang, Y. M., Y. M. Zhao, et al. (2003). "Ultrahigh-resolution optical coherence tomography by broadband continuum generation from a photonic crystal fiber." *Optics Letters* 28(3): 182-184.
Watkins, L. R., S. M. Tan, et al. (1999). "Determination of interfererometer phase distributions by use of wavelets." *Optics Letters* 24(13): 905-907.
Wetzel, J. (2001). "Optical coherence tomography in dermatology: a review." *Skin Research and Technology* 7(1): 1-9.
Wentworth, R. H. (1989). "Theoretical Noise Performance of Coherence-Multiplexed Interferometric Sensors." *Journal of Lightwave Technology* 7(6): 941-956.
Westphal, V., A. M. Rollins, et al. (2002). "Correction of geometric and refractive image distortions in optical coherence tomography applying Fermat's principle." *Optics Express* 10(9): 397-404.
Westphal, V., S. Yazdanfar, et al. (2002). "Real-time, high velocity-resolution color Doppler optical coherence tomography." *Optics Letters* 27(1): 34-36.
Williams, P. A. (1999). "Rotating-wave-plate Stokes polarimeter for differential group delay measurements of polarization-mode dispersion." *Applied Optics* 38(31): 6508-6515
Wojtkowski, M., T. Bajrazewski, et al. (2003). "Real-time in vivo imaging by high-speed spectral optical coherence tomography." *Optics Letters* 28(19): 1745-1747.
Wojtkowski, M., A. Kowalczyk, et al. (2002). "Full range complex spectral optical coherence tomography technique in eye imaging." *Optics Letters* 27(16): 1415-1417.
Wojtkowski, M., R. Leitgeb, et al. (2002). "In vivo human retinal imaging by Fourier domain optical coherence tomography." *Journal of Biomedical Optics* 7(3): 457-463.
Wojtkowski, M., R. Leitgeb, et al. (2002). "Fourier domain OCT imaging of the human eye in vivo." *Proc. SPIE* 4619: 230-236.
Wojtkowski, M., V. J. Srinivasan, et al. (2004). "Ultrahigh-resolution, high-speed, Fourier domain optical coherence tomography and methods for dispersion compensation." *Optics Express* 12(11): 2404-2422.
Wong, B. J. F., Y. H. Zhao, et al. (2004). "Imaging the internal structure of the rat cochlea using optical coherence tomography at 0.827 mu m and 1.3 mu m." *Otolaryngology—Head and Neck Surgery* 130(3): 334-338.
Yang, C., A. Wax, et al. (2001). "Phase-dispersion optical tomography."*Optic Letters* 26(10): 686-688.
Yang, C., Wax, et al. (2001). "Phase-referenced interferometer with subwavelength and subhertz sensitivity applied to the study of cell membrane dynamics." *Optics Letters* 26(16): 1271-1273.
Yang, C. H., A. Wax, et al. (2001). "Phase-dispersion optical tomography." *Optics Letters* 26(10): 686-688.
Yang, C. H., A. Wax, et al. (2000). "Interferometric phase-dispersion microscopy." *Optics Letters* 25(20): 1526-1528.
Yang, V. X. D., M. L. Gordon, et al. (2002). "Improved phase-resolved optical Doppler tomography using the Kasai velocity estimator and histogram segmentation." Optics Communications 208(4-6): 209-214.
Yang, V. X. D., M. L. Gordon, et al. (2003). "High speed, wide velocity dynamic range Doppler optical coherence tomography (Part I): System design, signal processing, and performance." *Optics Express* 11(7): 794-809.
Yang, V. X. D., M. L. Gordon, et al. (2003). "High speed, wide velocity dynamic range Doppler optical coherence tomography (Part II): Imaging in vivo cardiac dynamics of *Xenopus laevis." Optics Express* 11(14): 1650-1658.
Yang, V. X. D., M. L. Gordon, et al. (2003). "High speed, wide velocity dynamic range Doppler optical coherence tomography (Part III): in vivo endoscopic imaging of blood flow in the rates and human gastrointestinal tracts." *Optics Express* 11(19): 2416-2424.
Yang, V. X. D., B. Qi, et al. (2003). "In vivo feasibility of endoscopic catheter-based Doppler optical coherence tomography." *Gastroenterology* 124(4): A49-A50.
Yao, G. and L. H. V. Wang (2000). "Theoretical and experimental studies of ultrasound-modulated optical tomography in biological tissue." *Applied Optics* 39(4): 659-664.
Yazdanfar, S. and J. A. Izatt (2002). "Self-reference Doppler optical coherence tomography." *Optics Letters* 27(23): 2085-2087.
Yazdanfar, S., M. D. Kulkarni, et al. (1997). "High resolution imaging of in vivo cardiac dynamics using color Doppler optical coherence tomography." *Optics Express* 1 (13): 424-431.
Yazdanfar, S., A. M. Rollins, et al. (2000). "Imaging and velocimetry of the human retinal circulation with color Doppler optical coherence tomography." *Optics Letters* 25(19): 1448-1450.
Yazdanfar, S., A. M. Rollins, et al. (2000). "Noninvasive imaging and velocimetry of human retinal blood flow using color Doppler optical coherence tomography" *Investigative Ophthalmology & Visual Sciences* 41(4): S548-S548.
Yazdanfar, S., A. M. Rollins, et al. (2003). "In vivo imaging of human retinal flow dynamics in color Doppler optical coherence tomography." *Archives of Ophthalmology* 121(2): 235-239.
Yazdanfar, S., C. H. Yang, et al. (2005). "Frequency estimation precision in Doppler optical coherence tomography using the Cramer-Rao lower bound." *Optics Express* 13(2): 410-416.
Yun, S. H., C. Boudoux, et al. (2004). "Extended-cavity semiconductor wavelength- swept laser for biomedical imaging." *Ieee Photonics Technology Letters* 16(1): 293-295.
Yun, S. H., C. Boudoux, et al. (2003). "High-speed wavelength-swept semiconductor laser with polygon-scanner-based wavelength filter." *Optics Letters* 28(20): 1981-1983.
Yun, S. H., G. J. Tearney, et al. (2004). "Pulsed-source and swept-source spectral-domain optical coherence tomography with reduced motion artifacts." *Optics Express* 12(23): 5414-5624.
Yun, S. H., G. J. Tearney, et al. (2004). "Removing the depth-degeneracy in optical frequency domain imaging with frequency shifting." *Optics Express* 12(20): 4822-4828.
Yun, S. H., G. J. Tearney, et al. (2004). "Motion artifacts in optical coherence tomography with frequency-domain ranging." *Optics Express* 12(13): 2977-2998.
Zhang, J., J. S. Nelson, et al. (2005). "Removal of a mirror image and enhancement of the signal-to-noise ratio in Fourier-domain optical coherence tomography using an elctro-optic phase modulator."*Optics Letters* 30(2): 147-149.
Zhang, Y., M. Sato, et al. (2001). "Numerical investigations of optimal synthesis of several low coherence sources for resolution improvements." *Optics Communications* 192(3-6): 183-192.
Zhang, Y., M. Sato, et al. (2001). "Resolution improvement in optical coherence tomography by optical synthesis of light-emitting diodes." *Optics Letters* 26(4): 205-207.
Zhao, Y., Z. Chen, et al. (2002). "Real-time phase-resolved functional optical coherence tomography by use of optical Hilbert transformation." *Optics Letters* 27(2): 98-100.
Zhao, Y. H., Z. P. Chen, et al. (2000). "Doppler standard deviation imaging for clinical monitoring of in vivo human skin blood flow." *Optics Letters* 25(18): 1358-1360.
Zhao, Y. H., Z. P. Chen, et al. (2000). "Phase-resolved optical coherence tomography and optical Doppler tomography for imaging blood flow in human skin with fast scanning speed and high velocity sensitivity." *Optics Letters* 25(2): 114-116.

Zhou, D., P. R. Prucnal, et al. (1998). "A widely narrow linewidth semiconductor fiber laser." *IEEE Photonics Technology Letters* 10(6): 781-783.
Zuluaga, A. F. and R. Richards-Kortum (1999). "Spatially resolved spectral interferometry for determination of subsurface structure ." *Optics Letters* 24(8): 519-521.
Zvyagin, A. V., J. B. FitzGerald, et al. (2000). "Real-time detection technique for Doppler optical coherence tomography." *Optics Letters* 25(22): 1645-1647.
Marc Nikles et al., "Brillouin gain spectrum characterization in single-mode optical fibers", *Journal of Lightwave Technology* 1997, 15 (10): 1842-1851.
Tsuyoshi Sonehara et al., "Forced Brillouin Spectroscopy Using Frequency-Tunable Continuous-Wave Lasers", *Physical Review Letters* 1995, 75 (23): 4234-42373.
Hajime Tanaka et al., "New Method of Superheterodyne Light Beating Spectroscopy for Brillouin-Scattering Using Frequency-Tunable Lasers", *Physical Review Letters* 1995, 74 (9): 1609-1612.
Webb RH et al. "Confocal Scanning Laser Ophthalmoscope", *Applied Optics* 1987, 26 (8): 1492-1499.
Andreas Zumbusch et al. "Three-dimensional vibrational imaging by coherent anti-Stokes Raman scattering", *Physical Review Letters* 1999, 82 (20): 4142-4145.
Katrin Kneipp et al., "Single molecule detection using surface-enhanced Raman scattering (SERS)", *Physical Review Letters* 1997, 78 (9): 1667-1670.
K.J. Koski et al., "Brillouin imaging" *Applied Physics Letters* 87, 2005.
Boas, et al., "Diffusing temporal light correlation for burn diagnosis", *SPIE*, 1999, 2979:468-477.
David J. Briers, "Speckle fluctuations and biomedical optics: implications and applications", *Optical Engineering*, 1993, 32 (2):277-283.
Clark, et al., "Tracking Speckle Patterns with Optical Correlation", *SPIE*, 1992 1772:77-87.
Facchini et al., "An endoscopic system for DSPI", *Optik*, 1993, 95(1):27-30.
Hrabovsky, M., "Theory of speckle displacement and decorrelation: application in mechanics", *SPIE*, 1998, 3479:345-354.
Sean J. Kirkpatrick et al., "Micromechanical behavior of cortical bone and inferred from laser speckle data", *Journal of Biomedical Materials Research*, 1998, 39(3):373-379.
Sean J. Kirkpatrick et al., "Laser speckle microstain measurements in vascular tissue", *SPIE*, 1999, 3598:121-129.
Loree et al., "Mechanical Properties of Model Atherosclerotic Lesion Lipid Pools", *Aterioscleroses and Thrombosis*, 1994, 14(2):230-234.
Podbielska, H. "Interferometric Methods and Biomedical Research", *SPIE*, 1999, 2732:134-141.
Richards-Kortum et al., "Spectral diagnosis of atherosclerosis using an optical fiber laser catheter", *American Heart Journal*, 1989, 118(2):381-391.
Ruth, B. "blood flow determination by the laser speckle method", *Int J Microcirc: Clin Exp*, 1990, 9:21-45.
Shapo et al., "Intravascular strain imaging: Experiments on an Inhomogeneous Phantom", *IEEE Ultrasonics Symposium* 1996, 2:1177-1180.
Shapo et al., "Ultrasonic displacement and strain imaging of coronary arteries with a catheter array", *IEEE Ultrasonics Symposium* 1995, 2:1511-1514.
Thompson et al., "Imaging in scattering media by use of laser speckle", *Opt. Soc. Am. A.,* 1997, 14(9):2269-2277.
Thompson et al., "Diffusive media characterization with laser speckle", *Applied Optics*, 1997, 36(16):3726-3734.
Tuchin, Valery V., "Coherent Optical Techniques for the Analysis of Tissue Structure and Dynamics," *Journal of Biomedical Optics* 1999, 4(1): 106-124.
M. Wussling et al., "Laser diffraction and speckling studies in skeletal and heart musle", *Biomed, Biochim, Acta*, 1986, 45(1/2): S 23-S 27.
T. Yoshimura et al., "Statistical properties of dynamic speckles", *J. Opt. Soc. Am A.* 196, 3(7):1032-1054.
Zimnyakov et al., "Spatial speckle correlometry in applications to tissue structure monitoring", *Applied Optics* 1997, 36(22): 5594-5607.
Zimnyakov et al., "A study of statistical properties of partially developed speckle fields as applied to the diagnosis of structural changes in human skin", *Optics and Spectroscopy*, 1994, 76(5): 747-753.
Zimnyakov et al., "Speckle patterns polarization analysis as an approach to turbid tissue structure monitoring", *SPIE* 1999, 2981:172-180.
Ramasamy Manoharan et al., "Biochemical analysis and mapping of atherosclerotic human artery using FT-IR microspectroscopy", *Atherosclerosis*, May 1993, 181-1930.
N. V. Salunke et al., "Biomechanics of Atherosclerotic Plaque" *Critical Reviews™ in Biomedical Engineering* 1997, 25(3):243-285.
D. Fu et al., "Non-invasive quantitative reconstruction of tissue elasticity using an iterative forward approach", Phys. Med. Biol. 2000 (45): 1495-1509.
S.B. Adams Jr. et al., "The use of polarization sensitive optical coherence tomography and elastography to assess connective tissue", Optical Soc. of American Washington 2002, p. 3.
Erdelyi et al. "Generation of diffraction-free beams for applications in optical microlithography", J. Vac. Sci Technol. B 15 (12), Mar./Apr. 1997, pp. 287-292.
Tearney, et al., "Spectrally encoded miniature endoscopy" Optical Society of America; Optical Letters vol. 27, No. 6, Mar. 15, 2002; pp. 412-414.
Yelin et al., "Double-clad Fiber for Endoscopy" Optical Society of America; Optical Letters vol. 29, No. 20, Oct. 16, 2005; pp. 2408-2410.
PCT International Preliminary Report on Patentability for International Application No. PCT/US2004/038404 dated Jun. 2, 2006.
Office Action dated Aug. 24, 2006 for U.S. Appl. No. 10/137,749.
Barry Cense et al., "Spectral-domain polarization-sensitive optical coherence tomography at 850nm", Coherence Domain Optical Methods and Optical Coherence Tomography in Biomedicine IX, 2005, pp. 159-162.
A. Ymeti et al., "Integration of microfluidics with a four-channel integrated optical Young interferometer immunosensor", Biosensors and Bioelectronics, Elsevier Science Publishers, 2005, pp. 1417-1421.
PCT International Search Report for Application No. PCT/US2006/018865 filed May 5, 2006.
International Written Opinion for International Patent application No. PCT/US2006/018865 filed May 5, 2006.
John M. Poneros, "Diagnosis of Barrett's esophagus using optical coherence tomography", Gastrointestinal Endoscopy clinics of North America, 14 (2004) pp. 573-588.
P.F. Escobar et al., "Diagnostic efficacy of optical coherence tomography in the management of preinvasive and invasive cancer of uterine cervix and vulva", Int. Journal of Gynecological Cancer 2004, 14, pp. 470-474.
Ko T et al., "Ultrahigh resolution in vivo versus ex vivo OCT imaging and tissue preservation", Conference on Lasers and electroptics, 2001, pp. 252-253.
Paul M. Ripley et al., "A comparison of Artificial Intelligence techniques for spectral classification in the diagnosis of human pathologies based upon optical biopsy", Journal of Optical Society of America, 2000, pp. 217-219.
Wolfgang Drexler et al., "Ultrahigh-resolution optical coherence tomography", Journal of Biomedical Optics Spie USA, 2004, pp. 47-74.
PCT International Search Report for Application No. PCT/US2006/016677 filed Apr. 28, 2006.
International Written Opinion for International Patent application No. PCT/US2006/016677 filed Apr. 28, 2006.
Office Action dated Nov. 13, 2006 for U.S. Appl. No. 10/501,268.
Office Action dated Nov. 20, 2006 for U.S. Appl. No. 09/709,162.
PCT International Search Report and Written Opinion for Application No. PCT/US2004/023585 filed Jul. 23, 2004.
Office Action dated Dec. 6, 2006 for U.S. Appl. No. 10/997,789.
Elliot, K. H. "The use of commercial CCD cameras as linear detectors in the physics undergraduate teaching laboratory", European Journal of Physics 19, 1998, pp. 107-117.

Lauer, V. "New approach to optical diffraction tomography yielding a vector equation of diffraction tomography and a novel tomographic microscope", Journal of Microscopy vol. 205, Issue 2, 2002, pp. 165-176.
Office Action dated Dec. 18, 2006 for U.S. Appl. No. 10/501,276.
Devesa, Susan S. et al. (1998) "Changing Pattern in the Incidence of Esophegeal and Gastric Carcinoma in the United States." *American Cancer Society* vol. 83, No. 10, pp. 2049-2053.
Barr, H et al. (2005) "Endoscopic Therapy for Barrett's Oesophaugs" *Gut* vol. 54:875-884.
Johnston, Mark H.(2005) "Technology Insight: Ablative Techniques for Barrett's Esophagus—Current and Emerging Trends" , www.Nature.com/clinicalpratice/gasthep.
Falk, Gary W. et al. (1997) "Surveillance of Patients with Barrett's Esophagus for Dysplasia and Cancer with Balloon Cytology" *Gastroenterology* vol. 112, pp. 1787-1797.
Sepchler, Stuart Jon. (1997) "Barrett's Esophagus: Should We Brush off this Ballooning Problem?" *Gastroenterology* vol. 112, pp. 2138-2152.
Froehly, J. et al. (2003) "Multiplexed 3D Imaging Using Wavelength Encoded Spectral Interferometry: A Proof of Principle" *Optics Communications* vol. 22, pp. 127-136.
Kubba A.K. et al. (1999) "Role of p53 Assessment in Management of Barrett's Esophagus" *Digestive Disease and Sciences* vol. 44, No. 4. pp. 659-667.
Reid, Brian J. (2001) "p53 and Neoplastic Progression in Barrett's Esophagus" *The American Journal of Gastroenterology* vol. 96, No. 5, pp. 1321-1323.
Sharma, P. et al.(2003) "Magnification Chromoendoscopy for the Detection of Intestinal Metaplasia and Dysplasia in Barrett's Oesophagus" *Gut* vol. 52, pp. 24-27.
Kuipers E.J. et al. (2005) "Diagnostic and Therapeutic Endoscopy" *Journal of Surgical Oncology* vol. 92, pp. 203-209.
Georgakoudi, Irene et al. (2001) "Fluorescence, Reflectance, and Light-Scattering Spectroscopy for Evaluating Dysplasia in Patients With Barrett's Esophagus" *Gastroenterology* vol. 120, pp. 1620-1629.
Adrian, Alyn L. et al. (1997) "High-Resolution Endoluminal Sonography is a Sensitive Modality for the Identification of Barrett's Meaplasia" *Gastrointestinal Endoscopy* vol. 46, No. 2, pp. 147-151.
Canot, Marcia Irene et al (1999) "Vital Staining and Barrett's Esophagus" *Gastrointestinal Endoscopy* vol. 49, No. 3, part 2, pp. 12-16.
Evans, John A.. et al. (2006) "Optical Coherence Tomography to Identify Intramucosal Carcinoma and High-Grade Dysplasia in Barrett'Esophagus" *Clinical Gastroenterology and Hepatology* vol. 4, pp. 38-43.
Poneros, John M. et al. (2001) "Diagnosis of Specialized Intestinal Metaplasia by Optical Coherence Tomography" *Gastroenterology* vol. 120, pp. 7-12.
Ho. W. Y. et al. (2005) "115 KHz Tuning Repetition Rate Ultrahigh-Speed Wavelength-Swept Semiconductor Laser"*Optics Letters* col. 30, No. 23, pp. 3159-3161.
Brown, Stanley B. et al. (2004) "The Present and Future Role of Photodynamic Therapy in Cancer Treatment" *The Lancet Oncology* vol. 5, pp. 497-508.
Boogert, Jolanda Van Den et al. (1999) "Endoscopic Ablation Therapy for Barret's Esophagua with High-Grade Dysplasia: A Review" *The American Journal of Gastroenterology* vol. 94, No. 5, pp. 1153-1160.
Sampliner, Richard E. et al. (1996) "Reversal of Barrett's Esophagus with Acid Suppression and Multipolar Electrocoagulation: Preliminary Results" *Gastrointestinal Endoscopy* vol. 44, No. 5, pp. 532-535.
Sampliner, Richard E. (2002) "Endoscopic Ablative Therapy for Barrett's Esophagus: Current Status" *Gastrointestinal Endoscopy* vol. 59, No. 1, pp. 66-69.
Soetikno, Roy M. et al. (2003) "Endoscopic Mucosal resection" *Gastrointestinal Endoscopy* vol. 57, No. 4, pp. 567-579.
Ganz, Robert A. et al. (2004) "Complete Ablation of Esophageal Epithelium with a Balloon-based Bipolar Electrode: A Phased Evaluation in the Porcine and in the Human Esophagus" *Gastrointestinal Endoscopy* vol. 60, No. 6, pp. 1002-1010.
Pfefer, Jorje et al. (2006) "Performance of the Aer-O-Scope, A Pneumatic, Self Propelling, Self Navigating Colonoscopy in Animal Experiments" *Gastrointestinal Endoscopy* vol. 63, No. 5, pp. AB223.
Overholt, Bergein F. et al. (1999) "Photodynamic Therapy for Barrett'Esophagus: Follow-Up in 100 Patients" *Gastrointestinal Endoscopy* vol. 49, No. 1, pp. 1-7.
Vogel, Alfred et al. (2003) "Mechanism of Pulsed Laser Ablation of Biological Tissues" *American Chemical Society* vol. 103, pp. 577-644.
McKenzie, A. L. (1990) "Physics of Thermal Processes in Laser-Tissue Interaction" *Phys. Med. Biol* vol. 35, No. 9, pp. 1175-1209.
Anderson, R. Rox et al. (1983) "Selective Photothermolysis Precise Microsurgery by Selective Absorption of Pulsed Radiation" *Science* vol. 220, No. 4596, pp. 524-527.
Jacques, Stevens L. (1993) "Role of Tissue Optics and Pulsed Duration on Tissue Effects During High-Power Laser Irradiation" *Applied Optics* vol. 32, No. 13, pp. 2447-2454.
Nahen, Kester et al. (1999) "Investigations on Acoustic On-Line Monitoring of IR Laser Ablation of burned Skin" *Lasers in Surgery and Medicine* vol. 25, pp. 69-78.
Jerath, Maya R. et al. (1993) "Calibrated Real-Time Control of Lesion Size Based on Reflectance Images" *Applied Optics* vol. 32, No. 7, pp. 1200-1209.
Jerath, Maya R. et al (1992) "Dynamic Optical Property Changes: Implications for Reflectance Feedback Control of Photocoagulation" *Journal of Photochemical,.Photobiology, B: Biol* vol. 16, pp. 113-126.
Deckelbaum, Lawrence I. (1994) "Coronary Laser Angioplasty" *Lasers in Surgery and Medicine* vol. 14, pp. 101-110.
Kim, B.M. et al. (1998) "Optical Feedback Signal for Ultrashort Laser Pulse Ablation of Tissue" *Applied Surface Science* vol. 127-129, pp. 857-862.
Brinkman, Ralf et al. (1996) "Analysis of Cavitation Dynamics During Pulsed Laser Tissue Ablation by Optical On-Line Monitoring" *IEEE Journal of Selected Topics in Quantum Electronics* vol. 2, No. 4, pp. 826-835.
Whelan, W.M. et al. (2005) "A novel Strategy for Monitoring Laser Thermal Therapy Based on Changes in Optothermal Properties of Heated Tissues" *International Journal of Thermophyics* vol. 26, No. 1, pp. 233-241.
Thomsen, Sharon et al. (1990) "Microscopic Correlates of Macroscopic Optical Property Changes During Thermal Coagulation of Myocardium" *SPIE* vol. 1202, pp. 2-11.
Khan, Misban Huzaira et al. (2005) "Intradermally Focused Infrared Laser Pulses: Thermal Effects at Defined Tissue Depths" *Lasers in Surgery and Medicine* vol. 36, pp. 270-280.
Neumann, R.A. et al. (1991) "Enzyme Histochemical Analysis of Cell Viability After Argon Laser-Induced Coagulation Necrosis of the Skin" *Journal of the American Academy of Dermatology* vol. 25, No. 6, pp. 991-998.
Nadkarni, Seemantini K. et al. (2005) "Characterization of Atherosclerotic Plaques by Laser Speckle Imaging" *Circulation* vol. 112, pp. 885-892.
Zimnyakov, Dmitry A. et al. (2002) "Speckle-Contrast Monitoring of Tissue Thermal Modification" *Applied Optics* vol. 41, No. 28, pp. 5989-5996.
Morelli, J. G., et al (1986) "Tunable Dye Laser (577 nm) Treatment of Port Wine Stains" *Lasers in Surgery and Medicine* vol. 6, pp. 94-99.
French, P.M.W. et al. (1993) "Continuous-wave Mode-Locked $Cr^{4+}$: YAG Laser" *Optics Letters* vol. 18, No. 1, pp. 39-41.
Sennaroglu, Alphan at al. (1995) "Efficient Continuous-Wave Chromium-Doped YAG Laser" *Journal of Optical Society of America* vol. 12, No. 5, pp. 930-937.
Bouma, B et al. (1994) "Hybrid Mode Locking of a Flash-Lamp-Pumped Ti: $Al_2O_3$ Laser" *Optics Letters* vol. 19, No. 22, pp. 1858-1860.
Bouma, B et al. (1995) "High Resolution Optical Coherence Tomography Imaging Using a Mode-Locked Ti: $Al_2O_3$ Laser Source" *Optics Letters* vol. 20, No. 13, pp. 1486-1488.
Fernández, Cabrear Delia et al. "Automated detection of retinal layer structures on optical coherence tomography images" *Optics Express* vol. 13, No. 25, Oct. 4, 2005, pp. 10200-10216.
Ishikawa, Hiroshi et al. "Macular Segmentation with optical coherence tomography", Investigative Ophthalmology & Visual Science, vol. 46, No. 6, Jun. 2005, pp. 2012-2017.

* cited by examiner

*Prior Art*

*Prior Art*

SYSTEM AND METHOD FOR OPTICAL COHERENCE IMAGING

Matter enclosed in heavy brackets [ ] appears in the original patent but forms no part of this reissue specification; matter printed in italics indicates the additions made by reissue.

CROSS-REFERENCE TO RELATED APPLICATION(S)

The present invention claims priority from U.S. Patent Application Ser. No. 60/608,800 filed on Sep. 10, 2004, the entire disclosure of which incorporated herein by reference.

FIELD OF THE INVENTION

The present invention relates generally to optical coherence tomography imaging, and more particularly, to a system and method that uses optical coherence tomography that permits imaging of biological samples with high sensitivity and reduced artifacts, e.g., due to sample and probe motion.

BACKGROUND OF THE INVENTION

Image artifacts resulting from motion have been important issues of research in many medical imaging modalities because they may degrade the image quality and cause inaccurate clinical interpretation of images. Artifacts can arise when an object being imaged (sample) is moved during data acquisition but is assumed stationary in the image reconstruction process. In each imaging modality, motion artifacts can be present in different forms and with different magnitudes. Understanding basic motion effects in a particular imaging method is an essential step toward the development of techniques to avoid or compensate resulting artifacts. Optical interferometric imaging methods using frequency domain ranging have recently received considerable interest due to their high image acquisition speed and sensitivity.

Two frequency domain techniques have been demonstrated: spectral-domain optical coherence tomography (SD-OCT) as described in A. F. Fercher et al., "Measurements of intraocular distances by backscattering spectral interferometry," Opt. Comm. 117, 43-48 (1995), G. Hausler et al., "Coherence radar and spectral radar—new tools for dermatological diagnosis," J. Biomed. Opt. 3, 21-31 (1998), M. Wojtkowski et al., "Real time in vivo imaging by high-speed spectral optical coherence tomography," Opt. Lett. 28, 1745-1747 (2003), N. Nassif et al., "In-vivo human retinal imaging by ultra high-speed spectral domain optical coherence tomography," Opt. Lett. 29, 480-482 (2004), S. H. Yun et al., "High-speed spectral domain optical coherence tomography at 1.3 μm wavelength," Opt. Express 11, 3598-3604 (2003), and optical frequency domain imaging ("OFDI") S. R. Chinn, E. Swanson, and J. G. Fujimoto, "Optical coherence tomography using a frequency-tunable optical source," Opt. Lett. 22, 340-342 (1997), B. Golubovic et al., "Optical frequency-domain reflectometry using rapid wavelength tuning of a $Cr^{4+}$:forsterite laser," Opt. Lett. 22, 1704-1706 (1997), F. Lexer et al., "Wavelength-tuning interferometry of intraocular distances," Appl. Opt. 36, 6548-6553 (1997), S. H. Yun et al, "High-speed optical frequency-domain imaging," Opt. Express 11, 2953-2963 (2003), the entire disclosures of all of which are incorporated herein by reference. Using the SD-OCT technique, the spectral interference fringe can be measured in the spatial domain by means of a diffraction grating and a charge-coupled device ("CCD") array. In exemplary OFDI techniques, the spectral fringe is mapped to the time domain by use of a frequency-swept light source and measured with a photodetector as a function of time. In both methods; axial reflectance profile (A-line) is obtained by performing a discrete Fourier transform of the acquired data. Since the Fourier transform process involves integration of the entire data set obtained in single A-line period, the signal-to-noise ratio ("SNR") is enhanced relative to time domain ranging, as described in S. H. Yun et al., "High-speed optical frequency-domain imaging," Opt. Express 11, 2953-2963 (2003), R. Leitgeb, et al. "Performance of Fourier domain vs. time domain optical coherence tomography," Opt. Express 11, 889-894 (2003), J. F. de Boer et al., "Improved signal-to-noise ratio in spectral-domain compared with time-domain optical coherence tomography," Opt. Lett. 28, 2067-2069 (2003), and M. A. Choma et al., "Sensitivity advantage of swept source and Fourier domain optical coherence tomography," Opt. Express 11, 2183-2189 (2003), the entire disclosures of all of which are incorporated herein by reference This improvement in SNR is particularly advantageous for applications requiring high image acquisition rates such as screening for disease and surveillance of large tissue volumes. It is, however, possible that the integration effect enhances the sensitivity to sample motion because the motion-induced change in signal is also integrated over the entire A-line acquisition period.

Spectral-domain optical coherence tomography ("SD-OCT") makes use of low-coherence spectral interferometry to obtain cross-sectional images of a biological sample. Interference fringes as a function of wavelength are measured using a broadband light source and a spectrometer based on a charge-coupled-device ("CCD") camera. The axial reflectivity profile of a sample, or an A-line, can be obtained by a discrete Fourier transform of the camera readout data. This imaging technique has recently gone through rapid technical development to demonstrate high quality imaging of biological samples with fast image acquisition time, an order of magnitude faster than state-of-the-art time-domain OCT systems. The recent advancement in imaging speed may lead to the utilization of SD-OCT in a number of clinical applications in the near future.

The SD-OCT systems that have been used to date utilized either a continuous-wave ("cw") broad-spectrum light source, such as super luminescent diodes ("SLD"), or ultrashort mode-locked pulses with a high repetition rate in the range of 10-100 MHz. In both cases, the CCD array is generally illuminated constantly, and therefore the exposure time of the CCD camera determines the signal acquisition time for a single A-line. In this case, a path length change in the interferometer during image acquisition results in phase drift in the interference fringe. If the phase drifts over more than μ during a single A-line acquisition, the interference fringe can be completely erased, resulting in a degradation of SNR. This motion artifact can be caused by axial motion of a sample relative to the probe beam. By comparison, transverse sample motion or transverse beam scanning does not result in fringe washout. However, the transverse motion can result in degradation in transverse resolution and SNR. In medical imaging in vivo, the motion effects can arise from various sources. The main causes include patient motion, physiological phenomena such as cardiac motion, blood flow, pulsation, and catheter movement associated with beam scanning or uncontrolled movement of operator's hand. Furthermore, environmental changes such as mechanical vibration, sound waves, and temperature drift can alter the path length difference in the interferometer, resulting in SNR degradation through fringe washout. Considering that cameras appropriate for SD-OCT typically provide exposures times longer than 10 μs, a solution to the fringe washout problem will be required for biomedical applications where sample and probe motion is common.

Therefore, one of the objects of the present invention is to reduce or eliminate the motion artifacts.

SUMMARY OF THE INVENTION

According to the present invention, an imaging apparatus/system is provided which includes an optical source and at least one detector array. In one exemplary embodiment of the present invention, an optical source can emit a broadband spectrum in a pulsed mode, for example, by Q-switching or mode locking, with a pulse repetition rate preferably being equal to a readout rate of a detector array. The pulsed source can produce enough average optical power to provide sufficient signal to noise ratio required for imaging, while the relatively short duration of the output pulses results in an effective signal integration time substantially shorter than the detector's integration time, leading to high-sensitivity motion-artifact-free imaging. This pulsed-source approach may pertain to full-field optical coherence tomography and/or spectral-domain optical coherence tomography. In another exemplary embodiment of the present invention, the optical source is a wavelength-swept source emitting relatively narrowband spectrum swept over a wide range with a repetition rate preferably being equal to the readout rate of the detector array or A-line rate. This exemplary embodiment of the present invention allows the interference signal associated with each spectral component to be measured with an effective integration time substantially shorter than an A-line acquisition time. This exemplary scheme may also eliminate the fringe washout problem as in the prior art using continuous-wave broadband source or high-repetition mode-locked pulses. The above-described exemplary embodiments of the present invention may employ two or more detector arrays for dual-balanced detection and/or polarization diversity and further employ fiber-optic probes, allowing for medical imaging in vivo with high sensitivity, high speed, and the immunity from motion artifacts.

Accordingly, an exemplary embodiment of a system and method for imaging at least a portion of a sample are provided. In particular, at least one source electro-magnetic radiation can be generated and forwarded to the sample and a reference. A signal associated with a combination of at least one first electro-magnetic radiation received from the sample and at least one second electro-magnetic radiation received from the reference can be detected using at least one of a plurality of detectors. At least one particular detector can have a particular electrical integration time. Such detector may received at least a portion of the signal for a time duration which has at least one first portion with at least one first power level that is greater than a predetermined threshold and at least one second portion immediately preceding or following the at least one first portion. The second portion can have at least one second power level which is less than the predetermined threshold, and may be extended for a time period which is approximately at least 10% of the particular electrical integration time.

In addition, the signal may be at least one of frequency components of the combination, and the particular detector can receive such frequency component. The source electro-magnetic radiation can be generated by a source arrangement which may be a pulsed broadband source. The source electro-magnetic radiation generated by the pulsed source may be a single pulse per the particular electrical integration time. The pulsed source may be a Q-switched laser, a cavity-dumped mode-lock laser, and/or a gain-switched laser. The source electro-magnetic radiation generated by the source arrangement may be a burst of radiation that extends for at most approximately 90% of the particular electrical integration time. The burst of radiation may include multiple pulses. The source electro-magnetic radiation generated by the pulsed broadband source can have a spectrum with (i) a center wavelength between approximately 700 nanometers and 2000 nanometers, and/or (ii) a spectral width of approximately greater than 1% of the center wavelength. The source electro-magnetic radiation generated by the pulsed broadband source may have a pulse width approximately shorter than 1 μsec. A duration of the burst of radiation can be approximately shorter than 1 μsec.

According to another exemplary embodiment of the present invention, the source arrangement generating the source electro-magnetic radiation may include an optical gating switch. A frequency of the source electro-magnetic radiation can vary over time. A mean frequency of the source electro-magnetic radiation may change (i) substantially continuously over time at a tuning speed that is greater than 100 terahertz per millisecond, and/or (ii) with a repetition period that is less than approximately 90% of the particular electrical integration time. The source electro-magnetic radiation can have a tuning range (i) with a center wavelength between approximately 700 nanometers and 2000 nanometers, and/or (ii) of approximately greater than 1% of the center wavelength. The source electro-magnetic radiation may have an instantaneous line width and a tuning range, with the instantaneous line width being less than approximately 10% of the tuning range. The source arrangement may include (i)a tunable laser, (ii) a tunable filter, and/or (iii) a medium, and can generate the source electro-magnetic radiation based on a non-linearity associated with the medium. The frequency may vary substantially (i) linearly with time, and/or (ii) sinusoidally with time.

A detector arrangement which includes the detectors can be provided, that includes an electrical shutter that is adapted to gate a transmission of photoelectrons associated with the combination of the first and second electro-magnetic radiation, wherein a time period for the gating to allow the transmission of the photoelectrons is less than approximately 90% of the particular electrical integration time. The sample can be a biological sample. The detection arrangement may include at least one charged-coupled device. The source arrangement may be a pulsed broadband source. At least one spectral separating unit can be provided which separates spectrum of the first electro-magnetic radiation, the second electro-magnetic radiation and/or the combination into the at least one of the frequency components.

These and other objects, features and advantages of the present invention will become apparent upon reading the following detailed description of embodiments of the invention, when taken in conjunction with the appended claims.

BRIEF DESCRIPTION OF THE DRAWINGS

Further objects, features and advantages of the invention will become apparent from the following detailed description taken in conjunction with the accompanying figures showing illustrative embodiments of the invention, in which.

DETAILED DESCRIPTION

Figure 1:
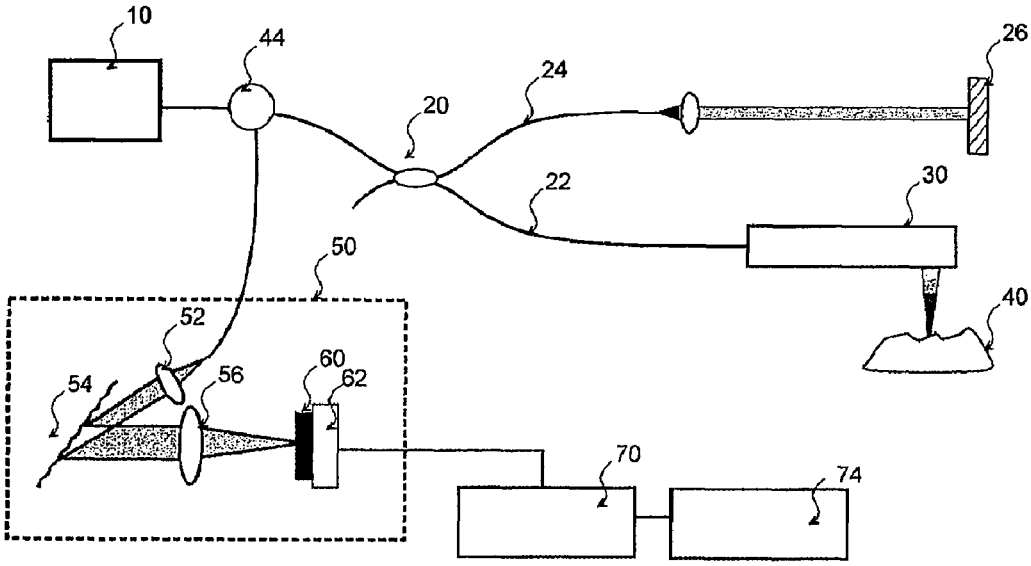
FIG. 1 is an exemplary schematic diagram of a conventional SD OCT system.

FIG. 1 depicts an exemplary basic configuration of a spectral-domain optical coherence tomography ("SD-OCT") system. Broadband light 10 is split by a coupler 20 into a sample arm 22 and a reference arm 24 that is terminated by a mirror 26 at its distal end. A probe 30 at the end of the sample arm delivers light to a sample 40, and receives the light backscattered from within the sample. The light returned from the two interferometer arms is recombined and directed via a circulator 44 to a spectrometer 50 consisting of a collimator 52, a diffraction grating 54, and a lens 56, a CCD array 60, and camera 62. Individual pixels of the CCD array 60 measure the optical power as a function of wave number, $k=2\pi/\lambda$ where $\lambda$ is the optical wavelength. The CCD output is digitized using a digitizer 70 and processed in a computer 74. A discrete Fourier transform ("DFT") of the CCD scan output produces an axial reflectance profile of the sample (A-line). A 2-D tomographic image can be obtained by acquiring multiple A-lines as the probe beam is scanned over the sample along a transverse direction. This exemplary architecture and the operating principle described above are well known in the art.

Figure 2A:
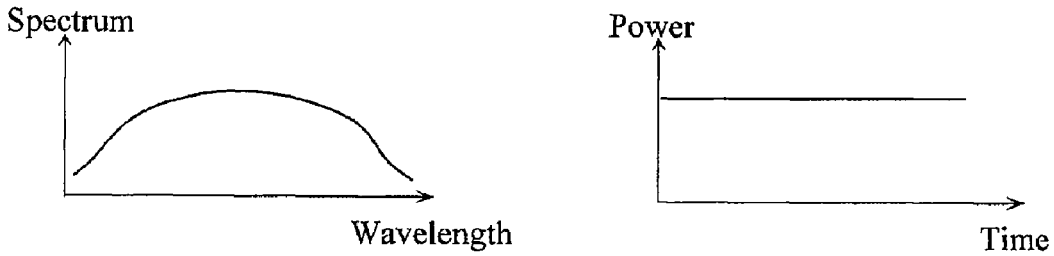
FIG. 2A is a set of exemplary graphs of spectral and temporal characteristics obtained from a conventional continuous-wave optical source.
Figure 2B:
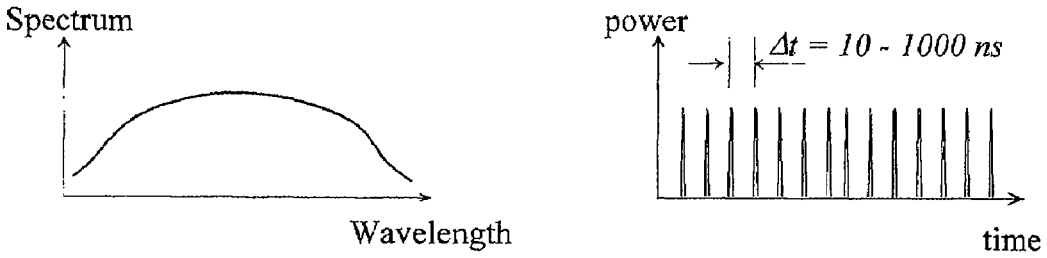
FIG. 2B is a set of exemplary graphs of spectral and temporal characteristics obtained from a high-repetition rate mode locked laser source.

The broadband optical source used in prior art can be categorized into two types: continuous wave ("cw") as shown in FIG. 2A, and mode-locked pulsed source as shown in FIG. 2B. The cw source emits constant spectrum and constant output power. In this case, the integration time of OCT signals is equal to the exposure time of the detector array. Examples of such cw sources include super luminescent diodes, amplified spontaneous emission ("ASE") source, and supercontinuum source. On the other hand, the mode-locked source emits very short optical pulses with a duration ranging from sub nanoseconds to several femtoseconds and a relatively high repetition rate from 10 MHz to 1 GHz. The exposure time of CCD is typically in the order of 10 microseconds to 10 milliseconds. As a result, the mode-locked pulses essentially behave like continuous wave, illuminating the CCD array constantly over its entire exposure time. The use of the cw and mode-locked source in OCT has two shortcomings: (a) significant motion artifacts due to relatively long signal integration time and (b) SNR degradation in case <100% duty cycle of signal integration in the detector array. The exemplary embodiments according to the present inventions provide sample solutions to such problems.

One exemplary embodiment of the present invention relates to a system for imaging of a sample, e.g., biological sample, which may include a source arrangement that generates at least one source electro-magnetic radiation forwarded to the sample and a reference. Such exemplary system may include at least one detection arrangement that has a plurality of detectors, at least one of the detectors capable of detecting a signal associated with a combination of at least one first electro-magnetic radiation received from the sample and at least one second electro-magnetic radiation received from the reference. At least one particular detector may have a particular electrical integration time, and can receive at least a portion of the signal for a time duration which has a first portion with a first power level greater than a predetermined threshold and a second portion immediately preceding or following the first portion. The second portion may have a second power level that is less than the predetermined threshold, and extends for a time period which is approximately more than 10% of the particular electrical integration time.

The electro-magnetic radiation is preferably light with a center wavelength in the range of 700 to 2000 nm. The detector array is preferably charge-coupled devices ("CCD"). Using the exemplary SD-OCT system, the signal detected in the detector array is frequency components of the combination, or the spectrum. Typically the spectrum is obtained using a spectrally separating device such as a diffraction grating. A number of methods to obtain the spectrum with detector arrays are well known in the art. For full-field OCT, the signal is the optical power of the combination, which is linked to specific transverse locations in the sample.

In another exemplary embodiment of the present invention, the source arrangement can be a pulsed broadband source generating a single pulse per the particular electrical integration time or producing a burst of radiation that extends for at most approximately 90% of the particular electrical integration time. Each burst may include multiple ultrashort optical pulses in it. Examples of the pulsed sources include a Q-switched laser, a cavity-dumped mode-lock laser, and a gain-switched laser. Preferably, the spectrum of the pulsed source may have a spectral width of approximately greater than 1% of the center wavelength and a pulse width or a duration of the burst of radiation approximately shorter than 1 microseconds. The source arrangement may comprise a broadband cw source and an optical gating switch or electrical shutter integrated in the CCD array. The time window where the optical power is less than the threshold can be considered as OFF state, and the window where the power is greater than the threshold as ON state. The threshold is preferably less than 50% of the power level during ON state, however a typical pulsed source may provide much larger power extinction between the ON and OFF state. During a single detector integration time, one or multiple ON states may exist, however the total illumination span, or the duration from the start of the first ON state to the end of the last ON state is preferably shorter than 90% of the detector integration time. For example, the shorter the illumination span, the more suppression of motion artifacts can be obtained.

In yet another exemplary embodiment of the present invention, the source arrangement can be a wavelength swept source where a mean frequency of the output spectrum varies over time. The mean frequency of the source electro-magnetic radiation may change substantially continuously over time at a tuning speed that is greater than 100 terahertz per millisecond and repeatedly with a repetition period that is less than approximately 90% of the particular electrical integration time. The tuning range of the source electro-magnetic radiation may have a tuning range with a center wavelength between approximately 700 nanometers and 2000 nm, a tuning width of approximately greater than 1% of the center wavelength, and an instantaneous line width of less than approximately 10% of the tuning range. Such a source arrangement includes a tunable laser, soliton laser in conjunction with Raman self frequency shift, or cw broadband source in conjunction with a tunable filter. The mean frequency may vary substantially linearly or sinusoidally with time. As for the pulsed source, the time window where the optical power received by a specific pixel is less than the threshold can be considered as OFF state for the particular pixel, and the window where the power is greater than the threshold as ON state. The threshold is preferably less than 50% of the power level during ON state, however a typical pulsed source may provide much larger power extinction between the ON and OFF state. During the detector integration time of the pixel, one or multiple ON states may exist, however the total illumination span, or the duration from the start of the first ON state to the end of the last ON state is preferably shorter than 90% of the pixel integration time. The shorter the illumination span is, the more suppression of motion artifacts can be obtained.

According to still another exemplary embodiment of the present invention, a method may be provided for imaging of a sample, typically biological sample. For example, at least one source electro-magnetic radiation may be generated to be forwarded to the sample and a reference. At least a portion of a signal associated may be detected with a combination of at least one first electro-magnetic radiation received from the sample and at least one second electro-magnetic radiation received from the reference using at least one detector of a plurality of detectors of a detection arrangement. At least one particular detector may have a particular electrical integration time, and can receive at least a portion of the signal for a time duration which has a first portion with a first power level greater than a predetermined threshold and a second portion immediately preceding or following the first portion. The second portion may have a second power level less than the predetermined threshold, and can extend for a time period which is approximately more than 10% of the particular electrical integration time.

Figure 3:
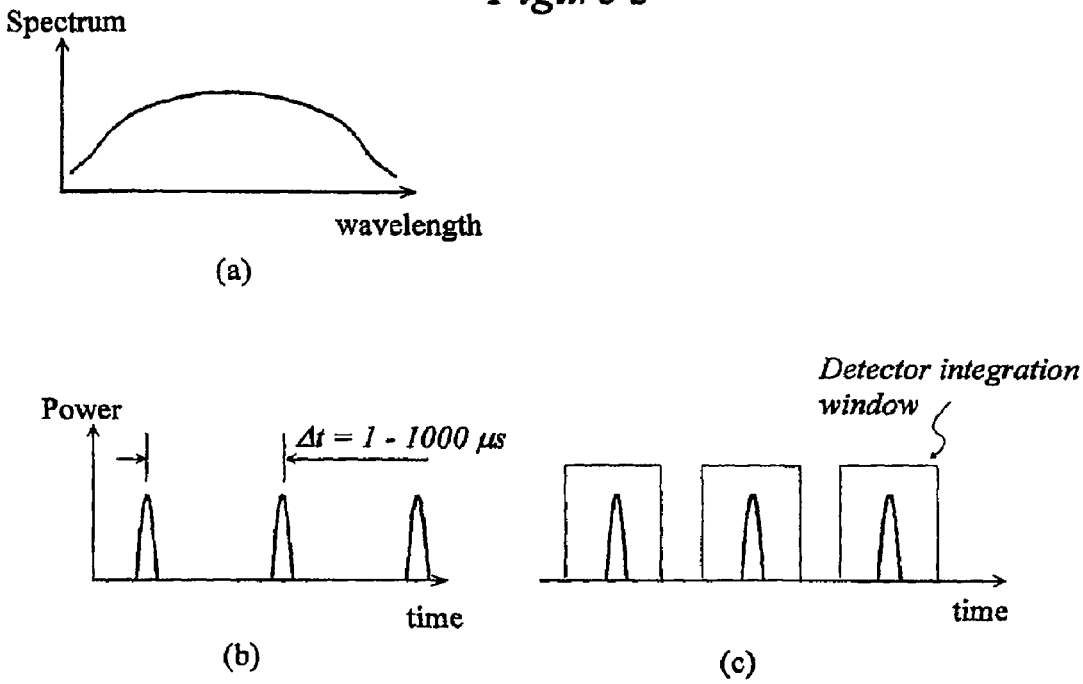
FIG. 3 is a set of exemplary graphs of spectrum and temporal characteristics obtained from a low-repetition rate broadband source.
Figure 4:
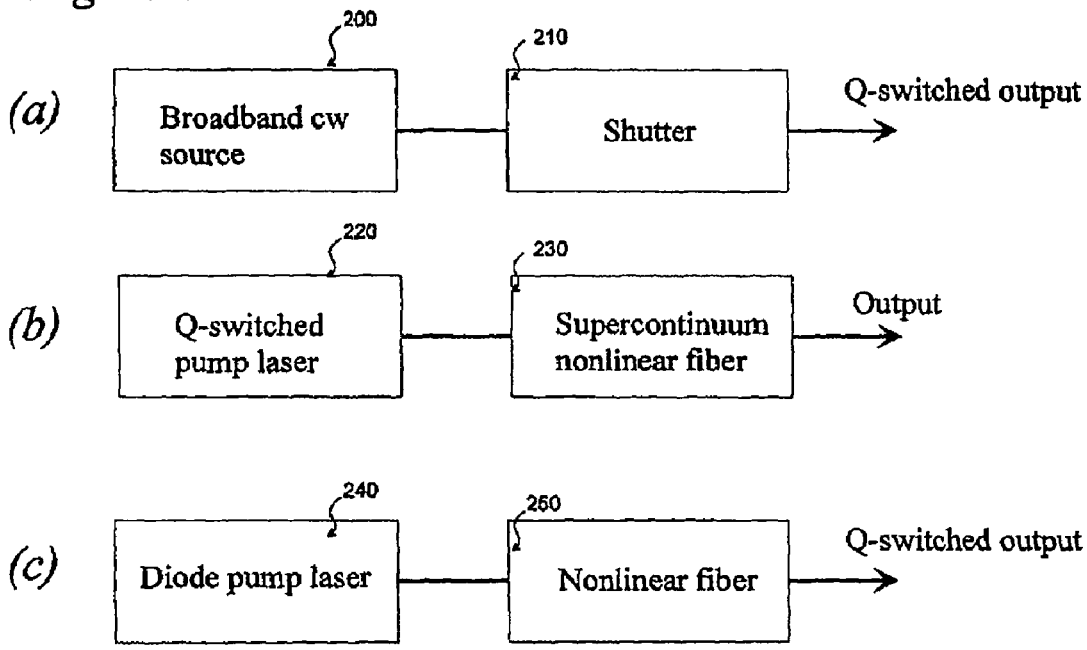
FIGS. 4(a)-(c) are block diagrams of exemplary embodiments of low-repetition broadband source arrangements according to the present invention.

FIG. 3 illustrates sample outputs of one exemplary embodiment of a system and method according to the present invention that is based on a broadband pulsed source. Such source emits a single burst of optical energy, or simply "pulse", per each integration window of the detector array with timing synchronization between the pulses and integration window of the detector array, as illustrated in FIG. 3. Examples of such sources may include time-gated cw or mode-locked broadband source 200 using an external intensity modulator 210 (as shown in FIG. 4(a)), supercontinuum source based on a Q-switched pump laser 220 and supercontinuum generation medium 230 (as shown in FIG. 4(b)), self-Q-switched supercontinuum source or Raman source based on pump laser 240 and nonlinear medium 250 (as shown in FIG. 4(c)). The use of such source results in an effective signal integration time equal to the duration of the pulse, which may range from sub microseconds to sub nanoseconds, substantially shorter than the integration time of the detector array itself. Although a single pulse operation is described, other optical sources emitting multiple pulses per each integration time may be used if the pulses are generated within duration substantially shorter than the detector integration time. In exemplary clinical applications such as ophthalmology, the maximum optical energy or intensity level that can be illuminated to the retina is limited by potential damage to the tissue. Using the exemplary arrangement shown in FIG. 4(a), it is possible to use a broadband source emitting a high output power, such as SLD and Ti:Sapphire mode-locked laser, and time-gate the output to decrease the duty cycle and therefore an effective exposure energy level to the sample.

Figure 5:
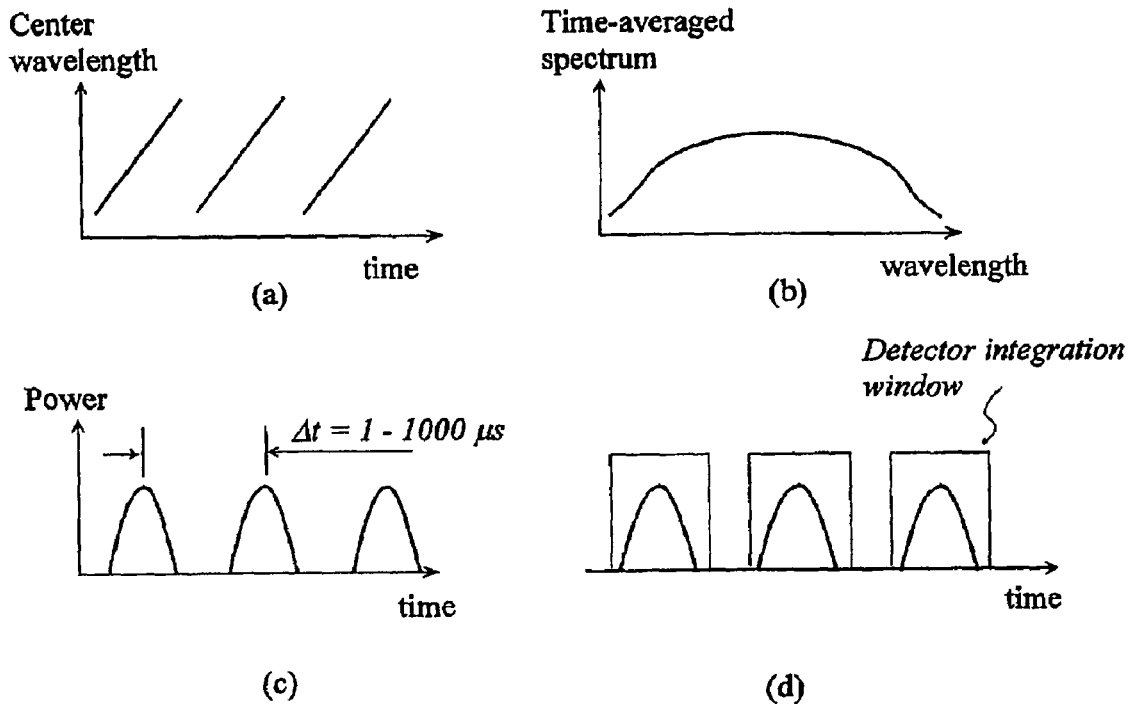
FIGS. 5(a)-(d) are exemplary graphs of spectrum and temporal characteristics obtained from an exemplary wavelength-swept source.

FIGS. 5(a)-(d) illustrate graphs to explain the principle of another exemplary embodiment of the present invention based on a wavelength-swept source which emits substantially narrowband spectrum that is swept over a wide spectral range, repeatedly in time. FIG. 5(c) show exemplary signals generated using a swept source with the output wavelength swept in a saw-tooth fashion. The tuning cycle is synchronized with the integration window of the detector array. In this exemplary case, each detector element can receive the light with corresponding wavelength during only a short period of time which determines the effective signal integration time. As a numerical example, when the total tuning range is 150 nm, centered at 1300 nm, and the instantaneous linewidth is 1 nm, the effective signal integration time can be only one hundredth of the detector integration time.

Figure 6:
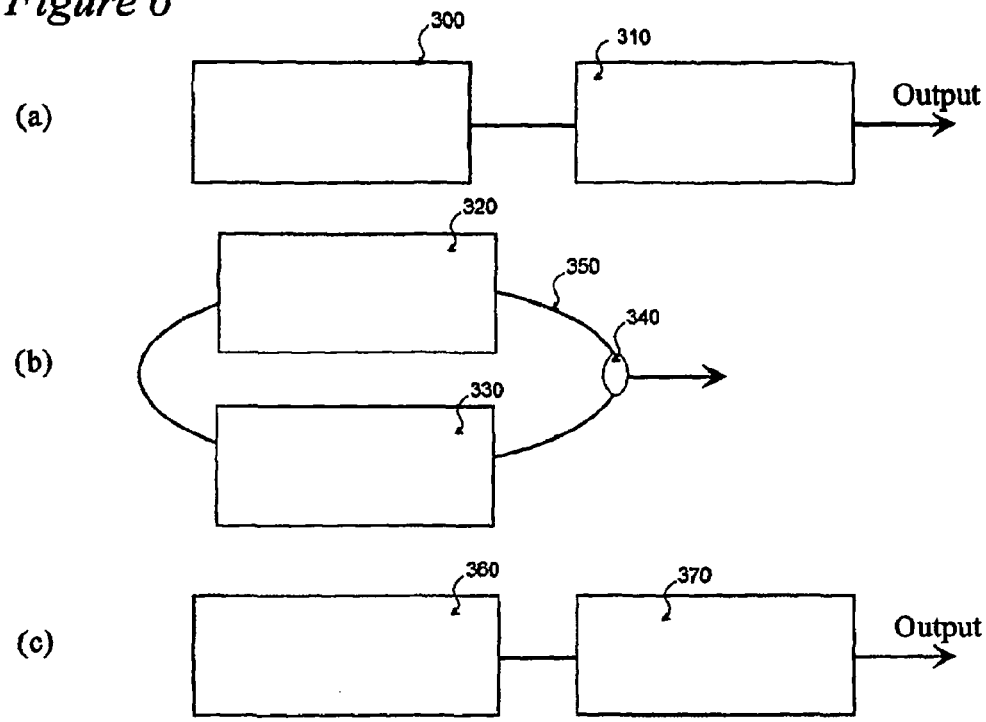
FIGS. 6(a)-(c) are block diagrams of exemplary embodiments of an exemplary wavelength-swept source arrangements according to the present invention.

As shown in FIGS. 6(a)-(c), a wavelength-swept source may be implemented by using a conventional broadband source 300 followed by a wavelength scanning filter 310. According to an exemplary variant of the present invention, a wavelength-swept laser may be used using a gain medium 320, tunable filter 330 and output coupler 340 in a laser cavity 350. A wavelength-swept laser may be configured to yield a linewidth that is narrower than the resolution of the spectrometer; in this case the complexity and tolerance in spectrometer design may be relaxed. The combination of wavelength-swept source and detector array described above may be analogized with optical frequency domain imaging and exhibits motion artifacts such as Doppler distortion. To further reduce the motion artifacts, the wavelength-swept source may be operated in a low-duty-cycle or Q-switched regime, with an advantage of further reduction of effective signal integration time. Another possible source can includes a broadly tunable source based on soliton self frequency shift using a soliton source 360 and Raman medium 370.

Exemplary conventional SD-OCT systems utilize either a continuous-wave (cw) broad-spectrum light source, such as super luminescent diodes (SLD), or ultrashort mode-locked pulses with a high repetition rate in the range of 10-100 MHz. Full field OCT systems have typically employed cw thermal light source. For such conventional systems, the CCD array is illuminated constantly, and therefore the exposure time of the CCD camera determines the signal acquisition time for a single A-line. However, sample or probe motion during the A-line acquisition time can result in various undesirable artifacts such as signal fading and spatial resolution degradation. In particular, due to axial sample motion, the visibility of detected spectral fringes can diminish significantly resulting in significant image fading. Considering that cameras appropriate for SD-OCT typically provide exposures times longer than 10 μs, a solution to the fringe washout problem is preferable for biomedical applications where sample and probe motion is common.

Figure 7:
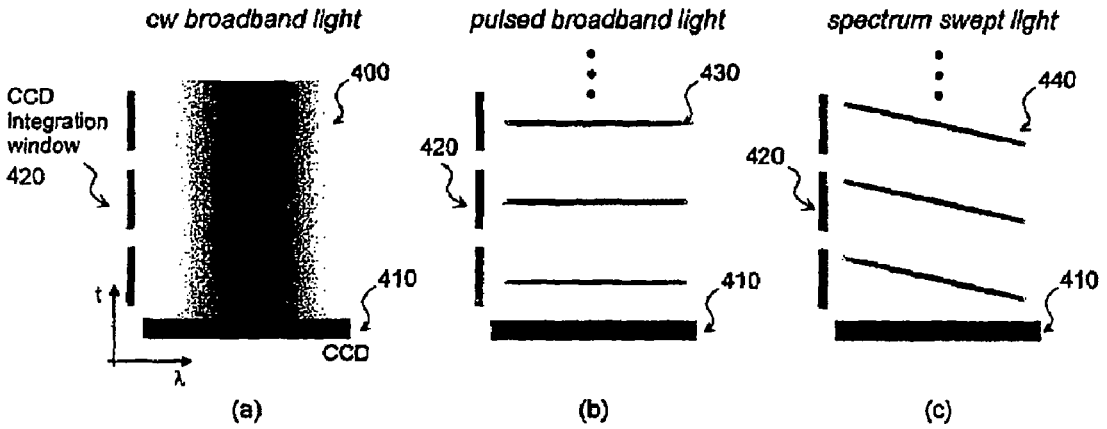
FIG. 7(a) is an exemplary illustration of a detection signal of a cw light with a CCD array in a spectrometer.
FIG. 7(b) is an exemplary illustration of a detection signal of a pulsed light with a CCD array in a spectrometer.
FIG. 7(c) is an exemplary illustration of a detection signal of a swept light with a CCD array in a spectrometer.

FIGS. 7(a)-(c) illustrates exemplary illustration of a detection signal with a CCD array in a spectrometer how the signal detection in the exemplary SD-OCT system for three different light sources: broadband cw source (see FIG. 7(a)), broadband pulsed source (see FIG. 7(a)), and narrowband wavelength-swept source (see FIG. 7(a)). In this figure, spectrally dispersed, broad-spectrum light 400 is incident on a CCD array 410 so that each CCD pixel receives a narrowband portion of the source light. The vertical bars 420 represent the time window during which the camera integrates photon-generated electrons. FIG. 7(a) shows the signals obtained using a common implementation of the SD-OCT system. The operational principles of the systems generating signals shown in FIGS. 7(b) and (c) are described below.

In particular, FIG. 7(b) depicts a train of short broadband pulses 430 with a repetition rate equal to the CCD readout rate. The integration time of this exemplary system is given by the pulse duration rather than the camera readout time. As a result, snap-shot A-line profiles can be obtained with freedom from sample or probe motion. This exemplary technique is conceptually similar to the use of stroboscopic illumination in photography. Although for most biomedical applications nanosecond pulses are sufficiently short to avoid motion artifacts, it is interesting to note that in principle, this approach could provide femtosecond temporal resolution A-line acquisition through the use of low-repetition mode locked lasers. The following analysis, however, pertains to an arbitrary pulsed source delivering either single bursts of short-duration broadband light or bursts comprising a brief train of mode locked pulses.

To understand the imaging characteristics of a pulsed-source SD-OCT system, the signal-to-noise ratio (SNR) for pulsed and cw operation in the presence of axial motion may be reviewed. For example, let $T_s$ and $T_e$ denote the duration of the pulse and the electrical integration time of the camera, respectively. For a sample moving axially in parallel to an optical probe beam with a speed $v_z$, the signal power S, normalized to the signal at $v_z=0$, is given by $$S \approx \left|\int_o^{T_e} P(t) e^{j2k_o v_z 2} dt\right|^2 / \int_o^{T_e} P(t) dt^2, \quad (1)$$

where P(t) represents time-varying optical power of the pulse, and $k_o=2\pi/\lambda_o$ denotes the wave number corresponding to the center wavelength $\lambda_o$. Equation 1 yields $S \approx \sin^2 (k_o \Delta z)/(k_o \Delta z)^2$ for a square pulse and $S \approx \exp[-k_o^2 \Delta z^2 /(2\ln 2)]0$ for a Gaussian pulse with $T_s$ as the full-width-at-half-maximum ("FWHM") pulse duration, where $\Delta z = v_z T_s$ represents the total sample movement during pulse duration $T_s$. These expressions imply that significant signal fading occurs if the sample movement is greater than a half optical wavelength during the pulse duration. Therefore, the short pulsed technique ($T_s \ll T_e$) offers a significant advantage over the conventional cw operation in terms of motion-induced signal fading. Similarly, one can see that pulsed operation can also suppress other motion artifacts, such as spatial resolution degradation due to sample motion and transverse beam scanning.

The fundamental noise characteristics of pulsed operation are likely approximately identical to those of cw operation, because the detection bandwidth is solely determined by the integration time of the camera. If both a pulsed and cw sources produce the same average optical power and relative intensity noise ("RIN"), both would yield the same SNR in the limit of a stationary sample.

FIG. 7(c) shows signals generated using another exemplary techniques that uses another exemplary pulsed-source SD-OCT approach that is based on a narrowband, wavelength-swept source. Since the optical spectrum 440 incident to the CCD array 420 is continuously changed in time, each of the CCD pixels receives its corresponding spectral component only for a short time interval. As with pulsed broad bandwidth illumination, rapidly sweeping the wavelength allows the SD-OCT signal to be free from signal fading due to fringe washout. However, unlike pulsed operation, individual "spectrum pulses" do not arrive at the CCD pixels at the same time.

For a linear sweep shown in FIG. 7(c), the swept operation is approximately analogous to optical frequency domain imaging ("OFDI") as described in U.S. patent application No. 60/514,769 filed Oct. 27, 2003, the entire disclosure of which is incorporated herein by reference. In this exemplary swept operation, spectral fringes are measured as a function of time using a swept source and a standard photodiode. Therefore, both imaging techniques can exhibit similar motion artifacts. The generation of motion artifacts in produced by the exemplary OFDI system is known. The swept-source operation in the exemplary SD-OCT system, however, differs from the operations of the OFDI system in that it does not require a linear tuning slope or narrow instantaneous linewidth of the source because these specifications are governed by the detection spectrometer. Such distinctions are significant considering that tuning speed and power in wavelength swept lasers are often limited by constraints on linearity and instantaneous linewidth.

Figure 8:
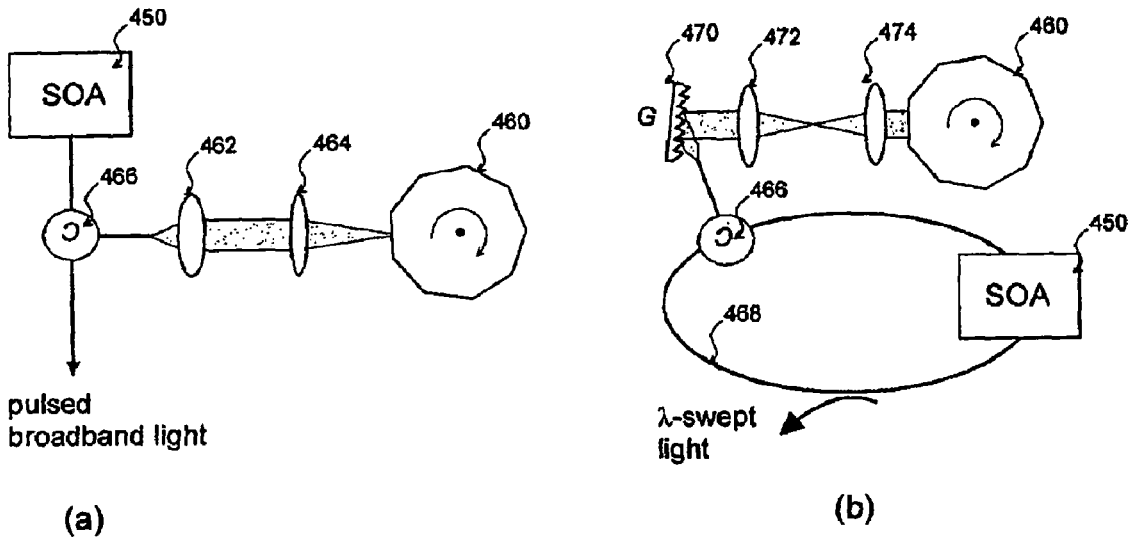
FIG. 8(a) is a schematic of an exemplary pulsed ASE source.
FIG. 8(b) is a schematic of an exemplary wavelength-swept source.
Figure 9:
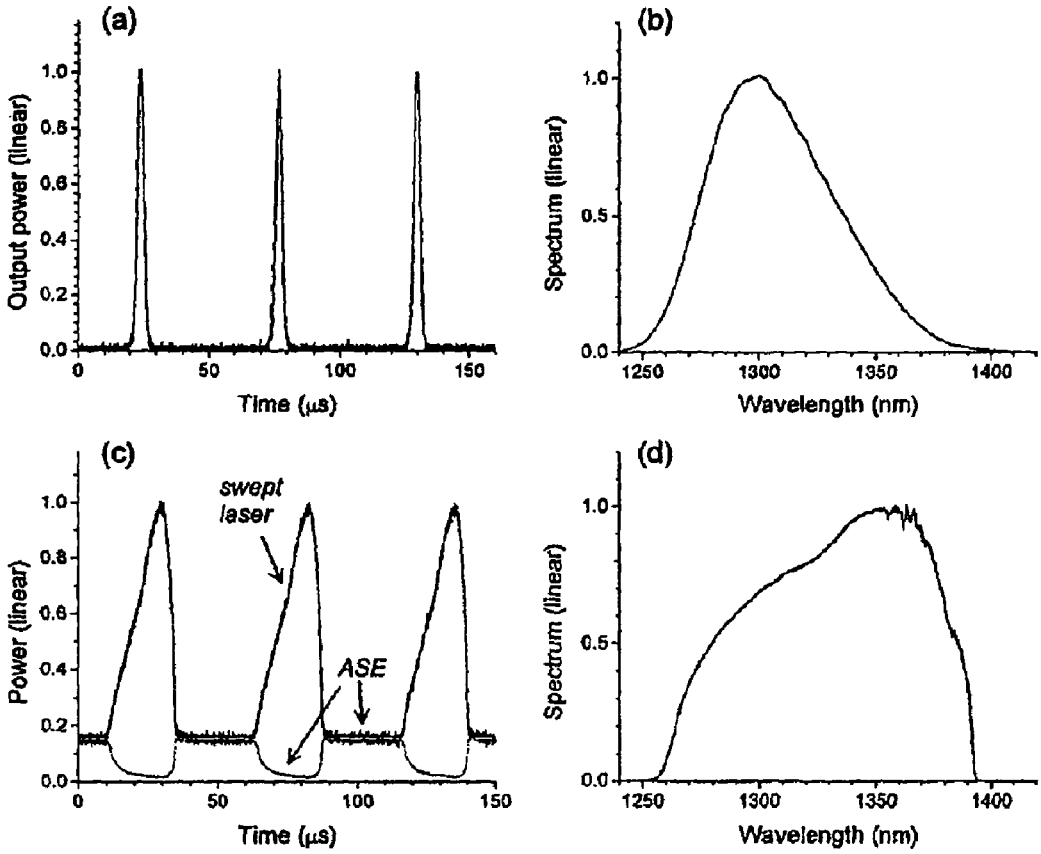
FIGS. 9(a) and (b) are illustrations of signals of exemplary temporal and spectral output characteristics obtained from the exemplary pulsed ASE source.
FIGS. 9(c) and (d) are illustrations of signals of exemplary temporal and spectral output characteristics obtained from the exemplary swept source.

For example, pulsed and wavelength-swept sources may be constructed according to an exemplary embodiment of the present invention. A block diagram of the exemplary system of the present invention which includes a gating device is shown in FIG. 8(a). The pulsed broadband source can be provided by an external time-gating of cw broadband amplified spontaneous emission ("ASE") from a semiconductor optical amplifier 450 (e.g., SOA, Philips CQF 882/e). The output of the SOA, prior to the time gating, can be characterized as cw un-polarized ASE centered 1.3 μm, with 7-mW total power at an injection current of 450 mA. The cw ASE can be coupled to an external optical gating device which includes a polygonal mirror scanner 460 and lenses 462, 464, in conjunction with a circulator 466. The polygonal mirror had 40 facets with a facet-to-facet angle of 9 degrees. The focal lengths of the collimating 462 and focusing 464 lenses can be 11 and 100 mm, respectively, to obtain a duty cycle of approximately 5% in the output. FIG. 9(a) shows an output pulse train measured with an InGaAs photodetector and oscilloscope (detection bandwidth=100 MHz) as the polygon scanner may be rotated at 474 revolutions per second to produce a pulse repetition rate of 18.94 kHz. The measured pulse width and corresponding duty cycle were 2.85 μs (FWHM) and 5.4%, respectively. The average output power measured with a power meter can be 300 μW. FIG. 9(b) shows the output spectrum measured with an optical spectrum analyzer. The spectrum may be approximately identical to that of the input ASE, with a center wavelength at 1300 nm and a FWHM of 66 nm.

FIG. 8(b) shows a block diagram of another exemplary embodiment of a system according to the present invention which includes the wavelength-swept laser. The laser employed the same SOA 450 and a scanning wavelength filter based on a polygonal mirror scanner 460 in a fiber-optic ring laser cavity 468. The scanning filter consisted of a diffraction grating 470 (830 lines per mm), two lenses in 4f configuration (472; f=60 mm, 474; f=63.5 mm), and the same 40-facet polygonal mirror scanner 460 as used for the pulsed source. The scanning filter can be configured to have a free spectral range of 275 nm centered at 1320 nm wavelength, which may result in a duty cycle of the laser output closely matched to that of the CCD camera (46%). When the pass band of the filter scans outside the gain bandwidth of the SOA, the source likely does not reach the lasing threshold and simply produces ASE. FIG. 9(c) shows the temporal characteristics of the laser output at a sweep repetition rate of 18.94 kHz. The region where the output power varies with a Gaussian-like profile corresponds to when the source was operated above the lasing threshold. Outside this region, the output is ASE with a constant power. To determine how much the ASE level contributed to the detected light during swept laser operation, the backward-propagating ASE power was measured by inserting a 5% tap coupler in the cavity between the filter and SOA (lower trace in FIG. 9(c), gray line). The ASE level dropped significantly during laser operation because ASE was suppressed due to gain saturation in the SOA. The laser-to-ASE ratio reached as high as 16 dB in the middle of the lasing tuning range. Horizontal bars (green) represent the integration window of the camera, which was synchronized with laser tuning. The average output power measured with a power meter was 18 mW.

FIG. 9(d) shows an exemplary output spectrum measured with the optical spectrum analyzer in a peak-hold mode. In a peak-hold mode, the contribution of ASE to the measurement would be negligible owing to its much lower spectral density than laser light at a given time. Therefore, the measured spectrum represents the tuning envelope of the swept laser. The tuning range was approximately 135 nm, centered at 1325 nm. An exemplary instantaneous linewidth of the swept output was approximately 0.4 nm, as determined by measuring the coherence length with a variable-delay interferometer.

Figure 10:
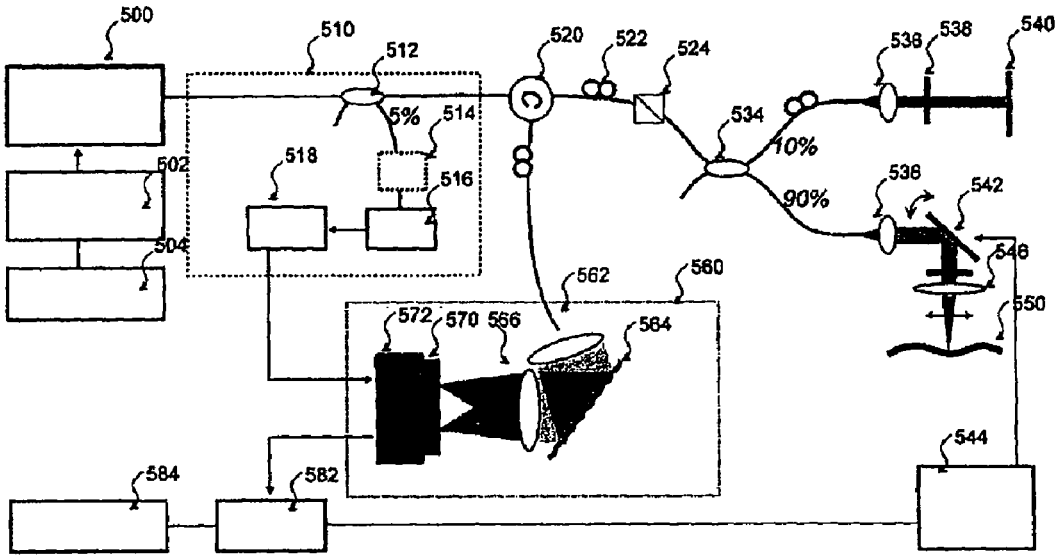
FIG. 10 is an exemplary block diagram of an exemplary embodiment of an SD OCT system according to the present invention.

FIG. 10 shows a block diagram of yet another exemplary embodiment of the system according to the present invention. This exemplary system includes an interferometer, a probe, and a detection spectrometer which have been described in detail in elsewhere in detail S. H. Yun et al., "High-speed spectral domain optical coherence tomography at 1.3 μm wavelength," Opt. Express 11, 3598-3604 (2003). In summary, this exemplary system included a light source 500, scanner driver 502, scanner clock generator 504, optical trigger generator 510 comprising a 5% tap 512, an (optional) optical narrowband filter 514, photodetector 516, and a TTL generating circuit 518. The narrowband filter 514 is used for a swept source operation, but is not needed for the pulsed broadband source operation. The interferometer can include a circulator 520, polarization controllers 522, polarizer 524, 1‰ coupler 534, collimator 536, neutral density filter 538, reference mirror 540, galvanometer-mounted mirror 542, galvanometer driver 544, imaging lens 546, sample 550. The detection arm may include a spectrometer 560 that has a collimator 562, grating 564, imaging lens 566, CCD linear array 570, camera 572. A galvanometer can be used in the probe to provide transverse beam scanning across a sample with a FWHM beam diameter and confocal length of 18 μm and 1.1 mm, respectively. The detection spectrometer 560, shown in the dash-dot box, consisted of a ruled diffraction grating 564 with 1,200 lines per mm, focusing lens 566 (f=150 mm), and a line scan camera (LSC) with a 512-element InGaAs CCD array (Sensors Unlimited Inc., SU512LX). Polarization controllers were adjusted to maximize the fringe visibility in the CCD. A total wavelength span of 106 nm centered at 1320 nm was projected to the 512-element CCD array with a spectral resolution of 0.1 nm.

The camera readout can be triggered by an external TTL signal generated from the source output. In the case of the pulsed light source, the electrical trigger pulses were generated directly from the optical pulses, as illustrated in the dotted box in FIG. 10. In the swept source case, the laser output may be transmitted through a combination of a circulator and a fiber Bragg grating reflector with 0.2 nm bandwidth and 90% reflectivity (the narrowband filter arrangement being presented by a small dotted box 510). The photodetector can then detect a train of short pulses generated when the output spectrum of the laser swept through the reflection band of the Bragg grating. From the photodetector output, TTL trigger pulses were generated with adjustable phase delay.

As described above, both lasers may be operated at a repetition rate of 18.939 kHz. This rate corresponded to the maximum readout rate of the camera. Upon receiving the trigger, the camera integrates photo-generated electrons for 24.4 μs; in the subsequent 28.4 μs period, the integrated voltage can be read out. By adjusting the phase delay in a PPL pulse generator, the integration time window of the camera was aligned to the output of the light sources, as shown in FIGS. 7(a) and (c). The camera output can be digitized with a 4-ch, 12-bit data acquisition board 582 (National Instruments, NI PCI-6115) and processed in a personal computer 584. The data processing may involve zero padding, interpolation and mapping to linear k-space, prior to a fast Fourier transform to create an image.

Figure 11:
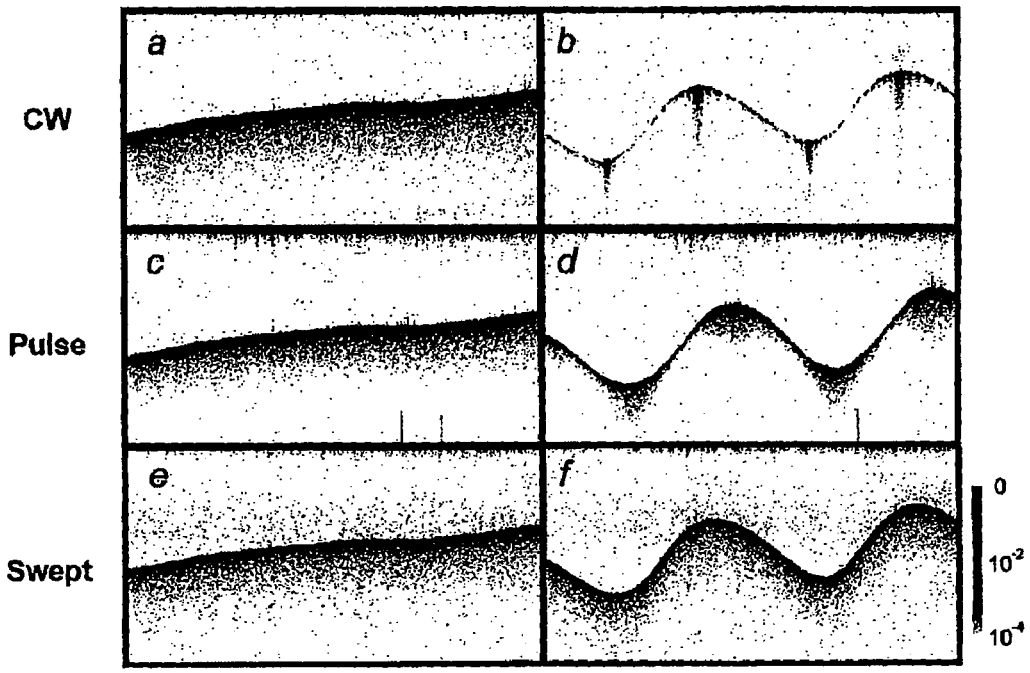
FIG. 11 is an exemplary illustration of SD-OCT images of a paper, acquired when a sample is static (in sections a, c and e) and moving at 80 Hz over 0.8 mm (in sections b, d and f) with three different light sources.

SD-OCT imaging can be performed using three different light sources: (a) the cw ASE obtained directly from the SOA, (b) the intensity-gated ASE pulses (as shown in FIG. 8(a)), and (c) the wavelength swept laser (as shown in FIG. 8(b)). In order to investigate motion artifacts, a sample can be constructed by mounting paper on an acoustic speaker. FIG. 11 shows exemplary images obtained with three different sources for comparison purposes. Shown on the left portion of FIG. 11 are exemplary OCT images acquired using cw, pulsed, and swept light, respectively, when the paper sample was kept stationary. Each image includes 256 axial and 500 transverse pixels, spans a depth of 2.1 mm and a width of 5 mm, and was acquired over a total time period of 26.4 ms. The images are generated using a logarithmic inverse grayscale over a dynamic range of 40 dB in reflectivity (as shown as a grayscale map in FIG. 11). For each of the light sources, the optical power illuminating the sample was adjusted approximately to the same level by using neutral density filters in the probe. The offset of the gray-scale map for each light source can be finely adjusted so that the three static images (See FIG. 11, sections a, c, and e) exhibited nearly the same contrast. Images of the axially moving sample (see FIG. 11, sections b, d, and f) may be acquired when the speaker was driven with a sinusoidal waveform at 80 Hz with peak-to-peak amplitude of 0.8 mm. Signal fading due to fringe washout is distinct for the case of the cw ASE source (see FIG. 11, section b). Except near the peaks and valleys of the oscillation when the axial velocity is zero, the image contrast and penetration depth may be noticeably degraded. In contrast, the image d can be obtained with the pulsed source and exhibits considerably reduced image fading. Signal fading may not be observed while using the wavelength swept source (see FIG. 11, section f).

Figure 12:
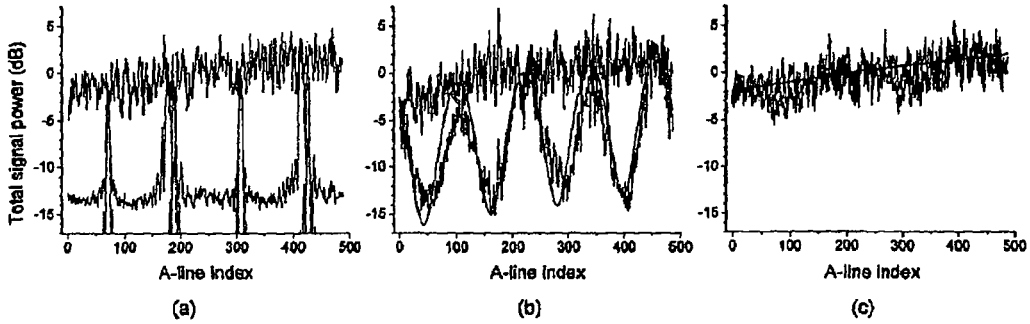
FIG. 12(a) is an illustration of a variation of a total signal power, a sum of reflectivity of 256 depth points in each A-line, as a function of A-line index or time, obtained from images a and b shown in FIG. 11.
FIG. 12(b) is an illustration of a variation of a total signal power, a sum of reflectivity of 256 depth points in each A-line, as a function of A-line index or time, obtained from images c and d shown in FIG. 11.
FIG. 12(c) is an illustration of a variation of a total signal power, a sum of reflectivity of 256 depth points in each A-line, as a function of A-line index or time, obtained from images e and f shown in FIG. 11.

To quantify the amount of signal fading, a sum of the pixel values in the unit of linear power along each A-line may be obtained from the exemplary images shown in FIG. 11, representing a total signal power in the particular A-line. A total of 200 pixels, from the $31^{st}$ to $230^{th}$ elements, were considered in the summation. The results thereof are shown in FIGS. 12(a)-(c), such that the results in FIG. 12(a) corresponds to the signals obtained using to the cw source (see FIG. 11, sections a and b), the results in FIG. 12(b) corresponds to the signals obtained using the pulsed source (see FIG. 11, sections c and d), and the results in FIG. 12(c) corresponds to the signals obtained using the swept source (see FIG. 11, section e and 1).

In each graph, the integrated signal power is plotted as a function of A-line index for the stationary-sample image (a lighter line) and the moving-sample image (a darker line). As depicted by the lighter lines, the signal power for the stationary sample exhibits random fluctuation due to speckle as the probe beam is scanned across the sample with standard deviation of approximately 2 dB. The speckle-averaged mean value varies linearly over transverse locations of the sample, a variation that was attributed to the finite confocal parameter and resulting depth-dependent light collection efficiency. The signal power traces obtained from FIG. 11, section b, d, and f (darker lines) clearly demonstrate the benefit of the pulsed and swept source in terms of reducing motion-induced signal fading.

The time gated pulses may provide a factor 8.6 reduction in signal integration time, from 24.4 μs to 2.85 μs. For the swept source with an instantaneous linewidth of 0.4 nm, individual CCD pixels may be illuminated for only 75 ns per each A-line acquisition representing a 325-fold reduction in signal integration time. Theoretical curves based on Eq. (1) show good correspondence with the experimental results with the following exceptions. The experimental noise floor can prohibit detection of signal loss greater than −14 dB; the small discrepancy between the blue and black curves in FIG. 12(c), by up to 3 dB, is attributed to the uneven probe collection efficiency at different depths of the two samples.

An exemplary SNR analysis indicates that the pulsed ASE source produced essentially the same noise characteristics as cw ASE of the same average optical power. However, images which may be acquired using the wavelength swept laser exhibited a noise floor that can be 10-20 dB higher, depending on depth, than that observed when using the ASE source of the same average power. We attribute this increased noise floor to the RIN of the swept laser in the frequency band from DC to 41 kHz corresponding to a reciprocal of the CCD integration time. The best sensitivity obtained with the swept source may be approximately −95 dB at a reference-arm power of 1-2 μW.

Figure 13:
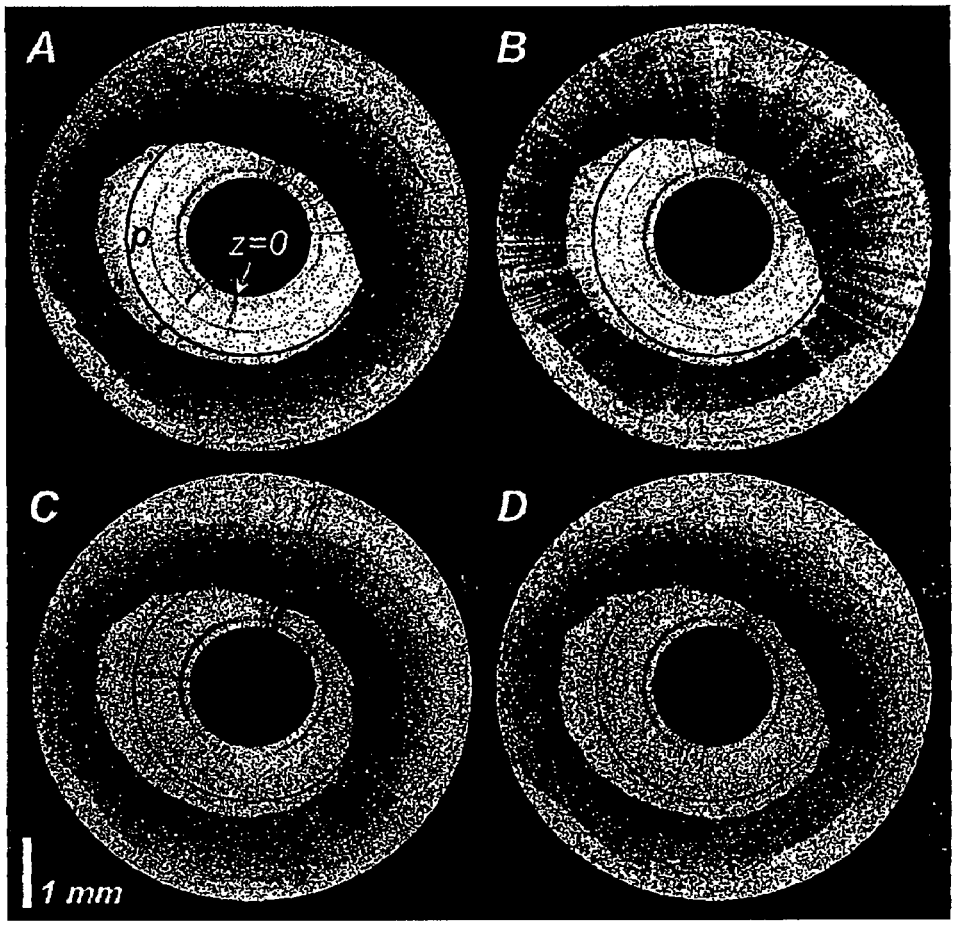
FIG. 13 is a set of illustrations of exemplary SD-OCT images of a human. coronary artery in vitro, obtained using an exemplary embodiment of the system according to the present invention, with a rotation speed of a catheter and the light source (Section A—4.5 rps, cw ASE source, Section B—37.9 rps, cw ASE source, Section C—4.5 rps, swept source, and Section C—37.9 rps, swept source)

Exemplary SD-OCT imaging of a human coronary artery in vitro may be conducted by use of a fiber-optic catheter. The fiber-optic catheter comprised a graded-index lens and a 90-degree prism at its distal end and was connected to the interferometer through a high-speed rotational joint which could provide a rotational speed of up 100 revolutions per second (rps). FIG. 13 shows exemplary images obtained with the cw ASE source (see images A and B of FIG. 13) and the swept source (see images C and D of FIG. 13) at the same A-line acquisition rate of 18.94 kHz. The difference between images of images A and B and images C and D is the rotational speed of the catheter, which was 9.5 rps for images A and C, corresponding to 2000 A-lines per image, and 37.9 rps for images B and D, corresponding to 500 A-lines per image. Zero delay of the interferometer was positioned between the sample and the outer prism surface, resulting in a circular artifact superimposed on the image of the tissue (marked asp).

Image A may represent a typical OCT image of a vessel. In contrast, Image B can exhibit distinct radial streaks due to loss of signal This image fading may be attributed mainly to catheter-induced modulation in path length, increasing with the rotational speed. The path length modulation can result from three mechanisms: (a) rotational beam scanning of an off-center object inevitably results in axial path length variation of the probe beam, as if the probe was retracting or approaching to the sample; (b) the tip of a rotating catheter can wobble in a protection sheath to modulate the distance between the probe and the sample; (c) mechanical vibration from a rotation joint can modulate the length of the optical fiber inside the catheter by twist or strain. Such third mechanism was thought to a dominant cause in this particular experiment, since the circle (p) corresponding to the prism surface also suffers from significant loss of contrast at the same radial locations. Images C and D of FIG. 13 are exemplary SD-OCT images obtained with the swept source. The signal fading is not noticeable in image D, demonstrating clearly the benefit of the pulsed-source approach.

Thus, multiple strategies can be applied to realize the benefit of pulsed or gated illumination. Traditional light sources include cw SLD's, supercontinuum sources, or mode-locked lasers. Each of these sources can be converted into a pulsed source by use of an external intensity modulation scheme. As an intensity modulator or switch, one may consider electro-optic or acousto-optic modulators or injection current modulation. Alternatively, CCD cameras with built-in electrical shutters may be used. This external gating approach, however, has a main drawback in that it results in a loss of optical power and therefore may degrade the detection sensitivity. However, in situations where motion causes significant signal fading through fringe washout, external gating can lead to a better sensitivity despite the loss of optical power. In other applications, however, the usable optical power in the system is often limited by the maximum permissible exposure of the sample. In this case, external gating would be an effective way to attenuate the power level entering the system from a powerful source. For example, ophthalmologic retinal imaging has been performed with SD-OCT at a wavelength of 800-nm. At this wavelength, the maximum permissible cw exposure to the eyes is limited to approximately 600-700 μW according to American National Standards Institute (ANSI). For this application, one could gate the output from a commercially available mode-locked Ti:Sapphire laser and, while still providing sufficient power to the system, reduce sensitivity to motion by more than an order of magnitude.

Instead of external gating, various power-efficient internal modulation techniques may be employed. For example, Q-switching and cavity dumping are well known techniques applicable to ultrashort pulsed lasers. Q-switched supercontinuum sources with repetition rates of a few to tens of kHz have been reported and may be suitable for use in the exemplary SD-OCT systems. Beside the benefit of reducing motion artifacts, the reduced fringe washout of the pulsed source approach may also facilitate quadrature fringe detection based on sequential phase dithering.

The use of a wavelength swept source as described in this manuscript is essentially a hybrid between the OFDI and SD-OCT techniques that may permit otherwise less-flexible OFDI source requirements including narrow instantaneous linewidth and tuning linearity to be relaxed. In this case, the high resolution and linearity of the spectrometer can accommodate a swept laser with a nonlinear tuning element such as a resonantly scanned Fabry-Perot filter or a tunable source based on soliton self-frequency shifting in nonlinear fibers. Furthermore, the relaxed requirement on the instantaneous linewidth of a swept laser may facilitate the generation of higher output powers.

Figure 14:
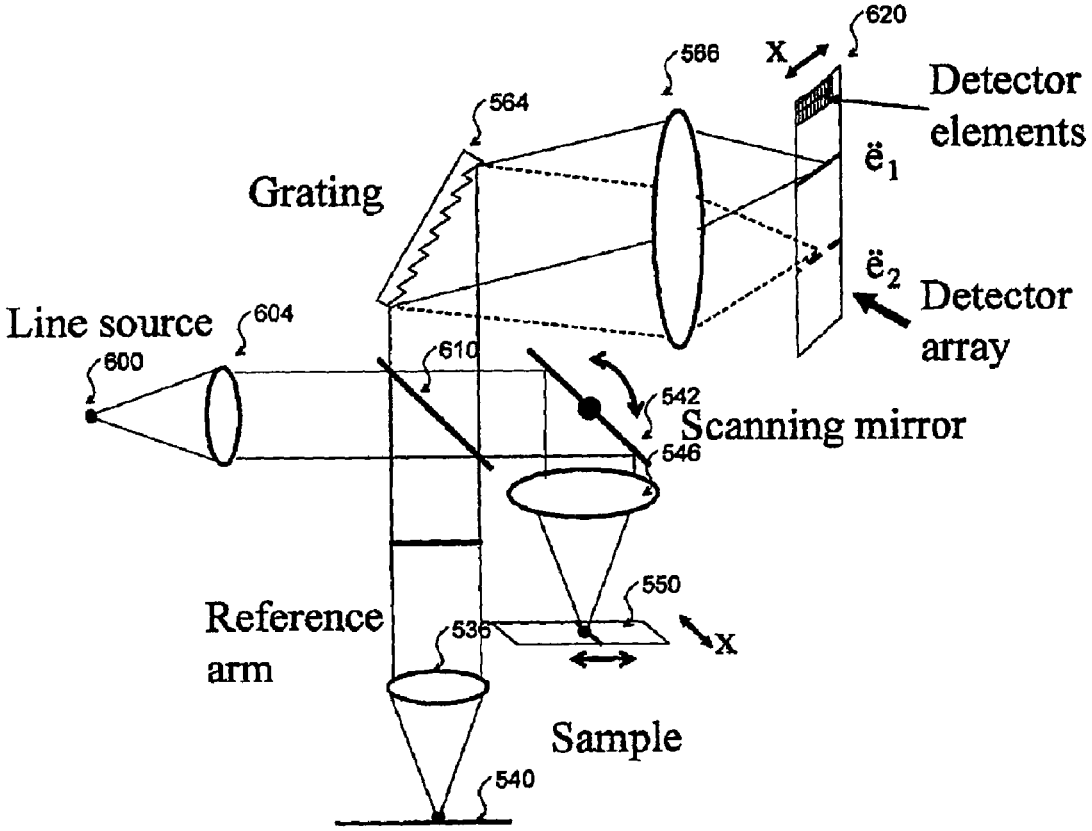
FIG. 14 is a block diagram of another exemplary SD-OCT system that uses a line pulsed or swept source and a two-dimensional CCD array.

In another exemplary embodiment of the system according to the present invention, each of the CCD arrays can be a 2-dimensional array. Two dimensional simultaneous scanning can be performed by using the 2-dimensional array, where along one axis of the array spectral information is encoded, while across the second dimension spatial information is encoded. FIG. 14 shows a block diagram of such exemplary system which may include a line source 600, lens 604, beam splitter 610, and a two-dimensional CCD array 620. The tissue is preferably illuminated by a line beam, and the illuminated portion in the sample is imaged on one dimension of the array, while the light is spectrally dispersed in the other direction of the array. As previously discussed, long integration times with a continuous source lead to motion artifacts and fringe washout. Also, read-out times of 2-dimensional arrays are larger that of 1-dimensional arrays. By using a pulsed source, motion artifacts and fringe wash-out can be avoided, where the exposure time of the array is significantly shorter than the frame transfer rate. Since the light intensity is distributed over a line, more power is allowed to be incident on the tissue. When using a pulsed source with pulse durations longer than 100 femtoseconds, the source can be treated as semi-continuous in ophthalmic applications. Thus, high peak power can be used over short periods of time, while the average power is in compliance with ANSI standards for light exposure of tissue. In addition, a swept source can be used in combination with line illumination, where the detector can be a 1 or 2 dimensional array. In case of a one dimensional array, the tissue information over a full line is acquired for each wavelength consecutively by a 1-dimensional array. By using a 2-dimensional array, the wavelength is encoded along the second dimension of the array.

Figure 15:
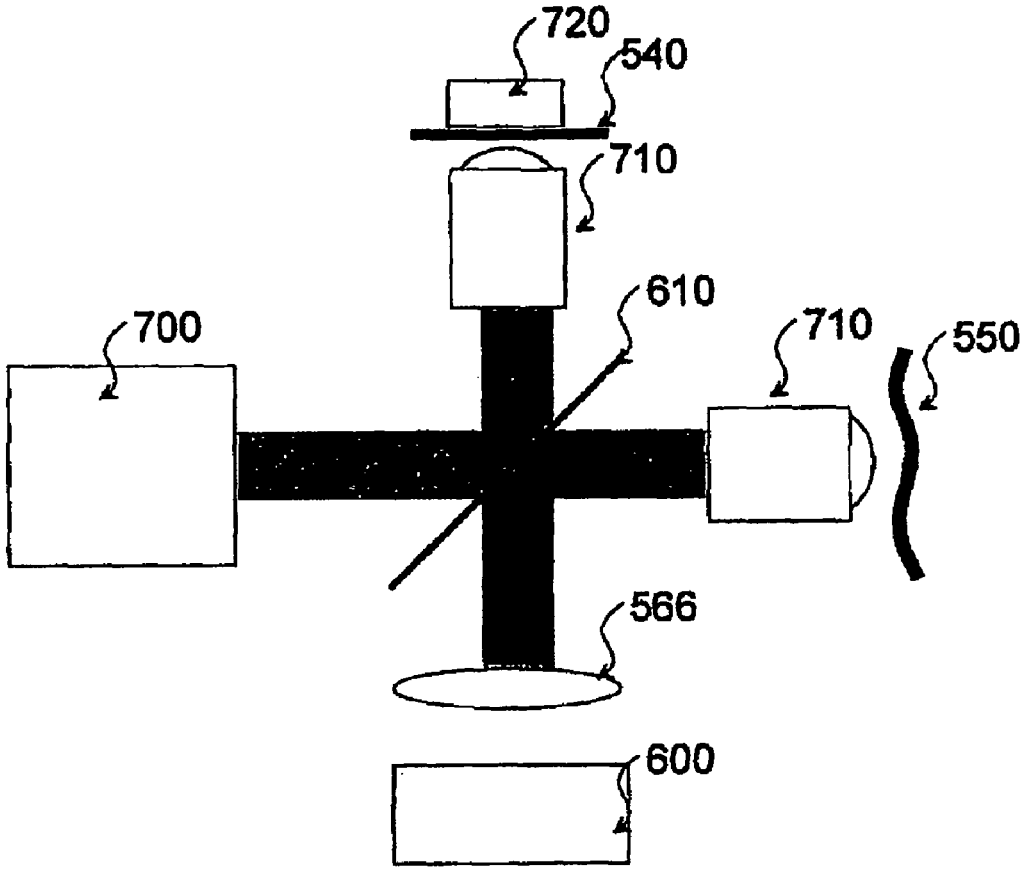
FIG. 15 is a block diagram of an exemplary full-field OCT system that uses a pulsed source and a two-dimensional CCD array.

As yet another exemplary embodiment of the present invention, a pulsed source can be employed in full-field optical coherence tomography, as depicted in FIG. 15 as a block diagram. The detector array is typically a 2-dimensional CCD array. The operating principle and generic system architecture for full-field OCT is well known in the art. Full-field OCT typically produces en face images. As with the earlier description of SD-OCT, the pulsed-source approach effectively reduces the effective signal acquisition time in a CCD array which is typically two dimensional. The repetition rate is matched to the frame readout rate of the CCD array. Since a typical full-field OCT technique is not based on spectral-domain interferometry, the swept source approach does not provide an advantage in full-field OCT in terms of motion artifacts. Nevertheless, a swept source whose sweep repetition rate is matched to the CCD readout rate may be still usable for full-field OCT as an alternative source to conventional broadband source. This is because of the fact that a swept spectrum seen by the CCD in a time-integrated manner is identical to a broadband spectrum of a same spectral envelope. The light source 700 is preferably spatially incoherent source, such as Halogen or Tungsten lamp in Kohler configuration, but operated in a pulsed regime to reduce the motion artifacts in full-field imaging. The source beam is divided into a reference and a sample by a beam splitter. High-NA objective lenses 710 are typically used. The reference mirror 540 may be attached to a mechanical actuator such as PZT for phase dithering to realize heterodyne detection.

The invention disclosed here may be used in various imaging applications, ranging from coronary artery imaging, GI tract, ophthalmologic imaging, to monitoring of dynamic biological or chemical process, moving materials and components, where high-sensitivity, high-speed, motion-artifact-free imaging is preferred.

The foregoing merely illustrates the principles of the invention. Various modifications and alterations to the described embodiments will be apparent to those skilled in the art in view of the teachings herein. For example, the invention described herein is usable with the exemplary methods, systems and apparatus described in U.S. Provisional Patent Application No. 60/514,769 filed Oct. 27, 2003, and International Patent Application No. PCT/US03/02349 filed on Jan. 24, 2003, the disclosures of which are incorporated by reference herein in their entireties. It will thus be appreciated that those skilled in the art will be able to devise numerous systems, arrangements and methods which, although not explicitly shown or described herein, embody the principles of the invention and are thus within the spirit and scope of the present invention. In addition, all publications, patents and patent applications referenced above are incorporated herein by reference in their entireties.

What is claimed is:

1. A system for imaging at least a portion of a sample, comprising:

a source arrangement generating at least one source electro-magnetic radiation forwarded to the sample and a reference; [and]

at least one detection arrangement including a plurality of detectors, at least one of the detectors capable of detecting a signal associated with a combination of at least one first electro-magnetic radiation received from the sample and at least one second electro-magnetic radiation received from the reference, *wherein the signal is at least one of frequency components of the combination;*

*at least one spectral separating unit which separates spectrum of at least one of the first electro-magnetic radiation, the second electro-magnetic radiation or the combination into the at least one of the frequency components,* wherein at least one particular detector of the detectors has a particular electrical integration time, wherein the at least one particular detector receives at least a portion of the signal for a time duration which has at least one first portion with at least one first power level greater than a predetermined threshold and at least one second portion immediately preceding or following the at least one first portion, the at least one second portion having at least one second power level less than the predetermined threshold, and wherein the at least one second portion is extended for a time period which is approximately at least 10% of the particular electrical integration time; *and*

*at least one processing arrangement which is configured to generate at least one image associated with the sample based on the detected signal which is provided for the particular electrical integration time, the at least one image including at least one portion associated with the sample below a surface thereof, and the at least one portion of the at least one image illustrates the sample at multiple depths thereof immediately below a surface location at which the forwarded radiation impacts the sample.*

[2. The system according to claim 1, wherein the signal has frequency components of the combination.]

3. The system according to claim 1, wherein the source arrangement is a pulsed broadband source.

4. The system according to claim 1, wherein the detection arrangement includes at least one charged-coupled device.

5. The system according to claim [2] *1*, wherein the at least one particular detector receives the at least one of the frequency components.

6. The system according to claim 5, wherein the source arrangement is a pulsed broadband source.

7. The system according to claim 5, wherein the source arrangement includes an optical gating switch.

8. The system according to claim 5, wherein a frequency of the at least one source electro-magnetic radiation varies over time.

9. The system according to claim 5, wherein the detector arrangement further includes an electrical shutter that is adapted to gate a transmission of photoelectrons associated with the combination of the first and second electro-magnetic radiation, wherein a time period for the gating to allow the transmission of the photoelectrons is less than approximately 90% of the particular electrical integration time.

10. The system according to claim 5, wherein the sample is a biological sample.

11. The system according to claim 5, wherein the detection arrangement includes at least one charged-coupled device.

[12. The system according to claim 5, further comprising at least one spectral separating unit which separates spectrum of at least one of the first electro-magnetic radiation, the second electro-magnetic radiation and the combination into the at least one of the frequency components.]

13. The system according to claim 6, wherein the at least one source electro-magnetic radiation generated by the pulsed source is a single pulse per the particular electrical integration time.

14. The system according to claim 6, wherein the at least one source electro-magnetic radiation generated by the source arrangement is a burst of radiation that extends for at most approximately 90% of the particular electrical integration time.

15. The system according to claim 6, wherein the at least one source electro-magnetic radiation generated by the pulsed broadband source has a spectrum with a center wavelength between approximately 700 nanometers and 2000 nanometers.

16. The system according to claim 6, wherein a duration of the burst of radiation is approximately shorter than 1 μsec.

17. The system according to claim 8, wherein a mean frequency of the at least one source electro-magnetic radiation changes substantially continuously over time at a tuning speed that is greater than 100 terahertz per millisecond.

18. The system according to claim 8, wherein the mean frequency changes repeatedly with a repetition period that is less than approximately 90% of the particular electrical integration time.

19. The system according to claim 8, wherein the at least one source electro-magnetic radiation generated by the source arrangement has a tuning range with a center wavelength between approximately 700 nanometers and 2000 nanometers.

20. The system according to claim 8, wherein the at least one source electro-magnetic radiation generated by the source arrangement has a timing range of approximately greater than 1% of the center wavelength.

21. The system according to claim 8, wherein the at least one source electro-magnetic radiation generated by the source arrangement has an instantaneous line width and a tuning range, the instantaneous line width being less than approximately 10% of the tuning range.

22. The system according to claim 8, wherein the source arrangement includes a tunable laser.

23. The system according to claim 8, wherein the source arrangement includes a tunable filter.

24. The system according to claim 8, wherein the source arrangement includes a medium, and wherein the source arrangement generates the at least one source electro-magnetic radiation based on a non-linearity associated with the medium.

25. The system according to claim 8, wherein the frequency varies substantially linearly with time.

26. The system according to claim 8, wherein the frequency varies substantially sinusoidally with time.

27. The system according to claim 13, wherein the pulsed source includes at least one of a Q-switched laser, a cavity-dumped mode-lock laser, and a gain-switched laser.

28. The system according to claim 13, wherein the at least one source electro-magnetic radiation generated by the pulsed broadband source has a pulse width approximately shorter than 1 μsec.

29. The system according to claim 14, wherein the burst of radiation includes multiple pulses.

30. The system according to claim 15, wherein the at least one source electro-magnetic radiation generated by the pulsed broadband source has a spectrum with a spectral width of approximately greater than 1% of the center wavelength.

31. A method for imaging at least a portion of a sample, comprising:

generating at least one source electro-magnetic radiation forwarded to the sample and a reference; [and]

detecting at least a portion of a signal associated with a combination of at least one first electro-magnetic radiation received from the sample and at least one second electro-magnetic radiation received from the reference using at least one detector of a plurality of detectors of a detection arrangement, *wherein the signal is at least one of frequency components of the combination;*

*separating spectrum of at least one of the first electro-magnetic radiation, the second electro-magnetic radiation or the combination into the at least one of the frequency components,* wherein at least one particular detector of the detectors has a particular electrical integration time, and wherein the at least one particular detector receives at least a portion of the signal for a time duration which has a first portion with a first power level greater than a predetermined threshold and a second portion immediately preceding or following the first portion, the second portion having a second power level less than the predetermined threshold, and extending for a time period which is approximately more than 10% of the particular electrical integration time*; and*

*generating at least one image associated with the sample based on the detected signal which is provided for the particular electrical integration time, the at least one image including at least one portion associated with the sample below a surface thereof, and the at least one portion of the at least one image illustrates the sample at multiple depths thereof immediately below a surface location at which the forwarded radiation impacts the sample*.

[32. The method according to claim 31, wherein the signal has frequency components of the combination.]

33. The method according to claim 31, wherein the generating step is performed by a source arrangement which is a pulsed broadband source.

34. The method according to claim 31, wherein the detection step is performed by a detection arrangement which includes at least one charged-coupled device.

35. The method according to claim [32] *31*, wherein the at least one particular detector receives the at least one of the frequency components.

36. The method according to claim 35, wherein the generating step is performed by a source arrangement which is a pulsed broadband source.

37. The method according to claim 35, wherein the source arrangement includes an optical gating switch.

38. The method according to claim 35, wherein a frequency of the at least one source electro-magnetic radiation varies over time.

39. The method according to claim 35, wherein the detector arrangement further includes an electrical shutter that is adapted to gate a transmission of photoelectrons associated with the combination of the first and second electro-magnetic radiation, wherein a time period for the gating to allow the transmission of the photoelectrons is less than approximately 90% of the particular electrical integration time.

40. The method according to claim 35, wherein the sample is a biological sample.

41. The method according to claim 35, wherein the detecting step is performed by a detection arrangement which includes at least one charged-coupled device.

[42. The method according to claim 35, further comprising the step of separating spectrum of at least one of the first electro-magnetic radiation, the second electro-magnetic radiation and the combination into the at least one of the frequency components.]

43. The method according to claim 36, wherein the at least one source electro-magnetic radiation generated by the pulsed source is a single pulse per the particular electrical integration time.

44. The method according to claim 36, wherein the at least one source electro-magnetic radiation generated by the source arrangement is a burst of radiation that extends for at most approximately 90% of the particular electrical integration time.

45. The method according to claim 36, wherein the at least one source electro-magnetic radiation generated by the pulsed broadband source has a spectrum with a center wavelength between approximately 700 nanometers and 2000 nanometers.

46. The method according to claim 36, wherein a duration of the burst of radiation is approximately shorter than 1 μsec.

47. The method according to claim 38, wherein a mean frequency of the at least one source electro-magnetic radiation changes substantially continuously over time at a tuning speed that is greater than 100 terahertz per millisecond.

48. The method according to claim 38, wherein the mean frequency changes repeatedly with a repetition period that is less than approximately 90% of the particular electrical integration time.

49. The method according to claim 38, wherein the at least one source electro-magnetic radiation generated by the source arrangement has a tuning range with a center wavelength between approximately 700 nanometers and 2000 nanometers.

50. The method according to claim 38, wherein the at least one source electro-magnetic radiation generated by the source arrangement has a timing range of approximately greater than 1% of the center wavelength.

51. The method according to claim 38, wherein the at least one source electro-magnetic radiation generated by the source arrangement has an instantaneous line width and a tuning range, the instantaneous line width being less than approximately 10% of the tuning range.

52. The method according to claim 38, wherein the source arrangement includes a tunable laser.

53. The method according to claim 38, wherein the source arrangement includes a tunable filter.

54. The method according to claim 38, wherein the source arrangement includes a medium, and wherein the source arrangement generates the at least one source electro-magnetic radiation based on a non-linearity associated with the medium.

55. The method according to claim 38, wherein the frequency varies substantially linearly with time.

56. The method according to claim 38, wherein the frequency varies substantially sinusoidally with time.

57. The method according to claim 43, wherein the pulsed source includes at least one of a Q-switched laser, a cavity-dumped mode-lock laser, and a gain-switched laser.

58. The method according to claim 43, wherein the at least one source electro-magnetic radiation generated by the pulsed broadband source has a pulse width approximately shorter than 1 μsec.

59. The method according to claim 44, wherein the burst of radiation includes multiple pulses.

60. The method according to claim 45, wherein the at least one source electro-magnetic radiation generated by the pulsed broadband source has a spectrum width a spectral width of approximately greater than 1% of the center wavelength.

* * * * *